US009695171B2

(12) United States Patent
Galatsis et al.

(10) Patent No.: US 9,695,171 B2
(45) Date of Patent: Jul. 4, 2017

(54) 3,4-DISUBSTITUTED-1 H-PYRROLO[2,3-B]PYRIDINES AND 4,5-DISUBSTITUTED-7H-PYRROLO[2,3-C]PYRIDAZINES AS LRRK2 INHIBITORS

(71) Applicant: Pfizer Inc., New York, NY (US)

(72) Inventors: Paul Galatsis, Newton, MA (US); Matthew Merrill Hayward, Old Lyme, CT (US); Bethany Lyn Kormos, Somerville, MA (US); Travis T. Wager, Brookline, MA (US); Lei Zhang, Auburndale, MA (US); Jaclyn Louise Henderson, Cambridge, MA (US); Ravi G. Kurumbail, East Lyme, CT (US); Patrick Robert Verhoest, Newton, MA (US); Antonia Friederike Stepan, Cambrdige, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/104,659

(22) PCT Filed: Dec. 3, 2014

(86) PCT No.: PCT/IB2014/066563

§ 371 (c)(1),
(2) Date: Jun. 15, 2016

(87) PCT Pub. No.: WO2015/092592

PCT Pub. Date: Jun. 25, 2015

(65) Prior Publication Data

US 2017/0002000 A1 Jan. 5, 2017

Related U.S. Application Data

(60) Provisional application No. 61/916,953, filed on Dec. 17, 2013.

(51) Int. Cl.

| | |
|---|---|
| ***C07D 471/04*** | (2006.01) |
| ***C07D 487/04*** | (2006.01) |
| ***C07D 519/00*** | (2006.01) |
| ***C07D 491/08*** | (2006.01) |
| ***C07D 498/08*** | (2006.01) |

(52) U.S. Cl.

CPC ......... *C07D 471/04* (2013.01); *C07D 487/04* (2013.01); *C07D 491/08* (2013.01); *C07D 498/08* (2013.01); *C07D 519/00* (2013.01)

(58) Field of Classification Search

CPC ... C07D 471/04; C07D 487/04; A61K 31/437
See application file for complete search history.

(56) References Cited

U.S. PATENT DOCUMENTS

| | | | |
|---|---|---|---|
| 4,689,338 | A | 8/1987 | Gerster et al. |
| 4,929,624 | A | 5/1990 | Gerster et al. |
| 5,389,640 | A | 2/1995 | Gerster et al. |
| 5,502,187 | A | 3/1996 | Ayer et al. |
| 5,506,347 | A | 4/1996 | Erion et al. |
| 5,646,128 | A | 7/1997 | Firestein et al. |
| 5,658,889 | A | 8/1997 | Gruber et al. |
| 5,674,998 | A | 10/1997 | Boyer et al. |
| 5,686,457 | A | 11/1997 | Traxler et al. |
| 5,721,356 | A | 2/1998 | Ugarkar et al. |
| 5,726,302 | A | 3/1998 | Ugarkar et al. |
| 5,750,349 | A | 5/1998 | Suzuki et al. |
| 5,763,596 | A | 6/1998 | Boyer et al. |
| 5,763,597 | A | 6/1998 | Ugarkar et al. |
| 5,795,977 | A | 8/1998 | Ugarkar et al. |
| 5,864,033 | A | 1/1999 | Browne et al. |
| 6,051,577 | A | 4/2000 | Altmann |

(Continued)

FOREIGN PATENT DOCUMENTS

| | | |
|---|---|---|
| CN | 1102644 | 5/1995 |
| DE | 4304455 | 8/1994 |

(Continued)

OTHER PUBLICATIONS

U.S. Appl. No. 62/469,756, filed Mar. 10, 2017.
U.S. Appl. No. 62/469,468, filed Mar. 10, 2017.
Korean Patent Application No. 2015-7002334 (PCT/IB2013/055039) Notice of Preliminary Rejection, dated Jul. 12, 2016.
International Patent Application No. PCT/IB2014/066563, filed Dec. 3, 2014,International Preliminary Report on Patentability, mailed Jun. 21, 2016, 6 pages.
International Patent Application PCT/IB2016/0553258, filed Sep. 7, 2016, Search Report and Written Opinion, mailed Oct. 24, 2016, 17 pages.
Almansa, C., et al., "Versatile Three Component Coupling for the Synthesis of Pyrazolopyridines and Other Pyrido Fused Systems", Heterocycles, 2008, pp. 1695-1709, 75(7).

(Continued)

*Primary Examiner* — Craig Ricci
*Assistant Examiner* — Christopher R Stone
(74) *Attorney, Agent, or Firm* — John A. Wichtowski

(57) ABSTRACT

The present invention provides novel 3,4-disubstituted-1H-pyrrolo[2,3-b]pyridine derivatives and 4,5-disubstituted-7H-pyrrolo[2,3-c]pyridazine derivatives of Formula I, and the pharmaceutically acceptable salts thereof

I

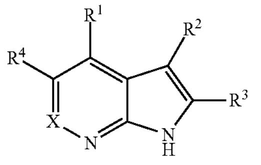

wherein $R^1$, $R^2$, $R^3$, $R^4$ and X are as defined in the specification. The invention is also directed to pharmaceutical compositions comprising the compounds of formula I and to use of the compounds in the treatment of diseases associated with LRRK2, such as neurodegenerative diseases including Parkinson's disease or Alzheimer's disease, cancer, Crohn's disease or leprosy.

7 Claims, No Drawings

(56) References Cited

U.S. PATENT DOCUMENTS

| | | | |
|---|---|---|---|
| 6,096,749 | A | 8/2000 | Traxler et al. |
| 6,610,847 | B2 | 8/2003 | Blumenkopf et al. |
| 6,635,762 | B1 | 10/2003 | Blumenkopf et al. |
| 6,890,929 | B2 | 5/2005 | Blumenkopf et al. |
| 7,115,600 | B2 | 10/2006 | Wager et al. |
| 7,285,293 | B2 | 10/2007 | Castillo et al. |
| 7,569,569 | B2 | 8/2009 | Blumenkopf et al. |
| 7,687,507 | B2 | 3/2010 | Blumenkopf et al. |
| 7,964,607 | B2 | 6/2011 | Verhoest et al. |
| 7,998,966 | B2 | 8/2011 | Bearss et al. |
| 9,156,845 | B2 | 10/2015 | Galatsis et al. |
| 2002/0019526 | A1 | 2/2002 | Blumenkopf et al. |
| 2003/0073655 | A1 | 4/2003 | Chain |
| 2003/0195205 | A1 | 10/2003 | DeNinno et al. |
| 2003/0212273 | A1 | 11/2003 | Blumenkopf et al. |
| 2004/0058922 | A1 | 3/2004 | Blumenkopf et al. |
| 2004/0192889 | A1 | 9/2004 | Bredesen |
| 2004/0220186 | A1 | 11/2004 | Bell et al. |
| 2005/0019328 | A1 | 1/2005 | Schenk |
| 2005/0043354 | A1 | 2/2005 | Wager et al. |
| 2005/0048049 | A1 | 3/2005 | Schenk |
| 2005/0153989 | A1 | 7/2005 | Grotzfeld et al. |
| 2005/0171128 | A1 | 8/2005 | Blumenkopf et al. |
| 2005/0256135 | A1 | 11/2005 | Lunn et al. |
| 2005/0261331 | A1 | 11/2005 | Nielsen et al. |
| 2005/0267095 | A1 | 12/2005 | Bernardelli et al. |
| 2005/0267100 | A1 | 12/2005 | Elliott et al. |
| 2006/0106035 | A1 | 5/2006 | Hendrix et al. |
| 2006/0111372 | A1 | 5/2006 | Hendrix et al. |
| 2007/0031416 | A1 | 2/2007 | Shoji et al. |
| 2007/0049615 | A1 | 3/2007 | Ibrahim et al. |
| 2007/0149561 | A1 | 6/2007 | Dhanak et al. |
| 2007/0179175 | A1 | 8/2007 | Lunn |
| 2008/0096955 | A1 | 4/2008 | Wager et al. |
| 2008/0176925 | A1 | 7/2008 | Butler et al. |
| 2008/0293733 | A1 | 11/2008 | Bearss et al. |
| 2009/0005356 | A1 | 1/2009 | Blaney et al. |
| 2009/0118276 | A1 | 5/2009 | Gopalsamy et al. |
| 2009/0275533 | A1 | 11/2009 | Hsieh et al. |
| 2009/0298823 | A1 | 12/2009 | Song et al. |
| 2009/0325953 | A1 | 12/2009 | Sahoo et al. |
| 2010/0175140 | A1 | 7/2010 | Smith |
| 2010/0184790 | A1 | 7/2010 | Meijer et al. |
| 2011/0082140 | A1 | 4/2011 | Dorsch et al. |
| 2011/0166175 | A1 | 7/2011 | Klein |
| 2011/0190290 | A1 | 8/2011 | Hood et al. |
| 2011/0201599 | A1 | 8/2011 | Bahceci et al. |
| 2011/0218198 | A1 | 9/2011 | Wucherer-Plietker et al. |
| 2011/0269772 | A1 | 11/2011 | Bearss et al. |
| 2012/0245347 | A1 | 9/2012 | Biehl et al. |
| 2014/0256704 | A1 | 9/2014 | Vankayalapati et al. |
| 2015/0366874 | A1 | 12/2015 | Galatsis |

FOREIGN PATENT DOCUMENTS

| | | |
|---|---|---|
| DE | 102008025751 | 12/2009 |
| EP | 339358 | 11/1989 |
| EP | 535548 | 4/1993 |
| EP | 631179 | 12/1994 |
| EP | 676667 | 10/1995 |
| EP | 0682027 | 11/1995 |
| EP | 777150 | 6/1997 |
| EP | 795556 | 9/1997 |
| EP | 846981 | 6/1998 |
| EP | 0994728 | 10/1998 |
| EP | 1052264 | 11/2000 |
| EP | 1070987 | 1/2001 |
| EP | 1257584 | 10/2004 |
| EP | 2210887 | 7/2010 |
| EP | 2338486 | 6/2011 |
| EP | 3386722 | 9/2012 |
| JP | 3271289 | 12/1991 |
| JP | 5310700 | 11/1993 |
| JP | 6041114 | 2/1994 |
| JP | 6116239 | 4/1994 |
| JP | 6247966 | 9/1994 |
| JP | 10177243 | 6/1998 |
| JP | 10213887 | 8/1998 |
| JP | 20011302515 | 10/2001 |
| KR | 2010 0116765 | 11/2010 |
| KR | 20120019785 | 3/2012 |
| WO | 9215581 | 9/1992 |
| WO | 9320078 | 10/1993 |
| WO | 9320847 | 10/1993 |
| WO | 9408975 | 4/1994 |
| WO | 9417043 | 8/1994 |
| WO | 9511898 | 5/1995 |
| WO | 9640705 | 12/1996 |
| WO | 9640706 | 12/1996 |
| WO | 9640707 | 12/1996 |
| WO | 9823613 | 6/1998 |
| WO | 9844955 | 10/1998 |
| WO | 9929693 | 6/1999 |
| WO | 9965908 | 12/1999 |
| WO | 9965909 | 12/1999 |
| WO | 200047719 | 8/2000 |
| WO | 0198301 | 12/2001 |
| WO | 02051837 | 7/2002 |
| WO | 02089811 | 11/2002 |
| WO | 03025003 | 3/2003 |
| WO | 03076658 | 9/2003 |
| WO | 2004014368 | 2/2004 |
| WO | 2004016609 | 2/2004 |
| WO | 2004032829 | 4/2004 |
| WO | 2004032868 | 4/2004 |
| WO | 2004055024 | 7/2004 |
| WO | 2005003065 | 1/2005 |
| WO | 2005025616 | 3/2005 |
| WO | 2005044181 | 5/2005 |
| WO | 2005062795 | 7/2005 |
| WO | 2005097740 | 10/2005 |
| WO | 2005103050 | 11/2005 |
| WO | 2005121175 | 12/2005 |
| WO | 2005123079 | 12/2005 |
| WO | 2006004703 | 1/2006 |
| WO | 2006009832 | 1/2006 |
| WO | 2006036291 | 4/2006 |
| WO | 2006042102 | 4/2006 |
| WO | 2006045392 | 5/2006 |
| WO | 2006050976 | 5/2006 |
| WO | 2006052568 | 5/2006 |
| WO | 2006065280 | 6/2006 |
| WO | 2006069081 | 6/2006 |
| WO | 2006091568 | 8/2006 |
| WO | 2006118959 | 11/2006 |
| WO | 2006136924 | 12/2006 |
| WO | 2007063385 | 6/2007 |
| WO | 2007069053 | 6/2007 |
| WO | 2007076423 | 7/2007 |
| WO | 2007088450 | 8/2007 |
| WO | 2007088462 | 8/2007 |
| WO | 2007099423 | 9/2007 |
| WO | 2007104763 | 9/2007 |
| WO | 2007105053 | 9/2007 |
| WO | 2007124096 | 11/2007 |
| WO | 2007135380 | 11/2007 |
| WO | 2007138431 | 12/2007 |
| WO | 2007149798 | 12/2007 |
| WO | 2008070908 | 6/2008 |
| WO | 2008075007 | 6/2008 |
| WO | 2008091799 | 7/2008 |
| WO | 2008122789 | 10/2008 |
| WO | 2008128072 | 10/2008 |
| WO | 2008129152 | 10/2008 |
| WO | 2008150914 | 12/2008 |
| WO | 2008155000 | 12/2008 |
| WO | 2009005730 | 1/2009 |
| WO | 2009030270 | 3/2009 |
| WO | 2009035159 | 3/2009 |
| WO | 2009071620 | 6/2009 |
| WO | 2009127642 | 10/2009 |
| WO | 2009131687 | 10/2009 |
| WO | 2009134658 | 11/2009 |
| WO | 2010000364 | 1/2010 |

(56) References Cited

FOREIGN PATENT DOCUMENTS

| | | |
|---|---|---|
| WO | 2010003133 | 1/2010 |
| WO | 2010020308 | 2/2010 |
| WO | 2010026335 | 3/2010 |
| WO | 2010031988 | 3/2010 |
| WO | 2010036380 | 4/2010 |
| WO | 2010080712 | 7/2010 |
| WO | 2010081835 | 7/2010 |
| WO | 2010085799 | 7/2010 |
| WO | 2010093191 | 8/2010 |
| WO | 2010106333 | 9/2010 |
| WO | 2010109005 | 9/2010 |
| WO | 2010127754 | 11/2010 |
| WO | 2010129053 | 11/2010 |
| WO | 2010141817 | 12/2010 |
| WO | 2011038572 | 4/2011 |
| WO | 2011045344 | 4/2011 |
| WO | 2014060113 | 4/2011 |
| WO | 2011053861 | 5/2011 |
| WO | 2011055911 | 5/2011 |
| WO | 2011057204 | 5/2011 |
| WO | 2011060295 | 5/2011 |
| WO | 2011106168 | 9/2011 |
| WO | 2011131980 | 10/2011 |
| WO | 2011137022 | 11/2011 |
| WO | 2011141756 | 11/2011 |
| WO | 2011144622 | 12/2011 |
| WO | 2011147756 | 12/2011 |
| WO | 2011149827 | 12/2011 |
| WO | 2011151360 | 12/2011 |
| WO | 2012028629 | 3/2012 |
| WO | 2012034526 | 3/2012 |
| WO | 2012038743 | 3/2012 |
| WO | 2012058193 | 5/2012 |
| WO | 2012062783 | 5/2012 |
| WO | 2012075046 | 6/2012 |
| WO | 2012118679 | 9/2012 |
| WO | 2012131365 | 10/2012 |
| WO | 2012135631 | 10/2012 |
| WO | 2012143143 | 10/2012 |
| WO | 2012143144 | 10/2012 |
| WO | 2012159079 | 11/2012 |
| WO | 2012162254 | 11/2012 |
| WO | 2012178015 | 12/2012 |
| WO | 2013007768 | 1/2013 |
| WO | 2013046029 | 4/2013 |
| WO | 2013139882 | 9/2013 |
| WO | 2013164321 | 11/2013 |
| WO | 2013166276 | 11/2013 |
| WO | 2014001973 | 1/2014 |
| WO | 2014093383 | 6/2014 |
| WO | 2015022664 | 2/2015 |
| WO | 2015092592 | 6/2015 |

OTHER PUBLICATIONS

Banno, Tadashi, et al. "Some Applications of the Grignard Cross-Coupling Reaction in the Industrial Field", Journal of Organometallic Chemistry, Jul. 1, 2002, pp. 288-291, 653(1-2).

Boger, Dale, L., et al., "Thermal Cycloaddition of 1,3,5-Triazine with Enamines: Regiospecific Pyrimidine Annulation", Journal of Organic Chemistry, Jul. 1982, pp. 2673-2675, 47(13).

Bookser, B.C., et al., Adenosine Kinase Inhibitors. 6. Water Solubility and Antinociceptive Activity of 5-Phenyl-7-deoxay-beta-D-ribofuranosyl)pyrrolo[2,3-d]pyrimidines Substituted at C4 with Glycinamides and Related Compounds, Journal of Medicinal Chemistry, Dec. 1, 2005, pp. 7808-7820, 48(24).

Boyer, S.H., et al., "Adenosine Kinase Inhibitors, 5. Synthesis, Enzyme Inhibition, and Analgesic Activity of Diaryl-erythro-furanosyltubercidin Analogues", Journal of Medicinal Chemistry, Oct. 6, 2005, pp. 6430-6441, 48(20).

Caravatti, G., et al., "Pyrrolo[2,3-d]pyrimidine and Pyrazolo[3,4-d]pyrimidine Derivatives as Selective Inhibitors of the EFG Receptor Tyrosine Kinase", ACS Symposium Series, Aug. 24, 2001, pp. 231-244, Chapter 14, vol. 796.

Chebanov, V., et al., "Cyclocondensation reactions of 5-aminopyrazoles, pyruvic acids and aldehydes. Multicomponent approaches to pyrazolopyridines and related products", Tetrahedron, 2007, pp. 1229-1242, 63(5).

Chen, Gang, et al., "Elucidating inhibitory models of the inhibitors of epidermal growth factor receptor by docking and 3D-QSAR", Bioorganic & Medicinal Chemistry, 2004, pp. 2409-2417, 12(9).

Chen, H., et al., "Discovery of Selective LRRK2 Inhibitors Guided by Computational Analysis and Molecular Modeling", Journal of Medicinal Chemistry, 2012, pp. 5536-5545, vol. 55.

Chen, Xiu-Mei, et al., "Structure-based and shape-complemented pharmacophore modeling for the discovery of novel checkpoint kinase 1 inhibitors", Journal of Molecular Modeling, 2010, pp. 1195-1204, 16(7).

Coumar, Mohane S., et al., "Identification, SAR Studies, and X-ray Co-crystallographic Analysis of a Novel Furanopyrimidine Aurora Kinase A Inhibitor", ChemMedChem, 2010, pp. 255-267, 5(2).

Erdik, Ender, "Transition Metal Catalyzed Reactions of Organozinc Reagents", Tetrahedron, 1992, pp. 9577-9648, 18(44).

Finnin, Barrie C., et al., "Transdermal Penetration Enhancers: Applications, Limitations, and Potential", The Journal of Pharmaceutical Sciences, Oct. 1999, pp. 955-958, 88(10).

Foloppe, N., et al., "Structure-Based Design of Novel Chk1 Inhibitors: Insights into Hydrogen Bonding and Protein-Ligand Affinity", Journal of Medicinal Chemistry, 2005, pp. 4332-4345, 48(13).

Gangloff, Anthony R., et al., "Synthesis of 3,5-disubstituted-1,2,4-oxadiazoles using tetrabutylammonium fluoride as mild and efficient catalyst", Tetrahedron Letters, Feb. 19, 2001, pp. 1441-1443, 42(8).

Gillardon, F., et al., "Parkinson's Disease-Linked Leucine-Rich Repeat Kinase 2(R1331G) Mutation Increases Proinflammatory Cytokine Release From Activated Primary Microglial Cells and Resultant Neurotoxicity", Neuroscience, Apr. 19, 2012, pp. 41-48, vol. 208.

Glenner, George G., et al., "Amyloidosis of the Nervous System", The Journal of Neurological Sciences, 1989, pp. 1-28, 94(1-3).

Haan, J., et al., "Amyloid in Central Nervous System Disease", Clinical Neurology and Neurosurgery, 1990, pp. 305-310, 92(4).

Haleblain, John, "Characterization of Habits and Crystalline Modification of Solids and Their Pharmaceutical Applications", The Journal of Pharmaceutical Sciences, Aug. 1975, pp. 1269-1288, 64(8).

International Patent Application PCT/IB2013/055039, filed Jun. 19, 2013, International Search Report, mailed Oct. 14, 2013, 9 pages.

International Patent Application PCT/IB2013/055039, filed Jun. 19, 2013, Written Opinion of the International Searching Authority, mailed Oct. 14, 2013, 10 pages.

International Patent Application PCT/IB2014/066563 Written Opinion & Search Report, mailed Feb. 24, 2015, 10 pages.

Jorgensen, A., et al., "Synthesis of 7H-Pyrrolo[2,3-d]pyrimidin-4-amines", Liebigs Annalen Der Chemie, Jan. 1, 1985, pp. 142-148, vol. 1985.

Joshi, K., et al., "Synthesis of some new fluorine-containing 5-amino-1, 3-disubstituted pyrazoles and 1H-pyrazolo [3,4-b]pyridines", Journal of Heterocyclic Chemistry, Sep. 1979, pp. 1141-1145, 16(6).

KR20100116765, Korean Patent, published Nov. 2, 2010, Machine Translation.

KR20120019785, Korean Patent, published Mar. 3, 2007, Machine Translation.

Lewis, Patrick, et al., "LRRK2 and Human Disease: A Complicated Question or a Question of Complexes?", Science Signaling, Jan. 17, 2012, pp. pe2, 5(207).

Littke, Adam F., et al., "Versatile Catalysts for the Suzuki Cross-Coupling of Arylboronic Acids with Aryl and Vinyl Halides and Triflates under Mild Conditions", Journal of American Chemical Society, May 3, 2000, pp. 4020-4028, 122 (17).

Liu, Zhihua, et al., "The Kinase LRRK2 is a Regulator of the Transcription Factor NFAT That Modulates the Severity of Inflammatory Bowel Disease", Nature Immunology, 2011, pp. 1063-1070, 12(11).

(56) References Cited

OTHER PUBLICATIONS

Miyaura, Norio, et al., "Palladium-Catalyzed Cross-Coupling Reactions of Organoboron Compounds", Chemistry Review, 1995, pp. 2457-2483, 95(7).
Moehle, Mark S., et al., "LRRK2 Inhibition Attenuates Microglial Inflammatory Responses", The Journal of Neuroscience, Feb. 1, 2012, pp. 1602-1611, 32(5).
Peng, Tao, et al., 3D-QSAR and Receptor Modeling of Tyrosine Kinase Inhibitors with Flexible Atom Receptor Model (FLARM), Journal of Chemical Information and Computer Sciences, 2003, pp. 298-303, 43(1).
Peng, Tao, et al., "Flexible Atom Receptor Model Study on Tyrosine Kinase Inhibitors", Acta Chim. Sinica, 2003, pp. 29-33, 61(1), Abstract.
Peng, Tao, et al., "Pharmacophore Analysis of Epidermal Growth Factor Receptor Tyrosine Kinase Inhibitors", Institute of Process Engineering, Chinese Academy of Science, 2003, pp. 430-434, 61(3), Abstract.
Quiroga, J., et al., "A hydrogen-bonded dimer in 6-(4-bromophenyl)-3-methyl-1-phenyl-4,5-dihydro-1H-pyrazolo[3,4-b]pyridine and a chain of rings built from n-H . . . N and C-H . . . π(pyridine)hydrogen bonds in 3-(4-nitrophenyl)-4-phenyl-1H-pyrazolo[3,4-13]pyridine", Acta Crystallographica Sections C, Crystal Structure Communications, 2010, pp. o163-o167, 66(4).
Quiroga, J., et al., "Synthesis and Structural Analysis of 5-Cyanoldihydropyrazolo[3,4-b]pyridines", Journal of Heterocyclic Chemistry, Jan.-Feb. 2001, pp. 53-60, 38(1).
Quiroga, J., et al., "Three 3-aryl-5-cyanopyrazolo[3,4-b]pyridines", Acta Crystallographica, Section C: Crystal Structure Communications, 1999, iii, IUC9900168/1-3, C55(12).
Reader, John C., et al., "Structure-Guided Evolution of Potent and Selective CHK1 Inhibitors through Scaffold Morphing", Journal of Medicinal Chemistry, 2011, pp. 8328-8242, 54(24).
Saleh, T., et al., "Ultrasound assisted one-pot, three-components synthesis of pyrimido[1,2-a]benzimidazoles and pyrazolol[3,4-b]pyridines: A New access via phenylsulfone synthon", Ultrasonics Sonochemistry, 2012, pp. 49-55, 19 (1).
Sanz, Roberto, et al., "Regioselective Synthesis of 4- and 7-Alkoxyindoles from 2,3-Dihalophenols Application to the Preparation of Indole Inhibitors of Phospholipase A2", Journal of Organic Chemistry, Mar. 28, 2007, pp. 5113-5118, 72(14).
Saunder-Pullman, Rachel, et al., "LRRK2 G20195 Mutations are Associated with an Increased Cancer Risk in Parkinson Disease", Movement Disorders, 2010, pp. 2536-2541, 25(15).
Shie, Jiun-Jie, et al., "Microwave-Assisted One-Pot Tandem Reactions for Direct Conversion of Primary Alcohols and Aldehydes to Triazines and Tetrazoles in Aqueous Media", Journal of Organic Chemistry, Apr. 13, 2007, pp. 3141-3144, 72(8).
Singapore Patent Application No. 11201408044Q, Search Report and Written Opinion, mailed Jan. 5, 2016, 10 pages.
Singh, S.P., et al., "Synthesis of Some Novel Fluorinated Pyrazolo[3,4-b]Pyridines", Synthetic Communications, 2004, pp. 4359-4367, 34(23).
Suzuki, Akira, "Recent Advances in the Cross-Coupling Reactions of Organoboron Derivatives with Organic Electrophiles, 1995-1998", Journal of Organometallic Chemistry, Mar. 15, 1999, pp. 147-168, 576(1-2).
Taiwan Patent Application No. 102122705 Office Action including Search Report dated Jul. 3, 1014, 12 pages.
Taylor, E.C., et al., "Synthesis of 4-Amino-5-cyanopyrrolo[2,3-d]pyrimidine, the Agycone of Toyocamycin", Journal of the American Chemical Society, May 1, 1964, pp. 951-952, 86(5).
Taylor, Edward C., et al., "Synthesis of Pyrrolo[2,3-d]pyrimidines. The Aglycone of Toycamycin", Journal of the American Chemical Society, 1965, pp. 1995-2003, 87(9).
Traxler, P.M., et al., "4-(Phenylamino)pyrrolopyrimidines: Potent and Selective ATP Site Directed Inhibitors of the EGF-Receptor Protein Tyrosine Kinase", Journal of Medicinal Chemistry, Jun. 1, 1996, pp. 2285-2292, 39(12).
Ugarkar, B.G., et al., "Adenosine Kinase Inhibtors, 2. Synthesis, Enzymen Inhibition and Antiseizure Acitivity of Diaryltubercidin Analogues", Journal of Medicinal Chemistry, Jul. 27, 2000, pp. 2894-2905, 43(15).
Wempen, Iris, et al., "Pyrimidines. II. Synthesis of 6-Fluorouracil", Journal of Medicinal Chemistry, 1964, pp. 207-209, 7(2).
Wilder, L, et al., "7-Alkyl and 7-Cycloalkyl-5-aryl-pyrrolo[2,3-d]pyrimidines-Potent Inhibitors of the Tyrosine Kinase c-Src", Bioorganic and Medicinal Chemistry, Mar. 26, 2001, pp. 849-852, vol. 11.
Wu, T., et al., "One-Pot, Two-Step Microwave-Assisted Reaction in Constructing 4,5-Disubstituted Pyrazolopyrimidines", Organic Letters, Jun. 9, 2003, pp. 3587-3590, 5(20).
Zahran, M. A., et al., "Synthesis and Reactions of 2-Deoxy-β-D-ribofuranosyl Derivatives of 3-Aryl-4H-pyrrolo[2,3-d] pyrimidin-4-imines", Monatshefte fur Chemie, 1995, pp. 1271-1277, 126(11).
Zhao, Yi., et al., "LRRK2 Variant Associated with Alzheimer's Disease", Neurobiology of Aging, 2011, pp. 1990-1993, vol. 32.
Zimprich, Alexander, et al., "Mutations in LRRK2 Cause Autosomal-Dominant Parkinsonism with Pleomorphic Pathology", Neuron, Nov. 18, 2004, pp. 601-607, 44(4).

3,4-DISUBSTITUTED-1 H-PYRROLO[2,3-B]PYRIDINES AND 4,5-DISUBSTITUTED-7H-PYRROLO[2,3-C]PYRIDAZINES AS LRRK2 INHIBITORS

This application is a national stage application under 35 U.S.C. 371 of PCT/IB2014/066563, filed on Dec. 3, 2014, which claims the benefit of U.S. Provisional Patent Application No. 61/916,953, filed on Dec. 17, 2013, the disclosures of which are hereby incorporated by reference in their entirety.

FIELD OF THE INVENTION

The present invention relates to small molecule inhibitors of leucine-rich repeat kinase 2 (LRRK2). This invention also relates to methods of inhibiting, in mammals, including humans, LRRK2 by administration of the small molecule LRRK2 inhibitors. The present invention also relates to the treatment of Parkinson's Disease (PD) and other neurodegenerative and/or neurological disorders in mammals, including humans with the LRRK2 inhibitors. More particularly, this invention relates to 3,4-disubstituted-1H-pyrrolo [2,3-b]pyridine derivatives and 4,5-disubstituted-7H-pyrrolo[2,3-c]pyridazine compounds useful for the treatment of neurodegenerative and/or neurological disorders, such as PD, Alzheimer's Disease (AD) and other LRRK2 associated disorders.

BACKGROUND OF THE INVENTION

LRRK2 is a 286 kDa protein in the ROCO protein family with a complex multidomain structure. Protein motifs that have been established for LRRK2 include an armadillo-like (ARM) domain, an ankyrin-like (ANK) domain, a leucine-rich repeat (LRR) domain, a Ras (renin-angiotensin system) of complex (ROC) domain, a C-terminal of ROC (COR) domain, a kinase domain, and a C-terminal WD40 domain. The ROC domain binds guanosine triphosphate (GTP) and the COR domain may be a regulator of the ROC domain's GTPase activity. The kinase domain has structural homology to the MAP kinase kinase kinases (MAPKKK) and has been shown to phosphorylate a number of cellular proteins in vitro, but the endogenous substrate has yet to be determined. LRRK2 has been found in various regions of the brain as well as in a number of peripheral tissues including heart, lung, spleen, and kidney.

LRRK2 has the ability to potentially play a complex role in multiple cellular processes as a consequence of its multi-domain construct, each associated with putative protein-protein interactions, guanosine triphosphatase (GTPase) activity, and kinase activity. For example, LRRK2 has been associated with NFAT inhibition in the immune system and has been linked to vesicle trafficking, presynaptic homeostasis, mammalian target of rapamycin (mTOR) signaling, signaling through the receptor tyrosine kinase MET in papillary renal and thyroid carcinomas, cytoskeletal dynamics, the mitogen-activated protein kinase (MAPK) pathway, the tumor necrosis factor-α (TNF-α) pathway, the Wnt pathway and autophagy. Recent genome-wide association (GWA) genetic studies have implicated LRRK2 in the pathogenesis of various human diseases such as PD, inflammatory bowel disease (Crohn's disease), cancer and leprosy (Lewis, P. A. and Manzoni, C. Science Signaling 2012, 5(207), pe 2).

Parkinson's disease (PD) is a relatively common age-related neurodegenerative disorder resulting from the progressive loss of dopamine-producing neurons and which affects up to 4% of the population over age 80. PD is characterized by both motor symptoms, such as tremor at rest, rigidity, akinesia and postural instability as well as non-motor symptoms such as impairment of cognition, sleep and sense of smell. GWA studies have linked LRRK2 to PD and many patients with point mutations in LRRK2 present symptoms that are indistinguishable from those with idiopathic PD. Over 20 LRRK2 mutations have been associated with autosomal-dominant parkinsonism, and the R1441C, R1441G, R1441H, Y1699C, G2019S, 12020T and N1437H missense mutations are considered to be pathogenic. The LRRK2 R1441G mutation has been shown to increase the release of proinflammatory cytokines (higher levels of TNF-α, IL-1β, IL-12 and lower levels of IL-10) in microglial cells from transgenic mice and thus may result in direct toxicity to neurons (Gillardon, F. et al. Neuroscience 2012, 208, 41-48). In a murine model of neuroinflammation, induction of LRRK2 in microglia was observed and inhibition of LRRK2 kinase activity with small molecule LRRK2 inhibitors (LRRK2-IN-1 or sunitinib) or LRRK2 knockout resulted in attenuation of TNF-α secretion and nitric oxide synthase (iNOS) induction (Moehle, M. et al. J. Neurosci. 2012, 32(5), 1602-1611). The most common of the LRRK2 mutations, G2019S, is present in more than 85% of PD patients carrying LRRK2 mutations. This mutation, which is present in the LRRK2 kinase domain, leads to an enhancement of LRRK2 kinase activity. In the human brain LRRK2 expression is highest in the same regions of the brain that are impacted by PD, and LRRK2 is found in Lewy Bodies, a hallmark of PD. Recent studies indicate that a potent, selective, brain-penetrant kinase inhibitor for LRRK2 could be a therapeutic treatment for PD.

Dementia results from a wide variety of distinctive pathological processes. The most common pathological processes causing dementia are AD, cerebral amyloid angiopathy (CM) and prion-mediated diseases (see, e.g., Haan et al., Clin. Neurol. Neurosurg. 1990, 92(4):305-310; Glenner et al., J. Neurol. Sci. 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050. LRRK2 mutations have been associated with AD-like pathology, which suggests that there may be a partial overlap between the neurodegenerative pathways in both AD and PD (Zimprach, A. et al. Neuron 2004, 44, 601-607). In addition, the LRRK2 R1628P variant (COR domain) has been associated with an increased incidence of AD in a certain population, perhaps resulting from increased apoptosis and cell death (Zhao, Y. et al.; Neurobiology of Aging 2011, 32, 1990-1993.

An increased incidence of certain non-skin cancers such as renal, breast, lung and prostate cancers, as well as acute myelogenous leukemia (AML), has been reported in Parkinson's disease patients with the LRRK2 G2019S mutation (Saunders-Pullman, R. et al.; Movement Disorders, 2010, 25(15), 2536-2541). Since the G2019S mutation is associated with increased LRRK2 kinase activity, inhibition of this activity may be useful in the treatment of cancer, such as kidney, breast, lung, prostate and blood cancers.

Inflammatory bowel disease (IBD) or Crohn's disease (CD) is a complex disease and is believed to result from an inappropriate immune response to microbiota in the intestinal tract. GWA studies have recently identified LRRK2 as a major susceptibility gene for Crohn's disease, particularly the M2397T polymorphism in the WD40 domain (Liu, Z. et al. Nat. Immunol. 2011, 12, 1063-1070). In a recent study LRRK2 deficient mice were found to be more susceptible to dextran sodium sulfate induced colitis than their wild-type counterparts, indicating that LRRK2 may play a role in the pathogenesis of IBD (Liu, Z. and Lenardo, M.; Cell Research 2012, 1-3).

Both non-selective and selective small molecule compounds with LRRK2 inhibitory activity such as staurosporine, sunitinib, LRRK2-IN-1, CZC-25146, TAE684 and those in WO 2011/141756, WO 2012/028629 and WO 2012/058193 have been described. It is desirable to provide compounds which are potent and selective inhibitors of LRRK2 with a favorable pharmacokinetic profile and the ability to traverse the blood brain barrier. Accordingly, the present invention is directed to novel 3,4-disubstituted-1H-pyrrolo[2,3-b]pyridine and 4,5-disubstituted-7H-pyrrolo[2,3-c]pyridazine compounds with LRRK2 inhibitory activity and the use of these compounds in the treatment of diseases associated with LRRK2, such as neurodegenerative diseases, including PD.

SUMMARY OF THE INVENTION

A first embodiment of a first aspect of the present invention is a compound of Formula

I

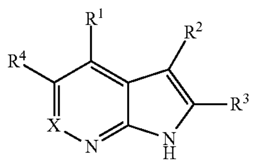

or a pharmaceutically acceptable salt thereof wherein

X is N or $CR^5$;

$R^1$ is selected from the group consisting of —$NR^6R^7$, $C_3$-$C_7$cycloalkyl, phenyl, five to ten membered heteroaryl which contains one to four heteroatoms independently selected from N, O and S, four to seven membered heterocycloalkyl which contains one to three heteroatoms independently selected from N, O and S and wherein the heterocycloalkyl is attached at a ring carbon atom, and four to seven membered heterocycloalkenyl which contains one to three heteroatoms independently selected from N, O and S and wherein the heterocycloalkenyl is attached at a ring carbon atom; wherein the $C_3$-$C_7$cycloalkyl, phenyl, five to ten membered heteroaryl, four to seven membered heterocycloalkyl and four to seven membered heterocycloalkenyl are optionally substituted with one to three $R^8$;

$R^2$ is phenyl or a five to ten membered heteroaryl which contains one to four heteroatoms independently selected from N, O and S; wherein the phenyl and five to ten membered heteroaryl are optionally substituted with one to three $R^9$ and wherein the phenyl is optionally fused with a $C_5$-$C_6$cycloalkyl or a five to six membered heterocycloalkyl which contains one to three heteroatoms selected from N, O and S and which is optionally substituted with oxo;

$R^3$ is hydrogen, halo or $C_1$-$C_3$alkyl;

$R^4$ is hydrogen, cyano, —$CO_2$($C_1$-$C_3$alkyl) or $C_1$-$C_3$alkyl which is optionally substituted with a hydroxy, $C_1$-$C_3$alkoxy or cyano;

$R^5$ is hydrogen or $C_1$-$C_3$alkyl;

$R^6$ and $R^7$ are each independently hydrogen, $C_1$-$C_6$alkyl, $C_3$-$C_7$cycloalkyl, a four to seven membered heterocycloalkyl which contains one to three heteroatoms independently selected from N, O and S; or a five to six membered heteroaryl which contains one to four heteroatoms independently selected from N, O and S, wherein the $C_1$-$C_6$alkyl, $C_3$-$C_7$cycloalkyl, four to seven membered heterocycloalkyl, or five to six membered heteroaryl are optionally substituted with one to three $R^{10}$;

or $R^6$ and $R^7$ taken together with the nitrogen to which they are attached are a four to seven membered heterocycloalkyl which optionally contains one to two additional heteroatoms independently selected from N, O and S; or a six to twelve membered heterobicycloalkyl which optionally contains one to two additional heteroatoms independently selected from N, O and S; and wherein the four to seven membered heterocycloalkyl or six to eleven membered heterobicycloalkyl is optionally substituted with one to three $R^{10}$;

$R^8$, $R^9$ and $R^{10}$ at each occurrence are independently selected from $C_1$-$C_3$alkyl optionally substituted with one to three halo, hydroxy, $C_1$-$C_3$alkoxy or cyano, $C_1$-$C_3$alkoxy, hydroxy, halo, cyano, —$NR^aR^b$, —C(O)$NR^aR^b$, —$S(O)_2NR^aR^b$, or a five to six membered heteroaryl which contains one to three heteroatoms independently selected from N, O and S and which is optionally substituted with a $C_1$-$C_3$alkyl; and $R^a$ and $R^b$ at each occurrence are each independently hydrogen, $C_1$-$C_6$alkyl, $C_3$-$C_7$cycloalkyl or —C(O)$C_1$-$C_6$alkyl.

A second embodiment of the first aspect of the present invention is the compound of the first embodiment or a pharmaceutically acceptable salt thereof, wherein $R^3$ is hydrogen, chloro or methyl; $R^4$ is hydrogen, cyano, hydroxymethyl, methoxymethyl, cyanomethyl or —$C(O)_2CH_3$; and $R^5$ is hydrogen or methyl.

A third embodiment of the first aspect of the present invention is the compound of the second embodiment or a pharmaceutically acceptable salt thereof, wherein $R^1$ is —$NR^6R^7$; and $R^6$ and $R^7$ taken together with the nitrogen to which they are attached are pyrrolidin-1-yl, piperidin-1-yl, morpholin-4-yl, thiomorpholin-4-yl, 1,4-oxazepan-4-yl, 6-oxa-3-aza-bicyclo[3.1.1]heptan-3-yl or 8-oxa-3-aza-bicyclo[3.2.1]octan-3-yl; each of which is optionally substituted with one to three $R^8$.

A fourth embodiment of the first aspect of the present invention is the compound of the third embodiment or a pharmaceutically acceptable salt thereof, wherein $R^6$ and $R^7$ taken together with the nitrogen to which they are attached are morpholin-4-yl optionally substituted with a methyl.

A fifth embodiment of the first aspect of the present invention is the compound of the third embodiment or a pharmaceutically acceptable salt thereof, wherein $R^6$ and $R^7$ taken together with the nitrogen to which they are attached are pyrrolidinyl or piperidinyl, each optionally substituted with one to two $R^8$; and each $R^6$ is independently selected from fluoro, hydroxy, methyl, hydroxymethyl, methoxy and methoxymethyl.

A sixth embodiment of the first aspect of the present invention is the compound of the second embodiment or a pharmaceutically acceptable salt thereof, wherein $R^1$ is a five to ten membered heteroaryl which contains one to four heteroatoms independently selected from N, O and S and is optionally substituted with one to two $R^8$, wherein the five to ten membered heteroaryl is selected from pyrazolyl, furanyl, pyridinyl and benzothiazolyl.

A seventh embodiment of the first aspect of the present invention is the compound of the second embodiment or a pharmaceutically acceptable salt thereof, wherein $R^1$ is phenyl optionally substituted with one to two $R^8$; and each $R^8$ is independently selected from fluoro, methoxy, methoxymethyl, cyano, cyanomethyl, —C(O)$NR^aR^b$, —S$(O)_2NR^aR^b$ and 5-methyl-1,3,4-oxadiazol-2-yl.

An eighth embodiment of the first aspect of the present invention is the compound of the second embodiment or a pharmaceutically acceptable salt thereof, wherein $R^1$ is $C_3$-$C_7$cycloalkyl optionally substituted with one to two $R^8$.

A ninth embodiment of the first aspect of the present invention is the compound of any one of the first through eighth embodiments or a pharmaceutically acceptable salt thereof, wherein X is $CR^5$.

A tenth embodiment of the first aspect of the present invention is the compound of any one of the first through eighth embodiments or a pharmaceutically acceptable salt thereof, wherein X is N.

An eleventh embodiment of the first aspect of the present invention is the compound of the second embodiment or a pharmaceutically acceptable salt thereof wherein $R^1$ is —$NR^6R^7$; $R^6$ and $R^7$ taken together with the nitrogen to which they are attached is selected from the group consisting of:

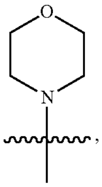, 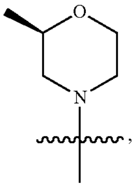, 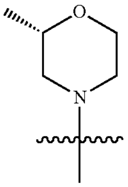, 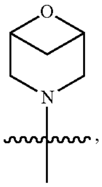,

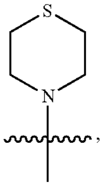, 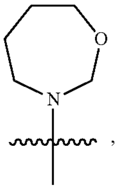, and 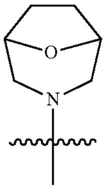;

$R^2$ is phenyl, pyrrolyl, pyrazolyl, imidazolyl, pyridinyl, pyridonyl or imidazo[1,2-b]pyridazinyl, each optionally substituted with one to three $R^9$; and $R^9$ at each occurrence is independently selected from chloro, fluoro, cyano, methyl, methoxy, hydroxymethyl and —C(O)$NH_2$.

A twelfth embodiment of the first aspect of the present invention is the compound of the eleventh embodiment or a pharmaceutically acceptable salt thereof wherein $R^6$ and $R^7$ taken together with the nitrogen to which they are attached is

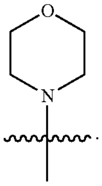.

A thirteenth embodiment of the first aspect of the present invention is the compound of any one of the first through eighth embodiments or a pharmaceutically acceptable salt thereof wherein $R^2$ is phenyl, pyrrolyl, pyrazolyl, imidazolyl, pyridinyl, pyridonyl or imidazo[1,2-b]pyridazinyl; each optionally substituted with one to three $R^9$; and $R^9$ at each occurrence is independently selected from chloro, fluoro, cyano, methyl, methoxy, hydroxymethyl and —C(O)$NH_2$.

A fourteenth embodiment of the first aspect of the present invention is the compound of the third embodiment or a pharmaceutically acceptable salt thereof wherein $R^6$ and $R^7$ taken together with the nitrogen to which they are attached are pyrrolidin-1-yl or piperidin-1-yl; each of which is optionally substituted with one to two $R^8$; $R^8$ at each occurrence is independently selected from fluoro, methyl, methoxy, methoxymethyl, hydroxy or hydroxymethyl.

A fifteenth embodiment of the first aspect of the present invention is a compound according to the first embodiment selected from the group consisting of:

3-[4-(morpholin-4-yl)-1H-pyrrolo[2,3-b]pyridin-3-yl]benzonitrile;
2-fluoro-3-[4-(morpholin-4-yl)-1H-pyrrolo[2,3-b]pyridin-3-yl]benzonitrile;
3-[4-(morpholin-4-yl)-1H-pyrrolo[2,3-b]pyridin-3-yl]imidazo[1,2-b]pyridazine;
1-methyl-4-[4-(morpholin-4-yl)-1H-pyrrolo[2,3-b]pyridin-3-yl]-1H-pyrrole-2-carbonitrile;
1-methyl-4-[4-(morpholin-4-yl)-1H-pyrrolo[2,3-b]pyridin-3-yl]-1H-imidazole-2-carbonitrile;
1-methyl-4-[4-(morpholin-4-yl)-7H-pyrrolo[2,3-c]pyridazin-5-yl]-1H-pyrrole-2-carbonitrile;
4-[2-chloro-4-(morpholin-4-yl)-1H-pyrrolo[2,3-b]pyridin-3-yl]-1-methyl-1H-pyrrole-2-carbonitrile;
3-[2-methyl-4-(morpholin-4-yl)-1H-pyrrolo[2,3-b]pyridin-3-yl]benzonitrile;
3-[6-methyl-4-(morpholin-4-yl)-1H-pyrrolo[2,3-b]pyridin-3-yl]benzonitrile;
3-[5-(hydroxymethyl)-4-(morpholin-4-yl)-1H-pyrrolo[2,3-b]pyridin-3-yl]benzonitrile;
3-(3-cyanophenyl)-4-(morpholin-4-yl)-1H-pyrrolo[2,3-b]pyridine-5-carbonitrile;
4-(3,6-dihydro-2H-pyran-4-yl)-3-(1-methyl-1H-pyrazol-4-yl)-1H-pyrrolo[2,3-b]pyridine;
3-(1-methyl-1H-pyrazol-4-yl)-4-(morpholin-4-yl)-1H-pyrrolo[2,3-b]pyridine;
3-(3-cyano-2-fluorophenyl)-4-(dimethylamino)-1H-pyrrolo[2,3-b]pyridine-5-carbonitrile;
3-(5-fluoro-2-methoxyphenyl)-4-(morpholin-4-yl)-1H-pyrrolo[2,3-b]pyridine;
3-(3-fluoro-5-methoxyphenyl)-4-(morpholin-4-yl)-1H-pyrrolo[2,3-b]pyridine;
2-methyl-3-(1-methyl-1H-pyrazol-4-yl)-4-(morpholin-4-yl)-1H-pyrrolo[2,3-b]pyridine;
2-fluoro-3-[6-methyl-4-(morpholin-4-yl)-1H-pyrrolo[2,3-b]pyridin-3-yl]benzonitrile;
6-[4-(morpholin-4-yl)-1H-pyrrolo[2,3-b]pyridin-3-yl]pyridine-2-carbonitrile;
3-(3-chlorophenyl)-4-(morpholin-4-yl)-1H-pyrrolo[2,3-b]pyridine;
3-(3-chloro-5-fluorophenyl)-4-(morpholin-4-yl)-1H-pyrrolo[2,3-b]pyridine;
3-(2,5-difluorophenyl)-4-(morpholin-4-yl)-1H-pyrrolo[2,3-b]pyridine;
3-(2-chlorophenyl)-4-(morpholin-4-yl)-1H-pyrrolo[2,3-b]pyridine;
3-(2,3-difluorophenyl)-4-(morpholin-4-yl)-1H-pyrrolo[2,3-b]pyridine;

3-(3-fluorophenyl)-4-(morpholin-4-yl)-1H-pyrrolo[2,3-b]pyridine;
3-(2-fluorophenyl)-4-(morpholin-4-yl)-1H-pyrrolo[2,3-b]pyridine;
3-(5-chloro-2-fluorophenyl)-4-(morpholin-4-yl)-1H-pyrrolo[2,3-b]pyridine;
{3-[4-(morpholin-4-yl)-1H-pyrrolo[2,3-b]pyridin-3-yl]phenyl}methanol;
{4-fluoro-3-[4-(morpholin-4-yl)-1H-pyrrolo[2,3-b]pyridin-3-yl]phenyl}methanol;
3-[3-(5-methyl-1,3,4-oxadiazol-2-yl)phenyl]-4-(morpholin-4-yl)-1H-pyrrolo[2,3-b]pyridine;
3-(3-methoxyphenyl)-4-(morpholin-4-yl)-1H-pyrrolo[2,3-b]pyridine;
3-(3-chloro-2-fluorophenyl)-4-(morpholin-4-yl)-1H-pyrrolo[2,3-b]pyridine;
4-(morpholin-4-yl)-3-(2,3,5-trifluorophenyl)-1H-pyrrolo[2,3-b]pyridine;
3-(3,5-difluorophenyl)-4-(morpholin-4-yl)-1H-pyrrolo[2,3-b]pyridine;
3-(2-chloropyridin-3-yl)-4-(morpholin-4-yl)-1H-pyrrolo[2,3-b]pyridine;
4-(morpholin-4-yl)-3-phenyl-1H-pyrrolo[2,3-b]pyridine;
3-(2,4-difluorophenyl)-4-(morpholin-4-yl)-1H-pyrrolo[2,3-b]pyridine;
3-(3-fluoro-5-methylphenyl)-4-(morpholin-4-yl)-1H-pyrrolo[2,3-b]pyridine;
3-fluoro-5-[4-(morpholin-4-yl)-1H-pyrrolo[2,3-b]pyridin-3-yl]benzonitrile;
3-(2,3-difluoro-6-methoxyphenyl)-4-(morpholin-4-yl)-1H-pyrrolo[2,3-b]pyridine;
2-fluoro-5-[4-(morpholin-4-yl)-1H-pyrrolo[2,3-b]pyridin-3-yl]benzonitrile;
3-(5-methoxypyridin-3-yl)-4-(morpholin-4-yl)-1H-pyrrolo[2,3-b]pyridine;
6-[2-methyl-4-(morpholin-4-yl)-1H-pyrrolo[2,3-b]pyridin-3-yl]pyridine-2-carbonitrile;
3-(1-methyl-1H-pyrazol-4-yl)-4-(morpholin-4-yl)-1H-pyrrolo[2,3-b]pyridine-5-carbonitrile;
3-(3-cyano-2-fluorophenyl)-4-(morpholin-4-yl)-1H-pyrrolo[2,3-b]pyridine-5-carbonitrile;
3-(3-fluoro-5-methylphenyl)-4-(morpholin-4-yl)-1H-pyrrolo[2,3-b]pyridine-5-carbonitrile;
4-fluoro-3-[4-(morpholin-4-yl)-1H-pyrrolo[2,3-b]pyridin-3-yl]benzonitrile;
3-fluoro-4-[4-(morpholin-4-yl)-1H-pyrrolo[2,3-b]pyridin-3-yl]benzonitrile;
3-(hydroxymethyl)-5-[4-(morpholin-4-yl)-1H-pyrrolo[2,3-b]pyridin-3-yl]benzonitrile;
3-(4-fluorophenyl)-4-(morpholin-4-yl)-1H-pyrrolo[2,3-b]pyridine;
2-methyl-3-(5-methylpyridin-3-yl)-4-(morpholin-4-yl)-1H-pyrrolo[2,3-b]pyridine;
3-(3-chlorophenyl)-2-methyl-4-(morpholin-4-yl)-1H-pyrrolo[2,3-b]pyridine;
2-methyl-4-(morpholin-4-yl)-3-phenyl-1H-pyrrolo[2,3-b]pyridine;
3-(2-fluorophenyl)-2-methyl-4-(morpholin-4-yl)-1H-pyrrolo[2,3-b]pyridine;
3-(3-fluorophenyl)-2-methyl-4-(morpholin-4-yl)-1H-pyrrolo[2,3-b]pyridine;
3-fluoro-5-[2-methyl-4-(morpholin-4-yl)-1H-pyrrolo[2,3-b]pyridin-3-yl]benzonitrile;
1-[3-(1-methyl-1H-pyrazol-4-yl)-1H-pyrrolo[2,3-b]pyridin-4-yl]piperidin-3-ol;
4-[(2S)-2-methylmorpholin-4-yl]-3-(1-methyl-1H-pyrazol-4-yl)-1H-pyrrolo[2,3-b]pyridine;

4-(3,3-difluoropiperidin-1-yl)-3-(1-methyl-1H-pyrazol-4-yl)-1H-pyrrolo[2,3-b]pyridine;
{1-[3-(1-methyl-1H-pyrazol-4-yl)-1H-pyrrolo[2,3-b]pyridin-4-yl]piperidin-3-yl}methanol;
3-(1-methyl-1H-pyrazol-4-yl)-4-(8-oxa-3-azabicyclo[3.2.1]oct-3-yl)-1H-pyrrolo[2,3-b]pyridine;
N,N-dimethyl-3-(1-methyl-1H-pyrazol-4-yl)-1H-pyrrolo[2,3-b]pyridin-4-amine;
3-(1-methyl-1H-pyrazol-4-yl)-4-(thiomorpholin-4-yl)-1H-pyrrolo[2,3-b]pyridine;
4-(3,3-difluoropyrrolidin-1-yl)-3-(1-methyl-1H-pyrazol-4-yl)-1H-pyrrolo[2,3-b]pyridine;
3-[4-(3,6-dihydro-2H-pyran-4-yl)-1H-pyrrolo[2,3-b]pyridin-3-yl]benzonitrile;
3-[4-(3-hydroxypiperidin-1-yl)-1H-pyrrolo[2,3-b]pyridin-3-yl]benzonitrile;
3-{4-[2-(methoxymethyl)morpholin-4-yl]-1H-pyrrolo[2,3-b]pyridin-3-yl}benzonitrile;
4-(morpholin-4-yl)-3-(1H-pyrazol-4-yl)-1H-pyrrolo[2,3-b]pyridine;
3-[4-(1,4-oxazepan-4-yl)-1H-pyrrolo[2,3-b]pyridin-3-yl]benzonitrile;
3-[4-(4-hydroxypiperidin-1-yl)-1H-pyrrolo[2,3-b]pyridin-3-yl]benzonitrile;
3-[4-(3-methoxypiperidin-1-yl)-1H-pyrrolo[2,3-b]pyridin-3-yl]benzonitrile;
3-[4-(6-oxa-3-azabicyclo[3.1.1]hept-3-yl)-1H-pyrrolo[2,3-b]pyridin-3-yl]benzonitrile;
3-{4-[(3R,4R)-3,4-difluoropyrrolidin-1-yl]-1H-pyrrolo[2,3-b]pyridin-3-yl}benzonitrile;
3-[4-(4-fluoropiperidin-1-yl)-1H-pyrrolo[2,3-b]pyridin-3-yl]benzonitrile;
3-{4-[(3R)-3-fluoropyrrolidin-1-yl]-1H-pyrrolo[2,3-b]pyridin-3-yl}benzonitrile;
3-{4-[(2R)-2-methylmorpholin-4-yl]-1H-pyrrolo[2,3-b]pyridin-3-yl}benzonitrile;
3-[4-(pyrrolidin-1-yl)-1H-pyrrolo[2,3-b]pyridin-3-yl]benzonitrile;
3-{4-[(3S)-3-fluoropyrrolidin-1-yl]-1H-pyrrolo[2,3-b]pyridin-3-yl}benzonitrile;
3-[4-(3,3-difluoropiperidin-1-yl)-1H-pyrrolo[2,3-b]pyridin-3-yl]benzonitrile;
3-{4-[(2S)-2-methylmorpholin-4-yl]-1H-pyrrolo[2,3-b]pyridin-3-yl}benzonitrile;
4-[4-(morpholin-4-yl)-1H-pyrrolo[2,3-b]pyridin-3-yl]pyridin-2(1H)-one;
methyl 3-(3-cyanophenyl)-4-(morpholin-4-yl)-1H-pyrrolo[2,3-b]pyridine-5-carboxylate;
3-[5-(cyanomethyl)-4-(morpholin-4-yl)-1H-pyrrolo[2,3-b]pyridin-3-yl]benzonitrile;
3-[5-(methoxymethyl)-4-(morpholin-4-yl)-1H-pyrrolo[2,3-b]pyridin-3-yl]benzonitrile;
1-methyl-4-[4-(morpholin-4-yl)-1H-pyrrolo[2,3-b]pyridin-3-yl]-1H-pyrrole-2-carboxamide;
4-[4-(morpholin-4-yl)-1H-pyrrolo[2,3-b]pyridin-3-yl]-1H-pyrrole-2-carbonitrile;
1-methyl-4-[2-methyl-4-(morpholin-4-yl)-1H-pyrrolo[2,3-b]pyridin-3-yl]-1H-pyrrole-2-carbonitrile;
3-[4-(pyridin-4-yl)-1H-pyrrolo[2,3-b]pyridin-3-yl]benzonitrile;
3-(1-methyl-1H-pyrazol-4-yl)-4-phenyl-1H-pyrrolo[2,3-b]pyridine;
3-[4-(morpholin-4-yl)-7H-pyrrolo[2,3-c]pyridazin-5-yl]benzonitrile;
3-[3-(3-cyanophenyl)-1H-pyrrolo[2,3-b]pyridin-4-yl]-N-cyclopropylbenzamide;

2-fluoro-3-[4-(morpholin-4-yl)-7H-pyrrolo[2,3-c]pyridazin-5-yl]benzonitrile;
3-[4-(pyridin-3-yl)-1H-pyrrolo[2,3-b]pyridin-3-yl]benzonitrile;
4-(3,4-difluorophenyl)-3-(1-methyl-1H-pyrazol-4-yl)-1H-pyrrolo[2,3-b]pyridine;
4-(2,5-difluorophenyl)-3-(1-methyl-1H-pyrazol-4-yl)-1H-pyrrolo[2,3-b]pyridine;
4-(2,3-difluorophenyl)-3-(1-methyl-1H-pyrazol-4-yl)-1H-pyrrolo[2,3-b]pyridine;
4-(3-chlorophenyl)-3-(1-methyl-1H-pyrazol-4-yl)-1H-pyrrolo[2,3-b]pyridine;
4-(2-fluoro-3-methoxyphenyl)-3-(1-methyl-1H-pyrazol-4-yl)-1H-pyrrolo[2,3-b]pyridine;
3-[3-(3-cyanophenyl)-1H-pyrrolo[2,3-b]pyridin-4-yl]-N-methylbenzenesulfonamide;
4-cyclopropyl-3-(2,3-difluoro-6-methoxyphenyl)-1H-pyrrolo[2,3-b]pyridine-5-carbonitrile;
3-[4-(1-methyl-1H-pyrazol-4-yl)-1H-pyrrolo[2,3-b]pyridin-3-yl]benzonitrile;
3-(1-methyl-1H-pyrazol-4-yl)-4-(pyridin-4-yl)-1H-pyrrolo[2,3-b]pyridine;
4-(3,5-difluorophenyl)-3-(1-methyl-1H-pyrazol-4-yl)-1H-pyrrolo[2,3-b]pyridine;
4-(3-fluoro-4-methoxyphenyl)-3-(1-methyl-1H-pyrazol-4-yl)-1H-pyrrolo[2,3-b]pyridine;
4-(2-fluoro-4-methoxyphenyl)-3-(1-methyl-1H-pyrazol-4-yl)-1H-pyrrolo[2,3-b]pyridine;
4-(furan-3-yl)-3-(1-methyl-1H-pyrazol-4-yl)-1H-pyrrolo[2,3-b]pyridine;
5-[3-(1-methyl-1H-pyrazol-4-yl)-1H-pyrrolo[2,3-b]pyridin-4-yl]-1,3-benzothiazole;
{3-[3-(1-methyl-1H-pyrazol-4-yl)-1H-pyrrolo[2,3-b]pyridin-4-yl]phenyl}acetonitrile;
3-[3-(1-methyl-1H-pyrazol-4-yl)-1H-pyrrolo[2,3-b]pyridin-4-yl]benzonitrile;
5-(1-methyl-1H-pyrazol-4-yl)-4-(morpholin-4-yl)-7H-pyrrolo[2,3-c]pyridazine;
4-[3-(m ethoxymethyl)phenyl]-3-(1-methyl-1H-pyrazol-4-yl)-1H-pyrrolo[2,3-b]pyridine;
3-{4-[3-(5-methyl-1,3,4-oxadiazol-2-yl)phenyl]-1H-pyrrolo[2,3-b]pyridin-3-yl}benzonitrile;
or a pharmaceutically acceptable salt thereof.

A sixteenth embodiment of the first aspect of the present invention is a compound according to the first embodiment selected from the group consisting of:
3-[4-(morpholin-4-yl)-1H-pyrrolo[2,3-b]pyridin-3-yl]benzonitrile;
2-fluoro-3-[4-(morpholin-4-yl)-1H-pyrrolo[2,3-b]pyridin-3-yl]benzonitrile;
3-[4-(morpholin-4-yl)-1H-pyrrolo[2,3-b]pyridin-3-yl]imidazo[1,2-b]pyridazine;
1-methyl-4-[4-(morpholin-4-yl)-1H-pyrrolo[2,3-b]pyridin-3-yl]-1H-pyrrole-2-carbonitrile;
1-methyl-4-[4-(morpholin-4-yl)-1H-pyrrolo[2,3-b]pyridin-3-yl]-1H-imidazole-2-carbonitrile;
1-methyl-4-[4-(morpholin-4-yl)-7H-pyrrolo[2,3-c]pyridazin-5-yl]-1H-pyrrole-2-carbonitrile;
4-[2-chloro-4-(morpholin-4-yl)-1H-pyrrolo[2,3-b]pyridin-3-yl]-1-methyl-1H-pyrrole-2-carbonitrile;
3-(3-cyanophenyl)-4-(morpholin-4-yl)-1H-pyrrolo[2,3-b]pyridine-5-carbonitrile;
3-(1-methyl-1H-pyrazol-4-yl)-4-(morpholin-4-yl)-1H-pyrrolo[2,3-b]pyridine;
3-(3-cyano-2-fluorophenyl)-4-(dimethylamino)-1H-pyrrolo[2,3-b]pyridine-5-carbonitrile;
3-(2,3-difluorophenyl)-4-(morpholin-4-yl)-1H-pyrrolo[2,3-b]pyridine;
3-(2-fluorophenyl)-4-(morpholin-4-yl)-1H-pyrrolo[2,3-b]pyridine;
3-(3-fluoro-5-methylphenyl)-4-(morpholin-4-yl)-1H-pyrrolo[2,3-b]pyridine;
3-(3-cyano-2-fluorophenyl)-4-(morpholin-4-yl)-1H-pyrrolo[2,3-b]pyridine-5-carbonitrile;
3-(3-fluoro-5-methylphenyl)-4-(morpholin-4-yl)-1H-pyrrolo[2,3-b]pyridine-5-carbonitrile;
3-[4-(3, 6-dihydro-2H-pyran-4-yl)-1H-pyrrolo[2,3-b]pyridin-3-yl]benzonitrile;
3-[4-(3-hydroxypiperidin-1-yl)-1H-pyrrolo[2,3-b]pyridin-3-yl]benzonitrile;
3-[4-(pyrrolidin-1-yl)-1H-pyrrolo[2,3-b]pyridin-3-yl]benzonitrile;
3-{4-[(3S)-3-fluoropyrrolidin-1-yl]-1H-pyrrolo[2,3-b]pyridin-3-yl}benzonitrile;
3-{4-[(2S)-2-methylmorpholin-4-yl]-1H-pyrrolo[2,3-b]pyridin-3-yl}benzonitrile;
4-[4-(morpholin-4-yl)-1H-pyrrolo[2,3-b]pyridin-3-yl]pyridin-2(1H)-one;
methyl 3-(3-cyanophenyl)-4-(morpholin-4-yl)-1H-pyrrolo[2,3-b]pyridine-5-carboxylate;
1-methyl-4-[4-(morpholin-4-yl)-1H-pyrrolo[2,3-b]pyridin-3-yl]-1H-pyrrole-2-carboxamide;
4-[4-(morpholin-4-yl)-1H-pyrrolo[2,3-b]pyridin-3-yl]-1H-pyrrole-2-carbonitrile;
1-methyl-4-[2-methyl-4-(morpholin-4-yl)-1H-pyrrolo[2,3-b]pyridin-3-yl]-1H-pyrrole-2-carbonitrile;
3-[4-(pyridin-4-yl)-1H-pyrrolo[2,3-b]pyridin-3-yl]benzonitrile; and
3-(1-methyl-1H-pyrazol-4-yl)-4-phenyl-1H-pyrrolo[2,3-b]pyridine;
or a pharmaceutically acceptable salt thereof.

A first embodiment of a second aspect of the present invention is a pharmaceutical composition comprising a therapeutically effective amount of a compound according to any one of the first through sixteenth embodiments of the first aspect, or a pharmaceutically acceptable salt thereof together with a pharmaceutically acceptable carrier.

A first embodiment of a third aspect of the present invention is a method of treating Parkinson's disease in a patient, the method comprising administering to a patient in need thereof a therapeutically effective amount of a compound or pharmaceutically acceptable salt thereof according to any one of the first through sixteenth embodiments of the first aspect.

A first embodiment of a fourth aspect of the present invention is the compound or pharmaceutically acceptable salt thereof according to any one of the first through sixteenth embodiments of the first aspect for use in the treatment of Parkinson's disease.

Another embodiment of the present invention is a method of inhibiting LRRK2 in a patient, the method comprising administering a LRRK2 inhibiting amount of a compound or a pharmaceutically acceptable salt thereof according to any one of the first through sixteenth embodiments of the first aspect.

Another embodiment of the present invention is a method of treating a neurodegenerative disease in a patient, the method comprising administering to a patient in need thereof a therapeutically effective amount of a compound or pharmaceutically acceptable salt thereof according to any one of the first through sixteenth embodiments of the first aspect.

Accordingly, the invention is also directed to methods of treating a patient (preferably a human) for diseases in which the LRRK2 kinase is involved, such as Parkinson's Disease, by administering a therapeutically effective amount of a compound of any of the embodiments of formula I, or a pharmaceutically acceptable salt thereof, and a pharmaceutically acceptable carrier.

The invention is also directed to methods of inhibiting LRRK2 kinase activity, by administering a therapeutically effective amount of a compound of formula I or a pharmaceutically acceptable salt thereof, and a pharmaceutically acceptable carrier, to a mammal or a patient in need thereof. The invention is also directed to methods of treating disorders responsive to the inhibition of LRRK2 kinase activity, such as neurological disorders (particularly Parkinson's disease), certain cancers, and certain immunological disorders (such as Crohn's disease and leprosy) by administering a therapeutically effective amount of a compound of formula I or a pharmaceutically acceptable salt thereof, and a pharmaceutically acceptable carrier, to a mammal or a patient in need thereof.

The invention is also directed to methods for treating conditions or diseases of the central nervous system and neurological disorders in which the LRRK2 kinase is involved, particularly Parkinson's disease (but also including other neurological diseases which may include migraine; epilepsy; Alzheimer's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS) premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema) and pediatric psychiatric disorders (including attention deficit disorder, attention deficit/hyperactive disorder, conduct disorder, and autism) in a mammal, preferably a human, comprising administering to said mammal a therapeutically effective amount of a compound of formula I or a pharmaceutically acceptable salt thereof.

The text revision of the fourth edition of the Diagnostic and Statistical Manual of Mental Disorders (DSM-IV-TR) (2000, American Psychiatric Association, Washington D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress.

Preferred methods are for treating a neurological disorder, most preferably Parkinson's disease, (but also other neurological disorders such as migraine; epilepsy; Alzheimer's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof. In addition, the compounds of Formula I and pharmaceutically acceptable salts thereof may also be employed in methods of treating other disorders associated with LRRK2 such as Crohn's disease, leprosy and certain cancers, such as kidney, breast, lung, prostate, lung and blood cancer.

Also provided herein are compositions comprising a pharmaceutically effective amount of one or more of the compounds described herein and a pharmaceutically acceptable vehicle, carrier or excipient.

The present invention is also directed to the use of a combination of a LRRK2 inhibitor compound of formula I, and one or more additional pharmaceutically active agent(s).

Other features and advantages of this invention will be apparent from this specification and the appendent claims which describe the invention.

Definitions

The term "alkyl" refers to a linear or branched-chain saturated hydrocarbyl substituent (i.e., a substituent obtained from a hydrocarbon by removal of a hydrogen); in one embodiment from one to six carbon atoms (i.e., $C_1$-$C_6$alkyl); in another embodiment, from one to three carbon atoms (i.e., $C_1$-$C_3$alkyl). Examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent (i.e., a substituent obtained from a hydrocarbon by removal of a hydrogen) which is in turn attached to an oxygen atom; in one embodiment from one to six carbon atoms (i.e., $C_1$-$C_6$alkoxy); in another embodiment, from one to three carbon atoms (i.e., $C_1$-$C_3$alkoxy). Examples of such substituents include methoxy, ethoxy, propoxy (including n-propoxy and isopropoxy), butoxy (including n-butoxy, isobutoxy, sec-butoxy and tert-butoxy), pentoxy and the like.

The term "cycloalkyl" refers to a carbocyclic substituent obtained by removing a hydrogen from a saturated carbocyclic molecule and having the specified number of carbon atoms. In one embodiment, a cycloalkyl substituent has three to seven carbon atoms (i.e., $C_3$-$C_7$cycloalkyl).

Examples of cycloalkyl include cyclopropyl, cyclobutyl, cyclopentyl, cyclohexyl and cycloheptyl. The term "cycloalkyl" includes mono-, bi- and tricyclic saturated carbocycles, as well as bridged and fused ring carbocycles, as well as spiro-fused ring systems.

In some instances, the number of atoms in a cyclic substituent containing one or more heteroatoms (i.e., heteroaryl or heterocycloalkyl) is indicated by the prefix "x to y membered", wherein x is the minimum and y is the maximum number of atoms forming the cyclic moiety of the substituent. The term "heterocycloalkyl" refers to a substituent obtained by removing a hydrogen from a saturated or partially saturated ring structure containing the specified number of ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. If the heterocycloalkyl substituent is in turn substituted with a group or substituent, the group or substituent may be bound to a nitrogen heteroatom, or it may be bound to a ring carbon atom, as appropriate. As used herein, the term "heterocycloalkyl" as used herein refers to a monocyclic ring system containing the heteroatoms N, O or S as specified. Thus, for example, "four to seven membered heterocycloalkyl" refers to a heterocycloalkyl containing from 4 to 7 atoms, including one or more heteroatoms, in the cyclic moiety of the heterocycloalkyl. The term "heterobicycloalkyl" as used herein refers to a non-spiro bicyclic ring system containing the heteroatoms N, O or S as specified. Thus, for example, "six to twelve membered heterobicycloalkyl" refers to a heterobicycloalkyl containing from 6 to 12 atoms, including one or more heteroatoms, in the cyclic moieties of the heterobicycloalkyl.

The term "hydrogen" refers to a hydrogen substituent, and may be depicted as —H.

The term "hydroxy" or "hydroxyl" refers to —OH. Compounds bearing a carbon to which one or more hydroxy substituents are attached include, for example, alcohols, enols and phenol.

The term "halo" or "halogen" refers to fluoro (which may be depicted as —F), chloro (which may be depicted as —Cl), bromo (which may be depicted as —Br), or iodo (which may be depicted as —I).

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A five to six membered heteroaryl is an aromatic ring system which has five or six ring atoms with at least one of the ring atoms being N, O or S. Similarly, a five to ten membered heteroaryl is an aromatic ring system which has five to ten ring atoms with at least one of the ring atoms being N, O or S. A heteroaryl may be a single ring or 2 fused rings. Examples of heteroaryl substituents include 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

Examples of single-ring heterocycloalkyls include azetidinyl, oxetanyl, thietanyl, dihydrofuranyl, tetrahydrofuranyl, dihydrothiophenyl, tetrahydrothiophenyl, pyrrolinyl, pyrrolidinyl, imidazolinyl, imidazolidinyl, pyrazolinyl, pyrazolidinyl, thiazolinyl, isothiazolinyl, thiazolidinyl, isothiazolidinyl, dihydropyranyl, piperidinyl, morpholinyl, piperazinyl, azepinyl, oxepinyl, thiepinyl, and diazepinyl.

Examples of 2-fused-ring heteroaryls include, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, pyrrolopyridinyl, pyrazolopyridinyl and imidazothiazolyl. Other examples of fused-ring heteroaryls include benzo-fused heteroaryls such as indolyl, isoindolyl, indoleninyl, isoindazolyl, benzazinyl (including quinolinyl or isoquinolinyl), phthalazinyl, quinoxalinyl, quinazolinyl, benzodiazinyl (including cinnolinyl or quinazolinyl).

The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

If substituents are described as being "independently selected" from a group, each instance of a substituent is selected independent of the other. Each substituent therefore may be identical to or different from the other substituent(s).

As used herein the term "formula I" or "Formula I" may be referred to as a "compound(s) of the invention." Such terms are also defined to include all forms of the compound of formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention may have asymmetric carbon atoms. The carbon-carbon bonds of the compounds of the invention may be depicted herein using a solid line ( ———— ), a solid wedge ( ◀━━ ) or a dotted wedge ( ·······ııııı ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention comprises the tautomeric forms of compounds of the invention. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form is dependent on the various substituents on the molecule as well as the particular crystallization technique used to isolate a compound.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, β-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of formula I with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorus, sulfur, fluorine and chlorine, such as $^{2}H$, $^{3}H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

DETAILED DESCRIPTION OF THE INVENTION

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, (hydroxypropyl)methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a LRRK2 inhibitor compound as provided in formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of formula I or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of Formula I, depending on the disease, disorder, or condition to be treated. For example, a pharmaceutical composition for use in treating Parkinson's disease may comprise a compound of formula I or a pharmaceutically acceptable salt thereof together with another agent such as a dopamine (levodopa, either alone or with a DOPA decarboxylase inhibitor), a monoamine oxidase (MAO) inhibitor, a catechol O-methyltransferase (COMT) inhibitor or an anticholinergic agent, or any combination thereof. Particularly preferred agents to combine with the compounds of formula I for use in treating Parkinson's disease include levodopa, carbidopa, tolcapone, entacapone, selegiline, benztropine and trihexyphenidyl, or any combination thereof. Pharmaceutically active agents that may be used in combination with the compounds of formula I and compositions thereof include, without limitation:

(i) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluoromethyldopa, difluoromethyldopa, brocresine, or m-hydroxybenzylhydrazine);

(ii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(iii) catechol O-methyltransferase (COMT) inhibitors, such as nitecapone, tolcapone (TASMAR), entacapone (COMTAN), and tropolone;

(iv) monoamine oxidase (MAO) inhibitors, such as selegiline (EMSAM), selegiline hydrochloride (I-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-β (or fragments thereof), such as $A\beta_{1-15}$ conjugated to pan HLA DR-binding epitope (PADRE®), ACC-001 (Elan/Wyeth), and Affitope;

(vii) antibodies to amyloid-1 (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate, celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the gingko biloba extract EGb-761 (ROKAN®, TEBONIN®), tramiprosate (CEREBRIL®, ALZHEMED®), KIACTA®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) phosphodiesterase (PDE) inhibitors, including (a) PDE1 inhibitors; (b) PDE2 inhibitors; (c) PDE3 inhibitors; (d) PDE4 inhibitors; (e) PDE5 inhibitors; (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)); and (g) PDE10 inhibitors such as 2-({4-[1-methyl-4-(pyridin-4-yl)-1H-pyrazol-3-yl]phenoxy}methyl)quinoline (PF-2545920);

(xiii) serotonin (5-hydroxytryptamine) 1A ($5\text{-HT}_{1A}$) receptor antagonists, such as spiperone, levo-pindolol, lecozotan;

(xiv) serotonin (5-hydroxytryptamine) 2C ($5\text{-HT}_{2c}$) receptor agonists, such as vabicaserin, and zicronapine; serotonin (5-hydroxytryptamine) 4 ($5\text{-HT}_4$) receptor agonists/antagonists, such as PRX-03140 (Epix) and PF-04995274;

(xv) serotonin (5-hydroxytryptamine) 3C ($5\text{-HT}_{3c}$) receptor antagonists, such as Ondansetron (Zofran);

(xvi) serotonin (5-hydroxytryptamine) 6 ($5\text{-HT}_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xviii) Glycine transporter-1 inhibitors such as paliflutine, ORG-25935, and ORG-26041; and mGluR modulators such as AFQ-059 and amantidine;

(xix) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xx) P450 inhibitors, such as ritonavir;

(xxi) tau therapy targets, such as davunetide;

and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

General Synthetic Schemes

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in many cases, the compounds in Schemes 1 through 5 will be generated as a mixture of diastereomers and/or enantiomers; these may be separated at various stages of the synthetic schemes using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatographic methods such as high performance liquid chromatography (HPLC) or thin layer chromatography (TLC).

DETAILED DESCRIPTION OF THE INVENTION

Compounds of Formula I and intermediates thereof may be prepared according to the following reaction schemes and accompanying discussion. Unless otherwise indicated, $R^1$, $R^2$, $R^3$, $R^4$ and X in the reaction schemes and discussions that follow are as defined hereinabove. In general, the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes may be described in the experimental section. The schemes and examples provided herein (including the corresponding description) are for illustration only, and not intended to limit the scope of the present invention.

Scheme 1 refers to preparation of compounds of Formula Ia which are compounds of Formula I in which $R^1$ is $NR^6R^7$. Referring to Scheme 1, compounds of Formula 1-1 and 1-2 [wherein Lg is a leaving group such as Br or I, and Pg is a suitable protecting group, such as 2-(trimethylsilyl)ethoxymethyl (SEM), p-toluenesulfonyl (tosyl) or tert-butoxycarbonyl (BOC)] are commercially available or can be made by methods described herein or other methods well known to those skilled in the art.

A compound of Formula 1-3 can be prepared by coupling a compound of Formula 1-1 with a compound of Formula 1-2, for example, by heating a mixture of a compound of Formula 1-1 with a compound of Formula 1-2 in the presence of a base, such as N,N-diisopropylethylamine, in an appropriate solvent, such as n-butanol, at temperatures ranging between 50° C. and 200° C. Suitable reaction times are typically from 20 minutes to 48 hours. Alternatively, a metal-catalyzed (such as using a palladium or copper catalyst) coupling may be employed to accomplish the aforesaid coupling. In this variant of the coupling, a mixture of a compound of Formula 1-1 and a compound of Formula 1-2 can be heated at temperatures ranging between 50° C. and 120° C. in the presence of a base [such as cesium carbonate], a metal catalyst [such as a palladium catalyst, e.g., palladium (II) acetate], and a ligand [such as 1,1'-binaphthalene-2,2'-diylbis(diphenylphosphane) (BINAP)] in an appropriate solvent, such as 1,4-dioxane. Suitable reaction times are typically from 30 minutes to 48 hours.

A compound of Formula 1-3 can subsequently be reacted with a compound of Formula $R^2$-M [wherein M can be $B(OH)_2$; $B(OR)_2$ wherein each R is independently H or $C_{1-6}$ alkyl, or wherein two (OR) groups, together with the B atom to which they are attached, form a 5- to 10-membered heterocyclic ring optionally substituted with one or more $C_{1-6}$ alkyl; a trialkyltin moiety; or the like] by a metal-catalyzed (such as using a palladium catalyst) coupling reaction to obtain a compound of Formula 1-4. Compounds of Formula $R^2$-M are commercially available or can be prepared by methods analogous to those described in the chemical art. Alternatively, a compound of Formula 1-3 can be converted to a compound of Formula 1-5 [wherein M is defined as above]. A compound of Formula 1-5 can then be reacted with a compound of Formula $R^2$-Lg [wherein Lg is defined as above] by a metal-catalyzed (such as using a palladium catalyst) coupling reaction to obtain a compound of Formula I. Compounds of Formula $R^2$-Lg are commercially available or can be prepared by methods analogous to those described in the chemical art. The type of reaction employed depends on the selection of Lg and M. For example, when Lg is halogen or triflate and the $R^2$-M reagent is a boronic acid or boronic ester, a Suzuki reaction may be used [A. Suzuki, *J. Organomet. Chem.* 1999, 576, 147-168; N. Miyaura and A. Suzuki, Chem. Rev. 1995, 95, 2457-2483; A. F. Littke et al., *J. Am. Chem. Soc.* 2000, 122, 4020-4028]. Alternatively, when Lg is halogen or triflate and M is trialkyltin, a Stille coupling may be employed [V. Farina et al., *Organic Reactions* 1997, 50, 1-652]. Where Lg is Br, I or triflate and M is Zn or Mg, a Negishi coupling or Kumada coupling may be used [E. Erdik, *Tetrahedron* 1992, 48, 9577-9648; T. Banno et al., *J. Organomet. Chem.* 2002, 653, 288-291]. Removal of the protecting group from compounds of Formula 1-4 under conditions well known to those skilled in the art affords compounds of Formula Ia.

Scheme 1

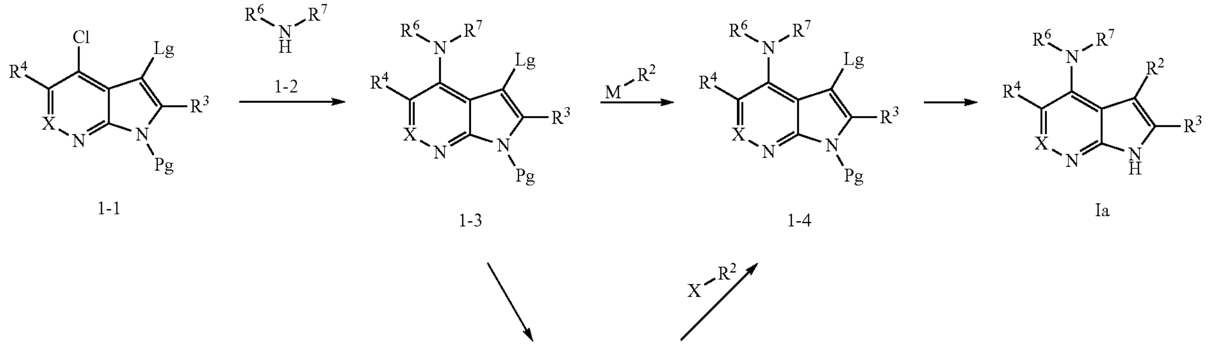

1-1 1-3 1-4 Ia

-continued

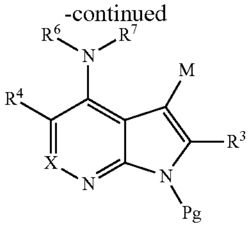

1-5

Scheme 2 also refers to preparation of compounds of Formula Ia. Referring to Scheme 2, compounds of Formula Ia may be prepared utilizing analogous chemical transformations to those described in Scheme 1, but with a different ordering of steps. A compound of Formula 1-1 (as in Scheme 1) can be converted to a compound of Formula 2-1 either directly or after conversion to a compound of Formula 2-2 using methods analogous to those described in Scheme 1. A compound of Formula 2-1 may then be coupled to a compound of Formula 1-2 as in Scheme 1, to produce a compound of Formula 1-4. The coupling conditions employed may be analogous to those described for the preparation of a compound of Formula 1-3 in Scheme 1.

Scheme 3

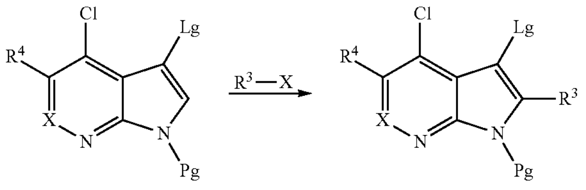

3-1 1-1

Scheme 2

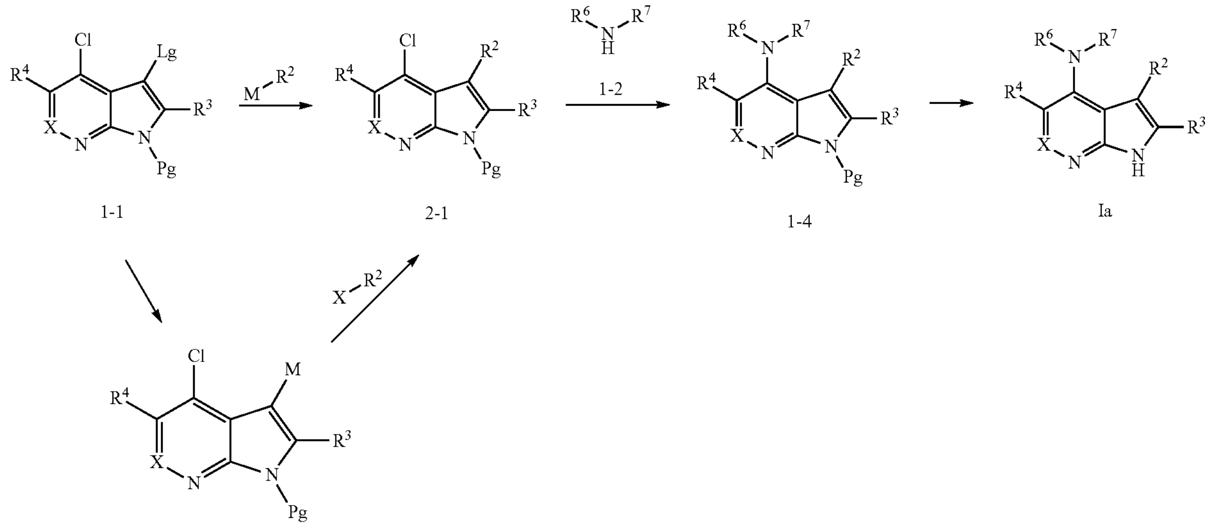

Scheme 3 refers to a preparation of a compound of Formula 1-1. Referring to Scheme 3, compounds of Formula 3-1 are commercially available or can be made by methods described herein or other methods well known to those skilled in the art. A compound of Formula 3-1 can be treated with a strong base and the intermediate can be subsequently reacted with an electrophile to obtain a compound of Formula 1-1 Examples of suitable reaction conditions for the reaction include mixing a compound of Formula 3-1 with a suitable base, such as lithium diisopropylamide, in a suitable reaction solvent such as tetrahydrofuran. This is followed by addition of an electrophile such as an alkyl iodide or bromide. Suitable temperatures for the aforesaid reaction are typically between −78° C. and 30° C. Suitable reaction times typically are from 20 minutes to 48 hours. A compound of Formula 1-1 can be converted to a compound of Formula Ia using chemistry described in Schemes 1 and 2.

Scheme 4 refers to a preparation of a compound of Formula I from compounds of Formulae 4-1 or 4-1'. For the reaction of compound 4-1 with $R^2$-M or 4-1' with $R^2$-Lg, Lg is an appropriate leaving group such as chloro or iodo, Pg is an appropriate amine protecting group and M is an appropriate metal, such as a boronate when a Suzuki type coupling is employed. Numerous variants of this type of coupling are known in the art, such as those described above for Reaction Schemes 1 and 2, and these methods can be employed for the conversion of compound 4-1 or 4-1' to compound 4-2. Compound 4-2 can then be deprotected by methods known in the art to provide the compound of Formula I.

Scheme 4

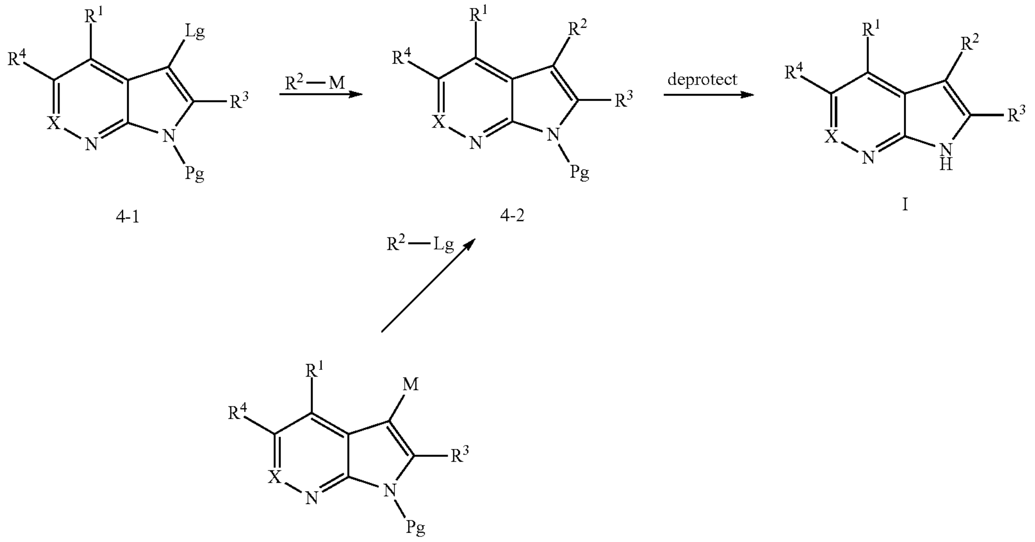

4-1 4-2 I 4-1'

Scheme 5 refers to a preparation of a compound of Formula I from compounds of Formulae 5-1 or 5-1' in a manner analogous to that described in Scheme 4. For the reaction of compound 5-1 with $R^1$-M or 5-1' with $R^1$-Lg, Lg is an appropriate leaving group such as chloro or iodo, Pg is an appropriate amine protecting group and M is an appropriate metal, such as a boronate when a Suzuki type coupling is employed. Numerous variants of this type of coupling are known in the art, such as those described above for Reaction Schemes 1 and 2, and these methods can be employed for the conversion of compound 5-1 or 5-1' to compound 5-2. Compound 5-2 can then be deprotected by methods known in the art to provide the compound of Formula I.

The methods generically described in Schemes 1-5 are not to be construed in a limiting manner. It is to be understood by one skilled in the art that variation in the order of certain reaction steps and conditions may be employed to provide compounds of Formula I. More specific examples of the methods used to prepare compounds of Formula I are provided below in Examples 1-12 and general methods A-D, and likewise these methods are also not to be construed by one skilled in the art in a limiting manner.

Experimental Procedures

The following illustrate the synthesis of various compounds of the present invention. Additional compounds Scheme 5

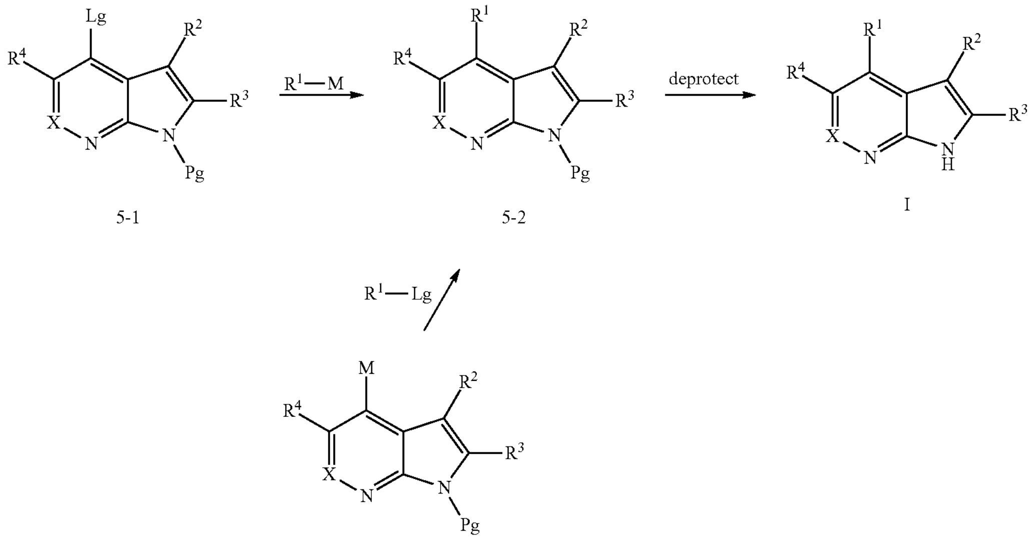

5-1 5-2 I 5-1' within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCl) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

Example 1

3-[4-(Morpholin-4-yl)-1H-pyrrolo[2,3-b]pyridin-3-yl]benzonitrile (1)

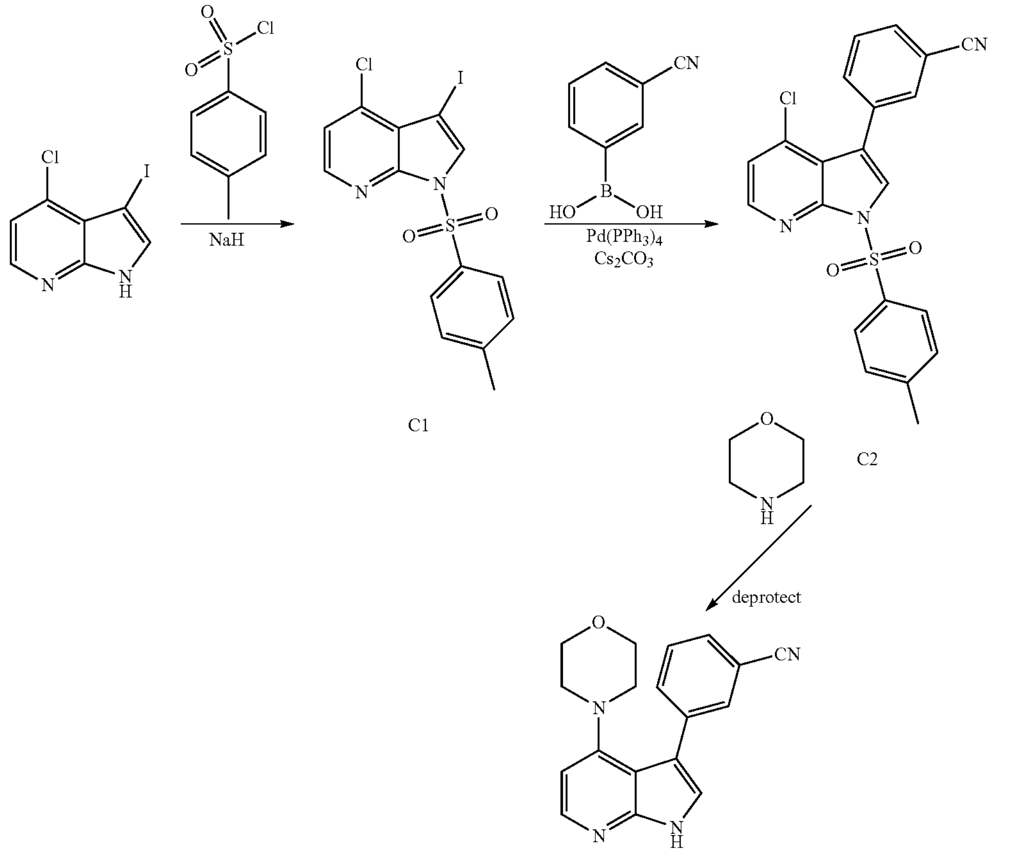

C1

C2

1

Step 1. Synthesis of 4-chloro-3-iodo-1-[(4-methylphenyl)sulfonyl]-1H-pyrrolo[2,3-b]pyridine (C1)

A solution of 4-chloro-3-iodo-1H-pyrrolo[2,3-b]pyridine (12 g, 43 mmol) in tetrahydrofuran (200 mL) was added drop-wise to a 0° C. suspension of sodium hydride (60% in mineral oil, 2.6 g, 65 mmol) in tetrahydrofuran (300 mL). After completion of the addition, the reaction mixture was allowed to stir for 15 minutes, whereupon p-toluenesulfonyl chloride (12.4 g, 65.0 mmol) was added in portions at a rate such that the temperature was maintained at 5° C. The reaction mixture was then allowed to stir at room temperature for 3 hours, at which time it was partitioned between saturated aqueous sodium bicarbonate solution (300 mL) and ethyl acetate (300 mL). The aqueous layer was extracted with ethyl acetate (3×300 mL), and the combined organic layers were washed with saturated aqueous sodium chloride solution (200 mL), dried over sodium sulfate, filtered, and concentrated in vacuo. Silica gel chromatography (Gradient: 25% to 100% ethyl acetate in petroleum ether) afforded the product as a yellow solid. Yield: 8.0 g, 18 mmol, 42%. $^1H$ NMR (400 MHz, DMSO-$d_6$) δ 8.34 (d, J=5.3 Hz, 1H), 8.23 (s, 1H), 8.02 (d, J=8.0 Hz, 2H), 7.40-7.47 (m, 3H), 2.34 (s, 3H).

Step 2. Synthesis of 3-{4-chloro-1-[(4-methylphenyl)sulfonyl]-1H-pyrrolo[2,3-b]pyridin-3-yl}benzonitrile (C2)

To a stirred solution of C1 (3 g, 7 mmol) and (3-cyanophenyl)boronic acid (1 g, 7 mmol) in a 4:1 mixture of 1,4-dioxane and water (50 mL) was added tetrakis(triphenylphosphine)palladium(0) (0.4 g, 0.3 mmol) and cesium carbonate (6.8 g, 21 mmol). The mixture was degassed and purged with nitrogen three times, and then irradiated at 120° C. in a microwave reactor for 20 minutes. After extraction with ethyl acetate (3×200 mL), the combined organic layers were washed with saturated aqueous sodium chloride solution (100 mL), dried over sodium sulfate, filtered, and concentrated under reduced pressure. Silica gel chromatography (Gradient: 0% to 10% ethyl acetate in petroleum ether) provided the product as a yellow solid. Yield: 1.0 g, 2.5 mmol, 36%. $^1H$ NMR (400 MHz, DMSO-$d_6$) δ 8.38 (d, J=5.3 Hz, 1H), 8.20 (s, 1H), 8.06-8.10 (m, 3H), 7.92 (ddd, J=7.8, 1.6, 1.2 Hz, 1H), 7.88 (ddd, J=7.8, 1.5, 1.1 Hz, 1H), 7.65 (br dd, J=7.8, 7.8 Hz, 1H), 7.47 (d, J=5.1 Hz, 1H), 7.46 (br d, J=8 Hz, 2H), 2.36 (s, 3H).

Step 3. Synthesis of 3-[4-(morpholin-4-yl)-1H-pyrrolo[2,3-b]pyridin-3-yl]benzonitrile (1)

A mixture of C2 (1.0 g, 2.5 mol) and morpholine (15 mL) was irradiated at 200° C. in a microwave reactor for 2 hours. The reaction mixture was then diluted with water (50 mL) and extracted with ethyl acetate (3×50 mL); the combined organic layers were washed with saturated aqueous sodium chloride solution (50 mL), dried over sodium sulfate, filtered, and concentrated in vacuo. Purification via reversed phase HPLC (Column: Phenomenex Gemini C18, 5 μm; Mobile phase A: aqueous ammonia, pH 10; Mobile phase B: acetonitrile; Gradient: 26% to 46% B) afforded the product as a white solid. Yield: 52 mg, 0.17 mmol, 7%. LCMS m/z 305.1 $[M+H]^+$. $^1H$ NMR (400 MHz, $CDCl_3$) δ 9.87 (br s, 1H), 8.28 (d, J=5.3 Hz, 1H), 7.96 (br s, 1H), 7.85 (br d, J=7.8 Hz, 1H), 7.61 (br d, J=7.7 Hz, 1H), 7.54 (dd, J=7.8, 7.6 Hz, 1H), 7.32 (s, 1H), 6.71 (d, J=5.4 Hz, 1H), 3.46-3.53 (m, 4H), 2.93-3.00 (m, 4H).

Example 2

2-Fluoro-3-[4-(morpholin-4-yl)-1H-pyrrolo[2,3-b]pyridin-3-yl]benzonitrile (2)

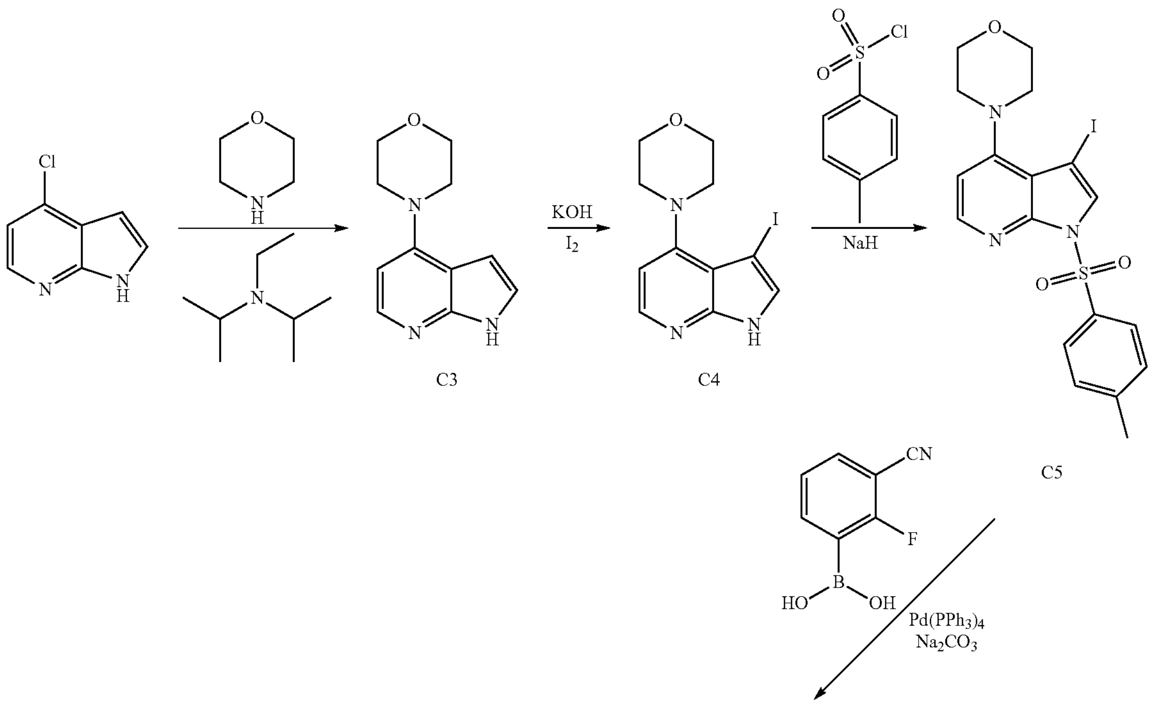

C3

C4

C5

-continued

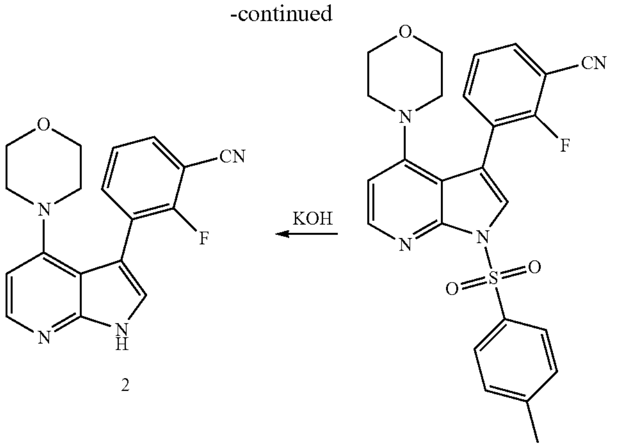

2

C6

Step 1. Synthesis of 4-(morpholin-4-yl)-1H-pyrrolo[2,3-b]pyridine (C3)

To a solution of 4-chloro-1H-pyrrolo[2,3-b]pyridine (3 g, 20 mmol) and morpholine (8.5 g, 98 mmol) in 1-methyl-pyrrolidin-2-one (20 mL) was added N,N-diisopropylethylamine (12.7 g, 98 mmol). The reaction mixture was heated at 180° C. in a sealed tube for 6 hours, and then poured into water (150 mL). The resulting suspension was filtered to provide the product as a yellow solid. Yield: 3.5 g, 17 mmol, 85%. $^1$H NMR (400 MHz, DMSO-$d_6$) δ 11.44 (br s, 1H), 7.96 (d, J=5.3 Hz, 1H), 7.24 (d, J=3.3 Hz, 1H), 6.49 (d, J=3.3 Hz, 1H), 6.42 (d, J=5.5 Hz, 1H), 3.74-3.82 (m, 4H), 3.30-3.38 (m, 4H, assumed; partially obscured by water peak).

Step 2. Synthesis of 3-iodo-4-(morpholin-4-yl)-1H-pyrrolo[2,3-b]pyridine (C4)

To a 0° C. solution of C3 (3.5 g, 17 mmol) in N,N-dimethylformamide (80 mL) was added potassium hydroxide (2.4 g, 43 mmol) and iodine (4.36 g, 17.2 mmol). The reaction mixture was stirred at 0° C. for 3 hours, whereupon it was poured into ice water (50 mL); the resulting suspension was collected via filtration to afford the product as a yellow solid. Yield: 3.9 g, 12 mmol, 71%. $^1$H NMR (400 MHz, DMSO-$d_6$) δ 12.00 (br s, 1H), 8.09 (d, J=5.3 Hz, 1H), 7.57 (s, 1H), 6.65 (d, J=5.3 Hz, 1H), 3.84-3.93 (m, 4H), 3.05-3.15 (m, 4H).

Step 3. Synthesis of 3-iodo-1-[(4-methylphenyl)sulfonyl]-4-(morpholin-4-yl)-1H-pyrrolo[2,3-b]pyridine (C5)

To a suspension of C4 (13.0 g, 39.5 mmol) in tetrahydrofuran (300 mL) was added sodium hydride (60% in mineral oil, 2.37 g, 59.2 mmol) at 0° C. The reaction mixture was stirred at 0° C. for 30 minutes, whereupon p-toluenesulfonyl chloride (8.3 g, 44 mmol) was added and stirring was continued at 0° C. for 5 hours. The reaction mixture was then poured into aqueous hydrochloric acid (0.5 M, 200 mL) and extracted with ethyl acetate (3×200 mL); the combined organic layers were washed with saturated aqueous sodium chloride solution (200 mL), dried over sodium sulfate, filtered, and concentrated under reduced pressure. Recrystallization from dichloromethane provided the product as a yellow solid. Yield: 12 g, 25 mmol, 63%. LCMS m/z 483.8 $[M+H]^+$. $^1$H NMR (400 MHz, $CDCl_3$) δ 8.30 (d, J=5.4 Hz, 1H), 8.09 (br d, J=8.4 Hz, 2H), 7.84 (s, 1H), 7.29 (br d, J=8.2 Hz, 2H), 6.74 (d, J=5.5 Hz, 1H), 3.95-4.01 (m, 4H), 3.10-3.17 (m, 4H), 2.39 (s, 3H).

Step 4. Synthesis of 2-fluoro-3-{1-[(4-methylphenyl)sulfonyl]-4-(morpholin-4-yl)-1H-pyrrolo[2,3-b]pyridin-3-yl}benzonitrile (C6)

To a solution of C5 (500 mg, 1.03 mmol) and (3-cyano-2-fluorophenyl)boronic acid (206 mg, 1.25 mmol) in 1,4-dioxane (10 mL) and water (2 mL) were added tetrakis(triphenylphosphine)palladium(0) (120 mg, 0.104 mmol) and sodium carbonate (220 mg, 2.08 mmol). The reaction mixture was degassed and purged with nitrogen several times, then placed in a sealed tube and stirred at 120° C. in a microwave reactor for 40 minutes. After being diluted with water (30 mL), the reaction mixture was extracted with ethyl acetate (3×50 mL); the combined organic layers were washed with saturated aqueous sodium chloride solution (30 mL), dried over sodium sulfate, filtered, and concentrated in vacuo. Silica gel chromatography (Gradient: 0% to 15% ethyl acetate in petroleum ether) afforded the product as a yellow solid, which was taken into the following step without additional purification. Yield: 0.30 g, 0.63 mmol. LCMS m/z 477.0 $[M+H]^+$.

Step 5. Synthesis of 2-fluoro-3-[4-(morpholin-4-yl)-1H-pyrrolo[2,3-b]pyridin-3-yl]benzonitrile (2)

Potassium hydroxide (233 mg, 4.15 mmol) was added to a solution of C6 (from the previous step, 0.30 g, mmol) in 1,4-dioxane (5 mL), and the reaction mixture was stirred at 30° C. for 2 hours. Solvent was removed in vacuo, and the residue was purified via reversed phase HPLC (Column: Phenomenex Gemini C18, 8 μm; Mobile phase A: aqueous ammonia, pH 10; Mobile phase B: acetonitrile; Gradient: 37% to 57% B), providing the product as a yellow solid. Yield: 18.4 mg, 57.1 μmol, 6% over two steps. LCMS m/z 323.1 $[M+H]^+$. $^1$H NMR (400 MHz, DMSO-$d_6$) δ 12.08 (br s, 1H), 8.16 (d, J=5.3 Hz, 1H), 7.83-7.91 (m, 2H), 7.61 (s, 1H), 7.50 (dd, J=7.8, 7.6 Hz, 1H), 6.71 (d, J=5.4 Hz, 1H), 3.22-3.29 (m, 4H), 2.75-2.81 (m, 4H).

Example 3

3-[4-(Morpholin-4-yl)-1H-pyrrolo[2,3-b]pyridin-3-yl]imidazo[1,2-b]pyridazine (3)

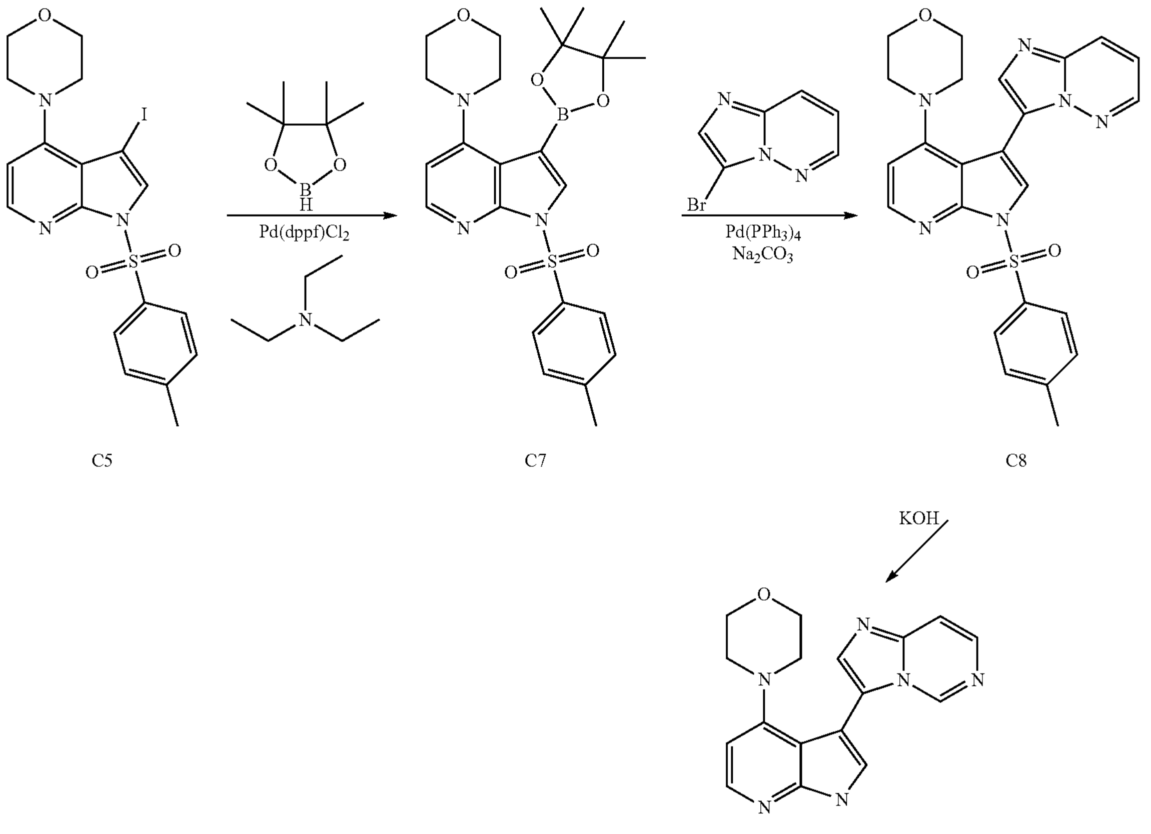

C5 C7 C8

3

Step 1. Synthesis of 1-[(4-methylphenyl)sulfonyl]-4-(morpholin-4-yl)-3-(4,4,5,5-tetramethyl-1,3,2-dioxaborolan-2-yl)-1H-pyrrolo[2,3-b]pyridine (C7)

[1,1'-Bis(diphenylphosphino)ferrocene]dichloropalladium(II), dichloromethane complex (84 mg, 0.10 mmol) and triethylamine (418 mg, 4.13 mmol) were added to a solution of C5 (0.50 g, 1.0 mmol) and 4,4,5,5-tetramethyl-1,3,2-dioxaborolane (530 mg, 4.14 mmol) in 1,4-dioxane (10 mL). The reaction mixture was degassed and purged with nitrogen several times, then placed in a sealed tube and stirred at 120° C. in a microwave reactor for 30 minutes. After dilution with water (20 mL), the mixture was extracted with ethyl acetate (3×30 mL), and the combined organic layers were washed with saturated aqueous sodium chloride solution (20 mL), dried over sodium sulfate, filtered, and concentrated in vacuo. Chromatography on silica gel (Gradient: 0% to 30% ethyl acetate in petroleum ether) afforded the product as a brown oil. Yield: 0.45 g, 0.93 mmol, 93%. LCMS m/z 483.8 $[M+H]^+$.

Step 2. Synthesis of 3-{1-[(4-methylphenyl)sulfonyl]-4-(morpholin-4-yl)-1H-pyrrolo[2,3-b]pyridin-3-yl}imidazo[1,2-b]pyridazine (C8)

Tetrakis(triphenylphosphine)palladium(0) (64 mg, 55 μmol) and sodium carbonate (118 mg, 1.11 mmol) were added to a solution of 3-bromoimidazo[1,2-b]pyridazine (110 mg, 0.555 mmol) and C7 (295 mg, 0.610 mmol) in 1,4-dioxane (5 mL) and water (1 mL). The reaction mixture was degassed and purged with nitrogen several times, then placed in a sealed tube and heated at 120° C. in a microwave reactor for 30 minutes. The reaction mixture was diluted with water (20 mL) and extracted with ethyl acetate (3×30 mL); the combined organic layers were washed with saturated aqueous sodium chloride solution (20 mL), dried over sodium sulfate, filtered, and concentrated in vacuo. Preparative thin layer chromatography (Eluent: ethyl acetate) provided the product as a yellow solid. Yield: 120 mg, 253 mmol, 46%. LCMS m/z 475.1 $[M+H]^+$.

Step 3. Synthesis of 3-[4-(morpholin-4-yl)-1H-pyrrolo[2,3-b]pyridin-3-yl]imidazo[1,2-b]pyridazine (3)

To a solution of C8 (120 mg, 253 μmol) in methanol (5 mL) was added potassium hydroxide (71 mg, 1.3 mmol), and the reaction mixture was stirred at 50° C. for 1 hour. Solvent was removed in vacuo, and the residue was purified by reversed phase HPLC (Column: Phenomenex Gemini C18, 8 μm; Mobile phase A: aqueous ammonia, pH 10; Mobile phase B: acetonitrile; Gradient: 18% to 38% B), affording the product as a yellow solid. Yield: 55.2 mg, 172 μmol, 68%. LCMS m/z 321.1 $[M+H]^+$. $^1H$ NMR (400 MHz, DMSO-$d_6$) δ 12.04 (v br s, 1H), 8.48 (dd, J=4.5, 1.5 Hz, 1H), 8.18 (dd, J=9.3, 1.3 Hz, 1H), 8.14 (d, J=5.5 Hz, 1H), 7.95 (s, 1H), 7.74 (s, 1H), 7.23 (dd, J=9.3, 4.3 Hz, 1H), 6.64 (d, J=5.0 Hz, 1H), 2.96-3.04 (m, 4H), 2.70-2.77 (m, 4H).

Example 4

1-Methyl-4-[4-(morpholin-4-yl)-1H-pyrrolo[2,3-b]pyridin-3-yl]-1H-pyrrole-2-carbonitrile (4)

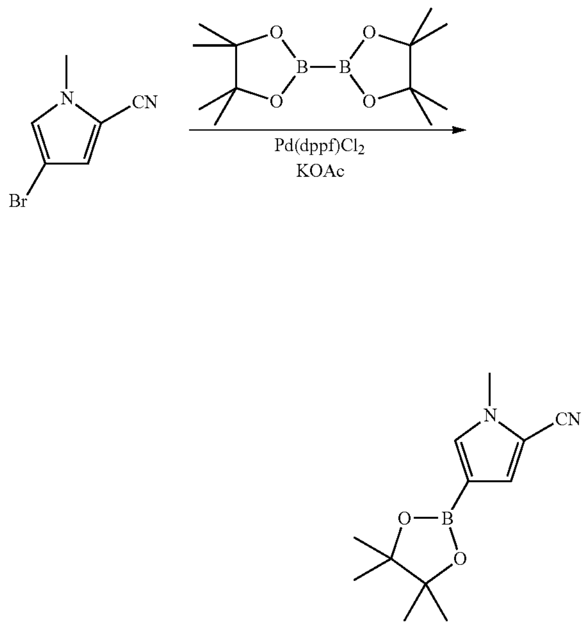

C9

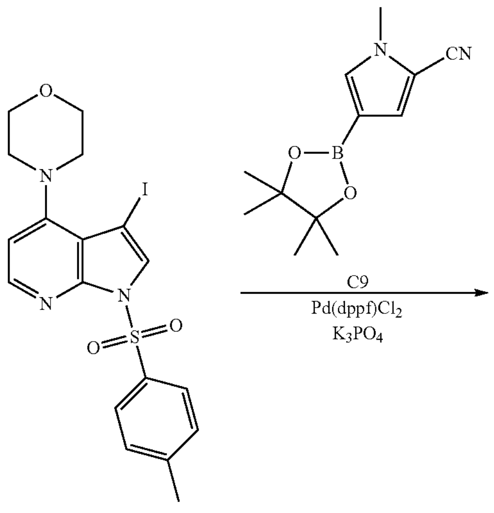

C5

-continued

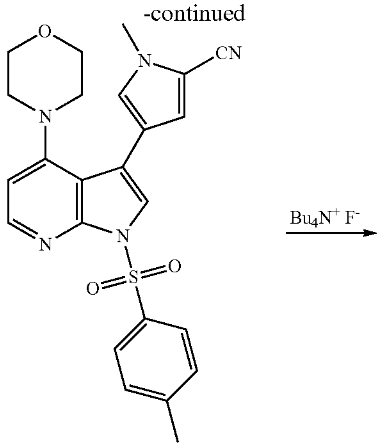

C10

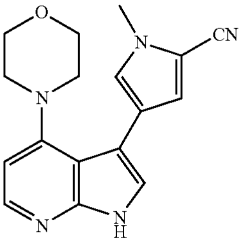

4

Step 1. Synthesis of 1-methyl-4-(4,4,5,5-tetramethyl-1,3,2-dioxaborolan-2-yl)-1H-pyrrole-2-carbonitrile (C9)

To a solution of 4-bromo-1-methyl-1H-pyrrole-2-carbonitrile (5.5 g, 30 mmol) and 4,4,4',4',5,5,5',5'-octamethyl-2,2'-bi-1,3,2-dioxaborolane (11.3 g, 44.5 mmol) in 1,4-dioxane (100 mL) were added [1,1'-bis(diphenylphosphino)ferrocene]dichloropalladium(II) (2.1 g, 2.9 mmol) and potassium acetate (5.7 g, 58 mmol). The reaction mixture was degassed and purged with nitrogen three times and then heated to 100° C. for 18 hours. After addition of water, the mixture was extracted with ethyl acetate (3×100 mL) and the combined organic layers were washed with saturated aqueous sodium chloride solution (100 mL), dried over sodium sulfate, filtered, and concentrated under reduced pressure. Chromatography on silica gel (Gradient: 0% to 3% ethyl acetate in petroleum ether) afforded the product as a white solid. Yield: 3.0 g, 13 mmol, 43%. $^1H$ NMR (300 MHz, $CDCl_3$) δ 7.18 (br d, J=1 Hz, 1H), 7.10 (d, J=1.5 Hz, 1H), 3.78 (s, 3H), 1.31 (s, 12H).

Step 2. Synthesis of 1-methyl-4-{1-[(4-methylphenyl)sulfonyl]-4-(morpholin-4-yl)-1H-pyrrolo[2,3-b]pyridin-3-yl}-1H-pyrrole-2-carbonitrile (C10)

To a solution of C5 (2.0 g, 4.1 mmol) and C9 (1.15 g, 4.95 mmol) in 2-methyltetrahydrofuran (20 mL) and water (8 mL) were added potassium phosphate (2.63 g, 12.4 mmol) and [1,1'-bis(diphenylphosphino)ferrocene]dichloropalladium(II), dichloromethane complex (135 mg, 0.165 mmol). The reaction mixture was degassed and purged with nitrogen three times and then heated to 70° C. for 2 hours, whereupon it was diluted with water and extracted with ethyl acetate (3×50 mL). The combined organic layers were washed with saturated aqueous sodium chloride solution (50 mL), dried over sodium sulfate, filtered, and concentrated in vacuo;

recrystallization of the residue from ethyl acetate provided the product as a red solid. Yield: 1.6 g, 3.5 mmol, 85%. $^1$H NMR (400 MHz, $CDCl_3$) δ 8.30 (d, J=5.4 Hz, 1H), 8.10 (br d, J=8.4 Hz, 2H), 7.58 (s, 1H), 7.28 (br d, J=8 Hz, 2H, assumed; partially obscured by solvent peak), 7.08 (d, J=1.5 Hz, 1H), 7.00 (d, J=1.6 Hz, 1H), 6.71 (d, J=5.5 Hz, 1H), 3.87 (s, 3H), 3.54-3.59 (m, 4H), 2.91-2.96 (m, 4H), 2.38 (s, 3H).

Step 3. Synthesis of 1-methyl-4-[4-(morpholin-4-yl)-1H-pyrrolo[2,3-b]pyridin-3-yl]-1H-pyrrole-2-carbonitrile (4)

To a solution of C10 (8.0 g, 17 mmol) in tetrahydrofuran (60 mL) was added tetrabutylammonium fluoride (13.6 g, 52.0 mmol), and the reaction mixture was stirred at 70° C. for 30 hours. The reaction mixture was diluted with water, adjusted to a pH of 10 and filtered; the filter cake was washed with water to provide the product as a yellow solid. Yield: 4.00 g, 13.0 mmol, 76%. LCMS m/z 307.9 $[M+H]^+$. $^1$H NMR (300 MHz, DMSO-$d_6$) δ 11.67 (br s, 1H), 8.08 (d, J=5.3 Hz, 1H), 7.38 (d, J=1.3 Hz, 1H), 7.36 (d, J=1.7 Hz, 1H), 7.12 (d, J=1.7 Hz, 1H), 6.63 (d, J=5.3 Hz, 1H), 3.82 (s, 3H), 3.52-3.61 (m, 4H), 2.85-2.94 (m, 4H).

Example 4A

1-($^3H_3$)Methyl-4-[4-(morpholin-4-yl)-1H-pyrrolo[2,3-b]pyridin-3-yl]-1H-pyrrole-2-carbonitrile (4A)

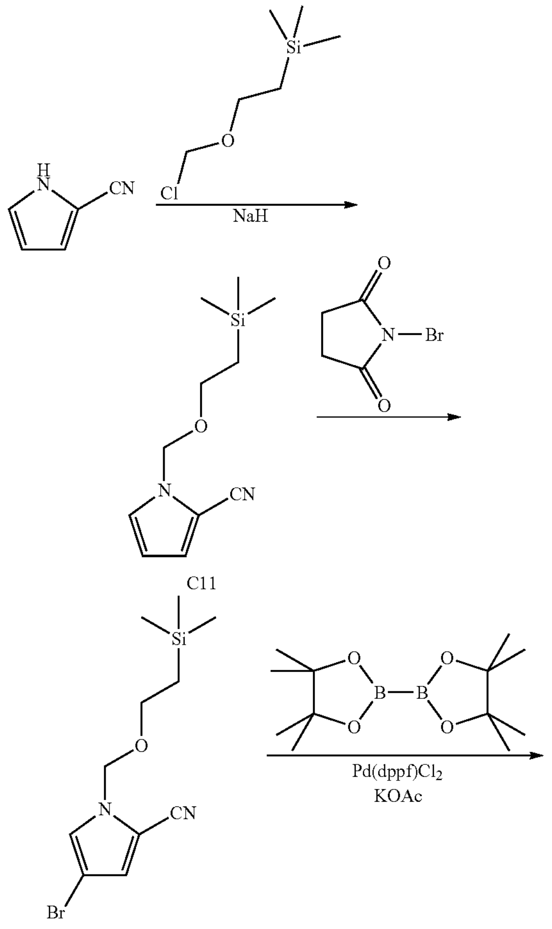

C11

C12

-continued

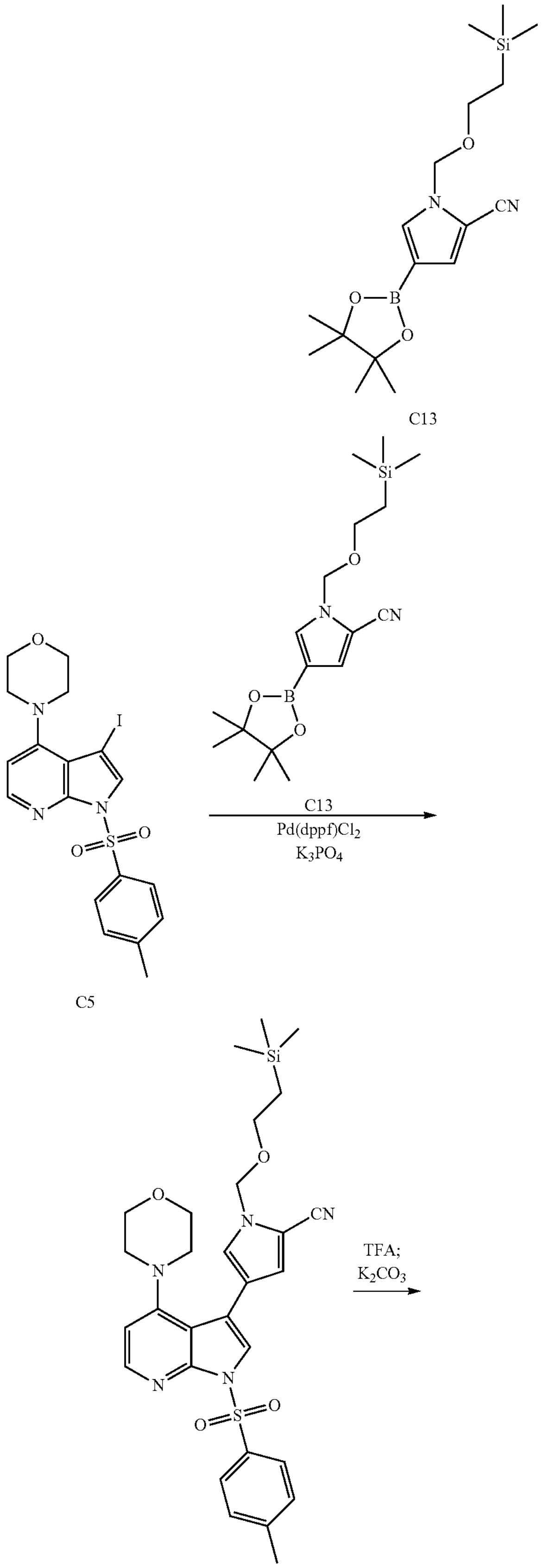

C13

C5

C14

-continued

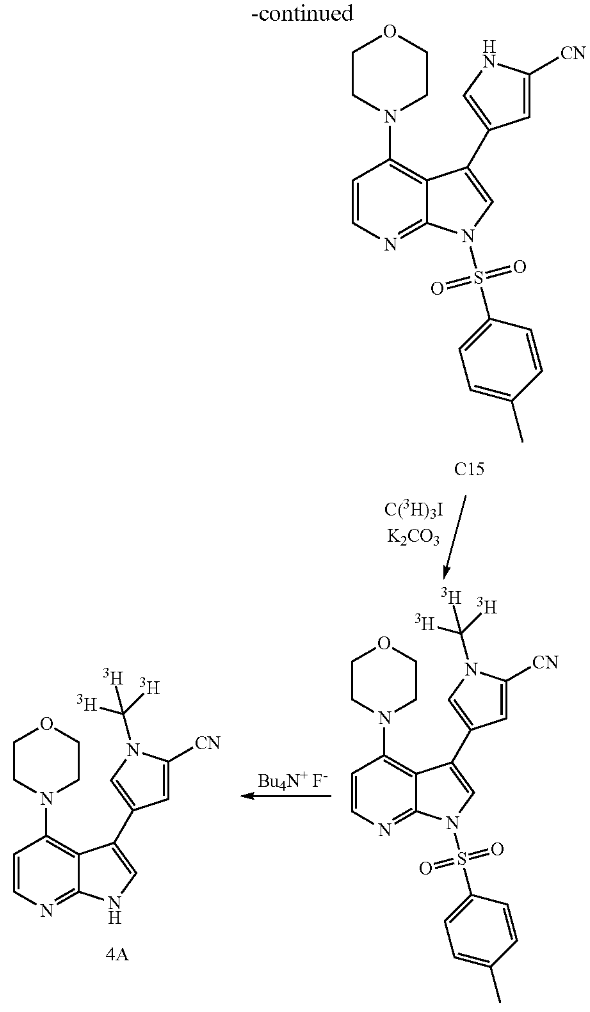

C15

C10A

4A

Step 1. Synthesis of 1-{[2-(trimethylsilyl)ethoxy]methyl}-1H-pyrrole-2-carbonitrile (C11)

A solution of 1H-pyrrole-2-carbonitrile (10.0 g, 109 mmol) in tetrahydrofuran (100 mL) was cooled to 0° C. and treated portion-wise with sodium hydride (60% in mineral oil, 6.3 g, 160 mmol. The resulting mixture was stirred at 0° C. for 30 minutes, whereupon 2-(trimethylsilyl)ethoxymethyl chloride (27.0 g, 162 mmol) was added, and the reaction mixture was allowed to warm to room temperature. After 2 hours, it was quenched with saturated aqueous sodium chloride solution (100 mL). The organic layer was dried over sodium sulfate, filtered, and concentrated in vacuo; silica gel chromatography (Eluent: 5:1 petroleum ether/ethyl acetate) afforded the product as a colorless oil. Yield: 20 g, 90 mmol, 83%. $^1$H NMR (400 MHz, $CDCl_3$) δ 7.00 (dd, J=2.8, 1.6 Hz, 1H), 6.85 (dd, J=3.9, 1.6 Hz, 1H), 6.25 (dd, J=3.9, 2.8 Hz, 1H), 5.36 (s, 2H), 3.51-3.57 (m, 2H), 0.89-0.96 (m, 2H), −0.01 (s, 9H).

Step 2. Synthesis of 4-bromo-1-{[2-(trimethylsilyl)ethoxy]methyl}-1H-pyrrole-2-carbonitrile (C12)

To a solution of C11 (10 g, 45 mmol) in dichloromethane (150 mL) was added N-bromosuccinimide (8.8 g, 49 mmol), and the reaction mixture was stirred at room temperature for 18 hours. After removal of solvent in vacuo, silica gel chromatography (Eluent: 5:1 petroleum ether/ethyl acetate) provided the product as a colorless oil. Yield: 6.0 g, 20 mmol, 44%. $^1$H NMR (400 MHz, $CDCl_3$) δ 7.00 (d, J=1.6 Hz, 1H), 6.81 (d, J=1.8 Hz, 1H), 5.31 (s, 2H), 3.51-3.57 (m, 2H), 0.89-0.96 (m, 2H), 0.00 (s, 9H).

Step 3. Synthesis of 4-(4,4,5,5-tetramethyl-1,3,2-dioxaborolan-2-yl)-1-{[2-(trimethylsilyl)ethoxy]methyl}-1H-pyrrole-2-carbonitrile (C13)

Compound C12 was converted to the product using the method described for synthesis of C9 in Example 4. The product was isolated as a white solid. Yield: 2.5 g, 7.2 mmol, 42%. $^1$H NMR (400 MHz, $CDCl_3$) δ 7.36 (d, J=1.5 Hz, 1H), 7.15 (d, J=1.5 Hz, 1H), 5.34 (s, 2H), 3.50-3.56 (m, 2H), 1.32 (s, 12H), 0.89-0.95 (m, 2H), −0.01 (s, 9H).

Step 4. Synthesis of 4-{1-[(4-methylphenyl)sulfonyl]-4-(morpholin-4-yl)-1H-pyrrolo[2,3-b]pyridin-3-yl}-1-{[2-(trimethylsilyl)ethoxy]methyl}-1H-pyrrole-2-carbonitrile (C14)

Compound C13 was reacted with C5 according to the method described for synthesis of C10 in Example 4. The product was obtained as a white solid. Yield: 500 mg, 0.87 mmol, 35%. $^1$H NMR (400 MHz, $CDCl_3$), characteristic peaks: δ 8.31 (d, J=5.4 Hz, 1H), 8.11 (br d, J=8.5 Hz, 2H), 7.61 (s, 1H), 7.06 (d, J=1.4 Hz, 1H), 6.72 (d, J=5.1 Hz, 1H), 5.41 (s, 2H), 3.62-3.67 (m, 2H), 3.55-3.60 (m, 4H), 2.92-2.96 (m, 4H), 2.39 (s, 3H), 0.96-1.02 (m, 2H), 0.03 (s, 9H).

Step 5. Synthesis of 4-{1-[(4-methylphenyl)sulfonyl]-4-(morpholin-4-yl)-1H-pyrrolo[2,3-b]pyridin-3-yl}-1H-pyrrole-2-carbonitrile (C15)

A solution of C14 (1.5 g, 2.6 mmol) was stirred at room temperature for 2 hours in trifluoroacetic acid (5 mL). The reaction mixture was concentrated to provide the crude hydroxymethyl intermediate (1.24 g) as a yellow oil; this was dissolved in acetonitrile (5 mL), treated with solid potassium carbonate until the pH was greater than 12, and allowed to stir at room temperature for 2 hours. After the reaction mixture had been filtered, the filtrate was concentrated under reduced pressure, and the residue was stirred in a 1:1 mixture of petroleum ether and ethyl acetate for 18 hours. Collection of the resulting material via filtration provided the product as a white solid. Yield: 800 mg, 1.8 mmol, 69%. LCMS m/z 448.0 [M+H]$^+$. $^1$H NMR (400 MHz, DMSO-$d_6$) δ 8.19 (d, J=5.3 Hz, 1H), 7.99 (br d, J=8.3 Hz, 2H), 7.76 (s, 1H), 7.45-7.46 (m, 1H), 7.40 (br d, J=8.5 Hz, 2H), 7.18-7.19 (m, 1H), 6.84 (d, J=5.5 Hz, 1H), 3.44-3.50 (m, 4H), 2.81-2.88 (m, 4H), 2.34 (s, 3H).

Step 6. Synthesis of 1-($^3H_3$)methyl-4-{1-[(4-methylphenyl)sulfonyl]-4-(morpholin-4-yl)-1H-pyrrolo[2,3-b]pyridin-3-yl}-1H-pyrrole-2-carbonitrile (C10A)

To a solution of C15 (10 mg, 22 μmol) in N,N-dimethylformamide (0.3 mL) was added potassium carbonate (12 mg, 87 μmol). The reaction mixture was stirred for 30 minutes at room temperature, whereupon it was injected into $^3H_3$-iodomethane (500 mCi) and stirred at room temperature for 30 minutes. Water (3 mL) was added, volatiles were removed, and the crude product was dissolved in ethyl acetate (10 mL). Analysis via reversed phase HPLC (Column: Advanced Chromatography Technologies, ACE analytical C18, 250×4.6 mm, 5 μm; Mobile phase A: 0.1% trifluoroacetic acid in water; Mobile phase B: acetonitrile; Gradient: 5% to 100% B over 15 minutes) indicated that the desired product was present. Retention time: 8 minutes. This material was taken directly into the following step. Estimated yield: 23%.

Step 7. Synthesis of 1-($^3H_3$)methyl-4-[4-(morpholin-4-yl)-1H-pyrrolo[2,3-b]pyridin-3-yl]-1H-pyrrole-2-carbonitrile (4A)

To a solution of crude C10A (from the previous step, 480 mCi) in tetrahydrofuran (2 mL) was added tetrabutylammonium fluoride (5 mg, 19 μmol) at room temperature. The reaction mixture was stirred at 70° C. for 24 hours, whereupon it was diluted with water, adjusted to pH 10, and extracted with ethyl acetate (3×5 mL). HPLC analysis of the crude material showed a conversion to product of approximately 24% (Column: Advanced Chromatography Technologies, ACE analytical C18, 250×4.6 mm, 5 μm, Mobile phase A: 0.1% trifluoroacetic acid in water; Mobile phase B: acetonitrile; Gradient: 5% to 100% B over 15 minutes). Retention time: 10.23 minutes. The crude product was purified by preparative HPLC (Column: Advanced Chromatography Technologies, ACE-5 C18 Semi-prep, 250×10 mm, 10 μm; Mobile phase A: 0.1% trifluoroacetic acid in water; Mobile phase B: acetonitrile; Gradient: 5% to 100% B over 50 min), retention time: 42 minutes. The pure fractions were pooled together and concentrated in vacuo; the product was reconstituted in ethanol. Yield=23 mCi; Radiochemical purity: >97%; Specific activity by MS: 83.99 Ci/mmol. Coinjection with 4 gave a single peak by HPLC. LCMS m/z 314.2 [M+H]$^+$.

Example 5

1-Methyl-4-[4-(morpholin-4-yl)-1H-pyrrolo[2,3-b]pyridin-3-yl]-1H-imidazole-2-carbonitrile (5)

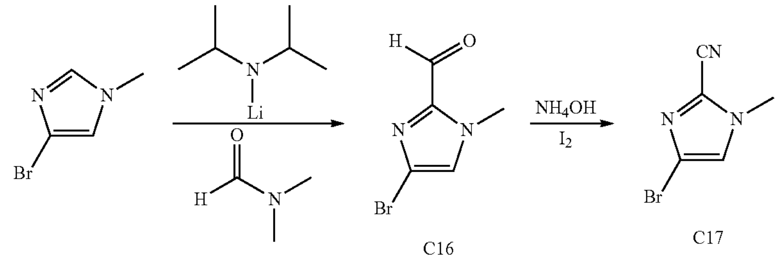

C16 C17

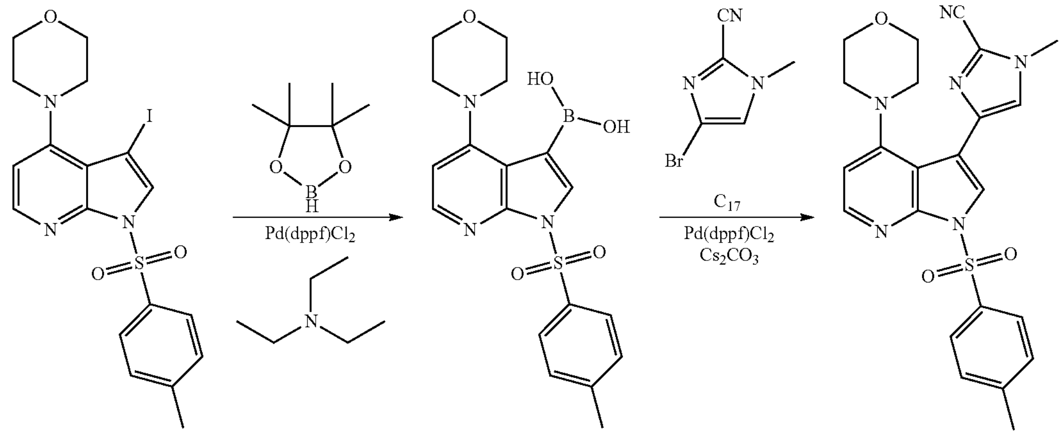

C5 C18 C19

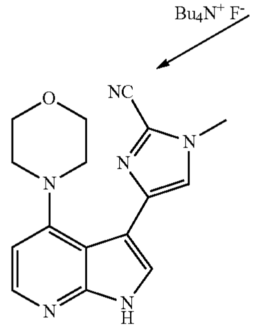

5

Step 1. Synthesis of 4-bromo-1-methyl-1H-imidazole-2-carbaldehyde (C16)

Lithium diisopropylamide (2 M solution in heptane/tetrahydrofuran/ethylbenzene, 24 mL, 48 mmol) was added to a −10° C. solution of 4-bromo-1-methyl-1H-imidazole (7.0 g, 43 mmol) in tetrahydrofuran (250 mL). After 1 hour, N,N-dimethylformamide (4.8 g, 66 mmol) was added at 0° C., and the reaction mixture was stirred for an additional hour. Saturated aqueous citric acid solution (50 mL) was then added, and the organic layer was dried over sodium sulfate, filtered, and concentrated in vacuo to afford the product as a yellow solid. This material was used in the following step without further purification. Yield: 7.0 g, 37 mmol, 86%. $^1$H NMR (400 MHz, DMSO-$d_6$) δ 9.61 (s, 1H), 7.77 (s, 1H), 3.92 (s, 3H).

Step 2. Synthesis of 4-bromo-1-methyl-1H-imidazole-2-carbonitrile (C17)

A solution of C16 (7.0 g, 37 mmol) and iodine (12.1 g, 47.7 mmol) in aqueous ammonium hydroxide (100 mL) and tetrahydrofuran (30 mL) was stirred at room temperature for 1 hour. The reaction was quenched by addition of aqueous sodium sulfite solution (50 mL) and extracted with ethyl acetate (3×50 mL); the combined organic layers were washed with saturated aqueous sodium chloride solution (200 mL), dried over sodium sulfate, filtered, and concentrated in vacuo. Silica gel chromatography (Gradient: 0% to 40% ethyl acetate in petroleum ether) afforded the product as an off-white solid. Yield: 4.0 g, 22 mmol, 59%. LCMS m/z 185.6 [M+H]$^+$. $^1$H NMR (400 MHz, DMSO-$d_6$) δ 7.79 (s, 1H), 3.82 (s, 3H).

Step 3. Synthesis of {1-[(4-methylphenyl)sulfonyl]-4-(morpholin-4-yl)-1H-pyrrolo[2,3-b]pyridin-3-yl}boronic acid (C18)

Compound C17 was converted to the product in nine batches, using the method described for synthesis of C7 in Example 3. The product was obtained as a white solid. Yield: 2.5 g, 6.2 mmol, 33%. $^1$H NMR (400 MHz, DMSO-$d_6$) δ 8.69 (s, 2H), 8.27 (d, J=5.4 Hz, 1H), 8.04 (s, 1H), 8.01 (br d, J=8.4 Hz, 2H), 7.41 (br d, J=8.3 Hz, 2H), 7.10 (d, J=5.4 Hz, 1H), 3.75-3.82 (m, 4H), 2.98-3.05 (m, 4H), 2.34 (s, 3H).

Step 4. Synthesis of 1-methyl-4-{1-[(4-methylphenyl)sulfonyl]-4-(morpholin-4-yl)-1H-pyrrolo[2,3-b]pyridin-3-yl}-1H-imidazole-2-carbonitrile (C19)

Compound C17 (580 mg, 3.12 mmol), cesium carbonate (2.4 g, 7.4 mmol) and [1,1'-bis(diphenylphosphino)ferrocene]dichloropalladium(II) (271 mg, 0.370 mmol) were added to a solution of C18 (1.5 g, 3.7 mmol) in 1,4-dioxane (15 mL) and water (2 mL). The reaction mixture was degassed and purged with nitrogen several times, stirred for 3 hours at 100° C., and partitioned between water (50 mL) and ethyl acetate (50 mL). The aqueous layer was extracted with ethyl acetate (3×30 mL), and the combined organic layers were dried over sodium sulfate, filtered, and concentrated under reduced pressure. Chromatography on silica gel (Gradient: 0% to 50% ethyl acetate in petroleum ether) provided the product as a yellow solid. Yield: 1.0 g, 2.2 mmol, 59%. $^1$H NMR (400 MHz, $CDCl_3$) δ 8.32 (d, J=5.5 Hz, 1H), 8.09 (br d, J=8.4 Hz, 2H), 7.96 (s, 1H), 7.51 (s, 1H), 7.27 (br d, J=8.0 Hz, 2H), 6.75 (d, J=5.5 Hz, 1H), 3.97 (s, 3H), 3.59-3.64 (m, 4H), 2.94-2.99 (m, 4H), 2.38 (s, 3H).

Step 5. Synthesis of 1-methyl-4-[4-(morpholin-4-yl)-1H-pyrrolo[2,3-b]pyridin-3-yl]-1H-imidazole-2-carbonitrile (5)

Compound C19 (1.0 g, 2.2 mmol) was mixed with a solution of tetrabutylammonium fluoride in tetrahydrofuran (1 M, 6.5 mL, 6.5 mmol) and heated at 50° C. for 18 hours. The reaction mixture was then poured into water (6.5 mL), adjusted to a pH of 8 with 1 M aqueous sodium hydroxide solution, and filtered. The filter cake was washed with a mixture of petroleum ether and ethyl acetate (5:1, 20 mL) to afford the product as a yellow solid. Yield: 570 mg, 1.85 mmol, 84%. LCMS m/z 308.9 [M+H]$^+$. $^1$H NMR (400 MHz, DMSO-$d_6$) δ 11.85 (br s, 1H), 8.11 (d, J=5.3 Hz, 1H), 7.77 (s, 1H), 7.54 (s, 1H), 6.68 (d, J=5.3 Hz, 1H), 3.94 (s, 3H), 3.56-3.64 (m, 4H), 2.86-2.94 (m, 4H).

Example 6

1-Methyl-4-[4-(morpholin-4-yl)-7H-pyrrolo[2,3-c]pyridazin-5-yl]-1H-pyrrole-2-carbonitrile (6)

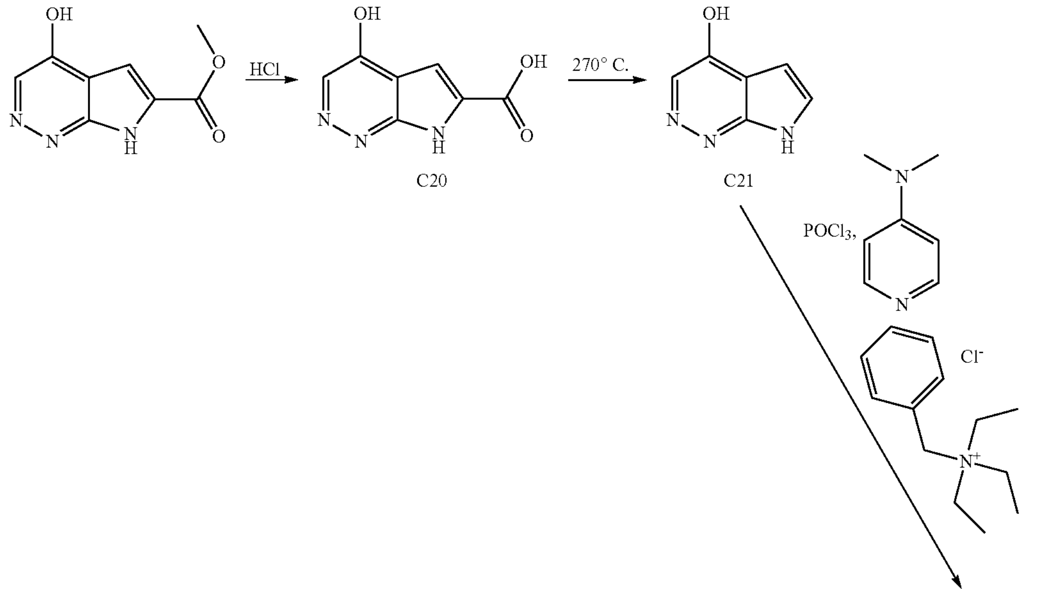

C20
C21

-continued

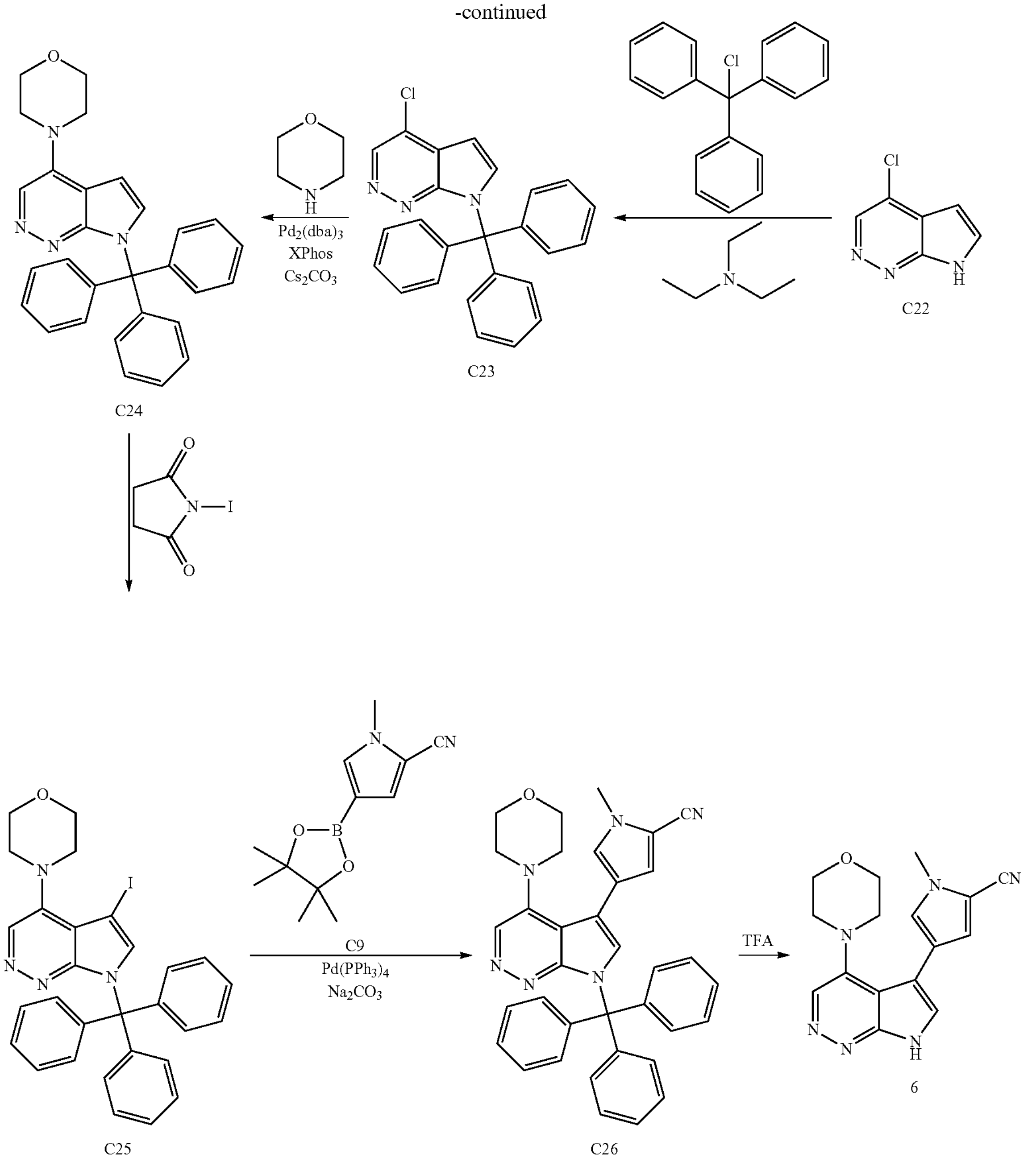

C24 C23 C22 C25 C26 6

Step 1. Synthesis of 4-hydroxy-7H-pyrrolo[2,3-c]pyridazine-6-carboxylic acid (C20)

A solution of methyl 4-hydroxy-7H-pyrrolo[2,3-c]pyridazine-6-carboxylate (which may be prepared using the method described by Y. S. Babu et al., PCT Int. Appl. WO 2011/031554, Mar. 17, 2011) (35 g, 0.18 mol) in aqueous hydrochloric acid (6 M, 350 mL) was heated at 120° C. for 18 hours. The reaction mixture was concentrated in vacuo to provide the product as a gray solid. Yield: 28.0 g, 0.156 mol, 87%. $^1$H NMR (400 MHz, DMSO-$d_6$) δ 13.63 (br s, 1H), 8.57 (br s, 1H), 7.48 (s, 1H).

Step 2. Synthesis of 7H-pyrrolo[2,3-c]pyridazin-4-ol (C21)

Tetrahydrothiophene 1,1-dioxide (sulfolane, 50 mL) was heated to 270° C. Compound C20 (13.0 g, 72.6 mmol) was added portion-wise to the hot solvent; the reaction mixture was maintained at 270° C. for 15 minutes, then immediately cooled to room temperature. Purification via silica gel chromatography (Gradient: 1% to 17% methanol in dichloromethane) afforded the product as a yellow solid. Yield: 7.5 g, 56 mmol, 77%. $^1$H NMR (400 MHz, DMSO-$d_6$) δ 12.34 (br s, 1H), 8.10 (br s, 1H), 7.51 (br s, 1H), 6.63 (d, J=3.3 Hz, 1H).

Step 3. Synthesis of 4-chloro-7H-pyrrolo[2,3-c]pyridazine (C22)

4-(Dimethylamino)pyridine (21.6 g, 177 mmol), benzyltriethylammonium chloride (40.0 g, 176 mmol) and phosphorus oxychloride (160 g, 1.04 mol) were added to a suspension of C21 (16.0 g, 118 mmol) in acetonitrile (240 mL), and the reaction mixture was heated at 80° C. for 2 hours. It was then poured into ice water and adjusted to a pH of 7-8 via addition of saturated aqueous sodium bicarbonate solution. The mixture was extracted with ethyl acetate (6×200 mL), and the combined organic layers were dried over sodium sulfate, filtered, and concentrated in vacuo to provide the product as a gray solid. Yield: 9.5 g, 62 mmol, 53%. $^1$H NMR (400 MHz, DMSO-$d_6$) δ 12.85 (br s, 1H), 8.98 (s, 1H), 8.04 (dd, J=3.3, 2.6 Hz, 1H), 6.65 (dd, J=3.3, 1.6 Hz, 1H).

Step 4. Synthesis of 4-chloro-7-trityl-7H-pyrrolo[2,3-c]pyridazine (C23)

To a solution of C22 (1.0 g, 6.5 mmol) in dichloromethane (50 mL) were added triethylamine (990 mg, 9.8 mmol) and triphenylmethyl chloride (trityl chloride, 3.6 g, 13 mmol). The reaction mixture was stirred at room temperature for 18 hours, whereupon it was diluted with water (50 mL) and extracted with dichloromethane (3×50 mL). The combined organic layers were washed with saturated aqueous sodium chloride solution (100 mL), dried over sodium sulfate, filtered, and concentrated under reduced pressure. Silica gel chromatography (Gradient: 0% to 17% ethyl acetate in petroleum ether) afforded the product as a white solid. Yield: 1.3 g, 3.3 mmol, 51%.

Step 5. Synthesis of 4-(morpholin-4-yl)-7-trityl-7H-pyrrolo[2,3-c]pyridazine (C24)

To a mixture of C23 (1.5 g, 3.8 mmol), morpholine (645 mg, 7.40 mmol), and cesium carbonate (2.5 g, 7.7 mmol) in tert-butanol (60 mL) were added 2-dicyclohexylphosphino-2',4',6'-triisopropylbiphenyl (XPhos, 181 mg, 0.380 mmol) and tris(dibenzylideneacetone)dipalladium(0) (347 mg, 0.379 mmol). The reaction mixture was degassed and purged with nitrogen three times, then heated at 125° C. for 18 hours. After removal of solvent in vacuo, the residue was diluted with water (50 mL) and extracted with ethyl acetate (3×50 mL); the combined organic layers were washed with saturated aqueous sodium chloride solution (50 mL), dried over sodium sulfate, filtered, and concentrated under reduced pressure. Chromatography on silica gel (Gradient: 0% to 50% ethyl acetate in petroleum ether) provided the product as a yellow solid. Yield: 1.0 g, 2.2 mmol, 58%. $^1$H NMR (400 MHz, $CDCl_3$) δ 8.40 (s, 1H), 7.33 (d, J=3.9 Hz, 1H), 7.21-7.29 (m, 15H), 6.44 (d, J=3.9 Hz, 1H), 3.89-3.93 (m, 4H), 3.49-3.54 (m, 4H).

Step 6. Synthesis of 5-iodo-4-(morpholin-4-yl)-7-trityl-7H-pyrrolo[2,3-c]pyridazine (C25)

To a solution of C24 (500 mg, 1.12 mmol) in dichloromethane (50 mL) was added N-iodosuccinimide (1.25 g, 4.44 mmol). The mixture was stirred at room temperature for 18 hours, whereupon it was concentrated in vacuo. Chromatography on silica gel (Gradient: 0% to 50% ethyl acetate in petroleum ether) provided the product as a yellow solid. Yield: 200 mg, 0.35 mmol, 31%. $^1$H NMR (400 MHz, $CDCl_3$) δ 8.32 (s, 1H), 7.71 (s, 1H), 7.26-7.34 (m, 15H), 3.97-4.02 (m, 4H), 3.27-3.32 (m, 4H).

Step 7. Synthesis of 1-methyl-4-[4-(morpholin-4-yl)-7-trityl-7H-pyrrolo[2,3-c]pyridazin-5-yl]-1H-pyrrole-2-carbonitrile (C26)

Reaction of C25 with C9 was carried out using the method described for synthesis of C6 in Example 2. In this case, purification was carried out via preparative thin layer chromatography (Eluent: 1:1 petroleum ether/ethyl acetate) to afford the product as a yellow oil, which was taken directly to the following step. Yield: 90 mg, 0.16 mmol, 31%. LCMS m/z 551.3 $[M+H]^+$.

Step 8. Synthesis of 1-methyl-4-[4-(morpholin-4-yl)-7H-pyrrolo[2,3-c]pyridazin-5-yl]-1H-pyrrole-2-carbonitrile (6)

A mixture of C26 (90 mg, 0.16 mmol) in trifluoroacetic acid (5 mL) and dichloromethane (5 mL) was stirred at room temperature for 18 hours. The pH of the reaction mixture was then adjusted to 5-6 by addition of saturated aqueous sodium bicarbonate solution; the resulting mixture was extracted with dichloromethane (3×10 mL), and the combined organic layers were washed with saturated aqueous sodium chloride solution (25 mL), dried over sodium sulfate, filtered, and concentrated in vacuo. Purification via reversed phase HPLC (Column: Phenomenex Gemini C18, 8 μm; Mobile phase A: aqueous ammonia, pH 10; Mobile phase B: acetonitrile; Gradient: 20% to 44% B) provided the product as a yellow solid. Yield: 6.6 mg, 21 μmol, 13%. LCMS m/z 309.1 $[M+H]^+$. $^1$H NMR (400 MHz, DMSO-$d_6$) δ 8.58 (s, 1H), 7.75 (s, 1H), 7.40-7.43 (m, 1H), 7.15 (d, J=1.6 Hz, 1H), 3.83 (s, 3H), 3.59-3.64 (m, 4H), 2.99-3.04 (m, 4H).

Example 7

4-[2-Chloro-4-(morpholin-4-yl)-1H-pyrrolo[2,3-b]pyridin-3-yl]-1-methyl-1H-pyrrole-2-carbonitrile (7)

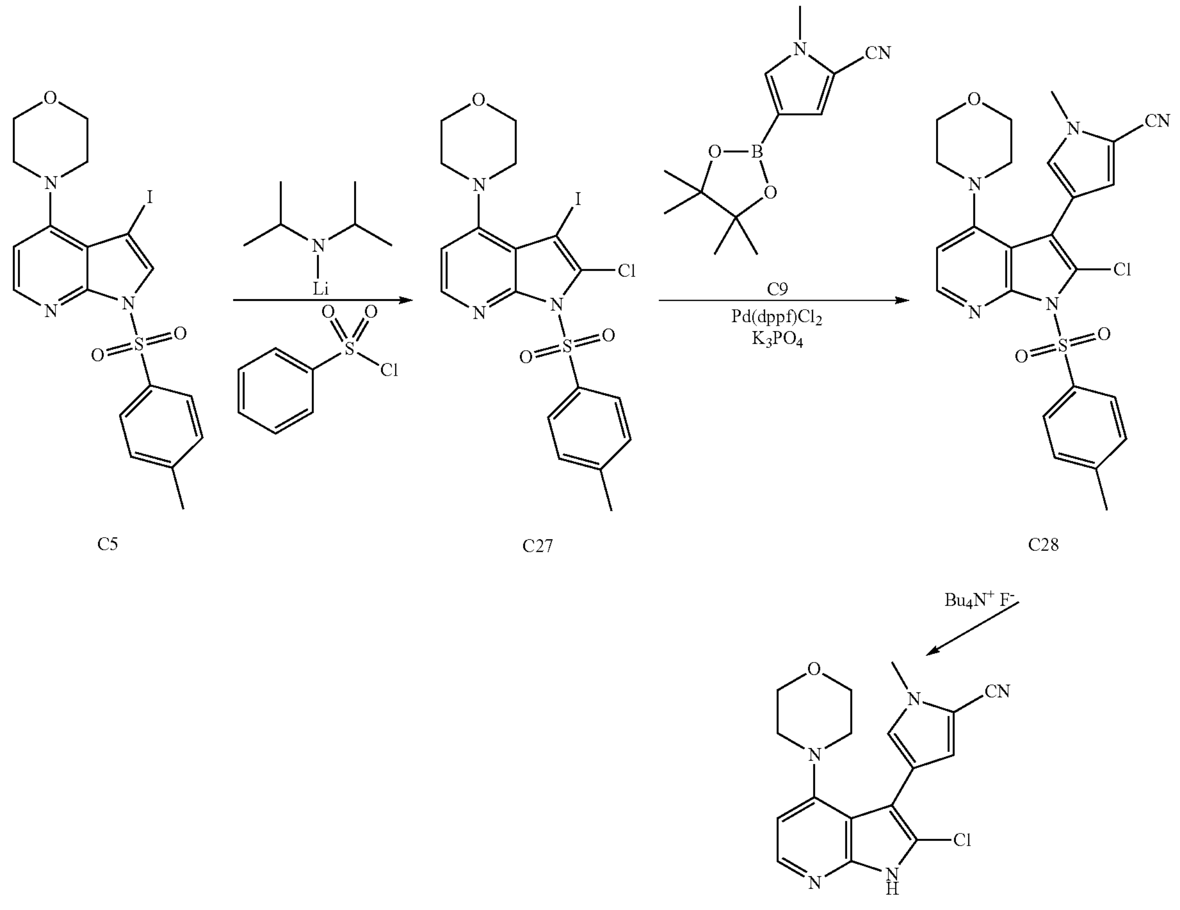

C5 C27 C28

7

Step 1. Synthesis of 2-chloro-3-iodo-1-[(4-methylphenyl)sulfonyl]-4-(morpholin-4-yl)-1H-pyrrolo[2,3-b]pyridine (C27)

To a −78° C. solution of diisopropylamine (60 mg, 0.59 mmol) in tetrahydrofuran (15 mL) was added n-butyllithium (2.5 M solution, 240 uL, 0.60 mmol), followed by a solution of C5 (200 mg, 0.41 mmol) in tetrahydrofuran (15 mL). The reaction mixture was stirred at −78° C. for 1 hour, whereupon benzenesulfonyl chloride (100 mg, 0.57 mmol) was introduced drop-wise. The reaction mixture was then allowed to warm to room temperature and stir for 18 hours. After being quenched with water (80 mL), it was extracted with dichloromethane (3x30 mL), and the combined organic layers were washed with saturated aqueous sodium chloride solution (300 mL), dried over sodium sulfate, filtered, and concentrated in vacuo. Purification via silica gel chromatography (Gradient: 5% to 50% ethyl acetate in petroleum ether) afforded the product as a yellow solid. Yield: 100 mg, 0.19 mmol, 46%. $^{1}H$ NMR (400 MHz, $CDCl_3$) δ 8.34 (d, J=5.5 Hz, 1H), 8.11 (br d, J=8.4 Hz, 2H), 7.30 (br d, J=8.5 Hz, 2H), 6.80 (d, J=5.5 Hz, 1H), 3.95-4.01 (m, 4H), 3.07-3.17 (m, 4H), 2.40 (s, 3H).

Step 2. Synthesis of 4-{2-chloro-1-[(4-methylphenyl)sulfonyl]-4-(morpholin-4-yl)-1H-pyrrolo[2,3-b]pyridin-3-yl}-1-methyl-1H-pyrrole-2-carbonitrile (C28)

Compound C27 (100 mg, 0.19 mmol) was converted to the product using the method described for synthesis of C10 in Example 4. In this case, purification was effected by preparative thin layer chromatography (Eluent: 1:1 ethyl acetate/petroleum ether). The product was isolated as a yellow solid (50 mg), which was used directly in the next step. Yield: 50 mg, ≤0.10 mmol, ≤53%.

Step 3. Synthesis of 4-[2-chloro-4-(morpholin-4-yl)-1H-pyrrolo[2,3-b]pyridin-3-yl]-1-methyl-1H-pyrrole-2-carbonitrile (7)

A solution of C28 (from the previous step, 50 mg, 13.10 mmol) in tetrabutylammonium fluoride (1 M solution in tetrahydrofuran, 3 mL, 3 mmol) was stirred at 60° C. for 1 hour. The reaction mixture was concentrated in vacuo and purified by preparative thin layer chromatography (Eluent: 1:1 petroleum ether/ethyl acetate) and then by reversed phase HPLC (Column: Phenomenex Gemini C18, 8 μm; Mobile phase A: water containing 0.225% formic acid; Mobile phase B: acetonitrile; Gradient: 17% to 37% B) to afford the product as a white solid. Yield: 4.0 mg, 12 μmol, 6% over 2 steps. LCMS m/z 341.9 $[M+H]^+$. $^1H$ NMR (400 MHz, DMSO-$d_6$) δ 8.08 (d, J=5.4 Hz, 1H), 7.35 (d, J=1.9 Hz, 1H), 7.07 (d, J=1.9 Hz, 1H), 6.65 (d, J=5.5 Hz, 1H), 3.85 (s, 3H), 3.4-3.46 (m, 4H, assumed; partially obscured by water peak), 2.81-2.87 (m, 4H).

Example 8

3-[2-Methyl-4-(morpholin-4-yl)-1H-pyrrolo[2,3-b]pyridin-3-yl]benzonitrile, trifluoroacetate salt (8)

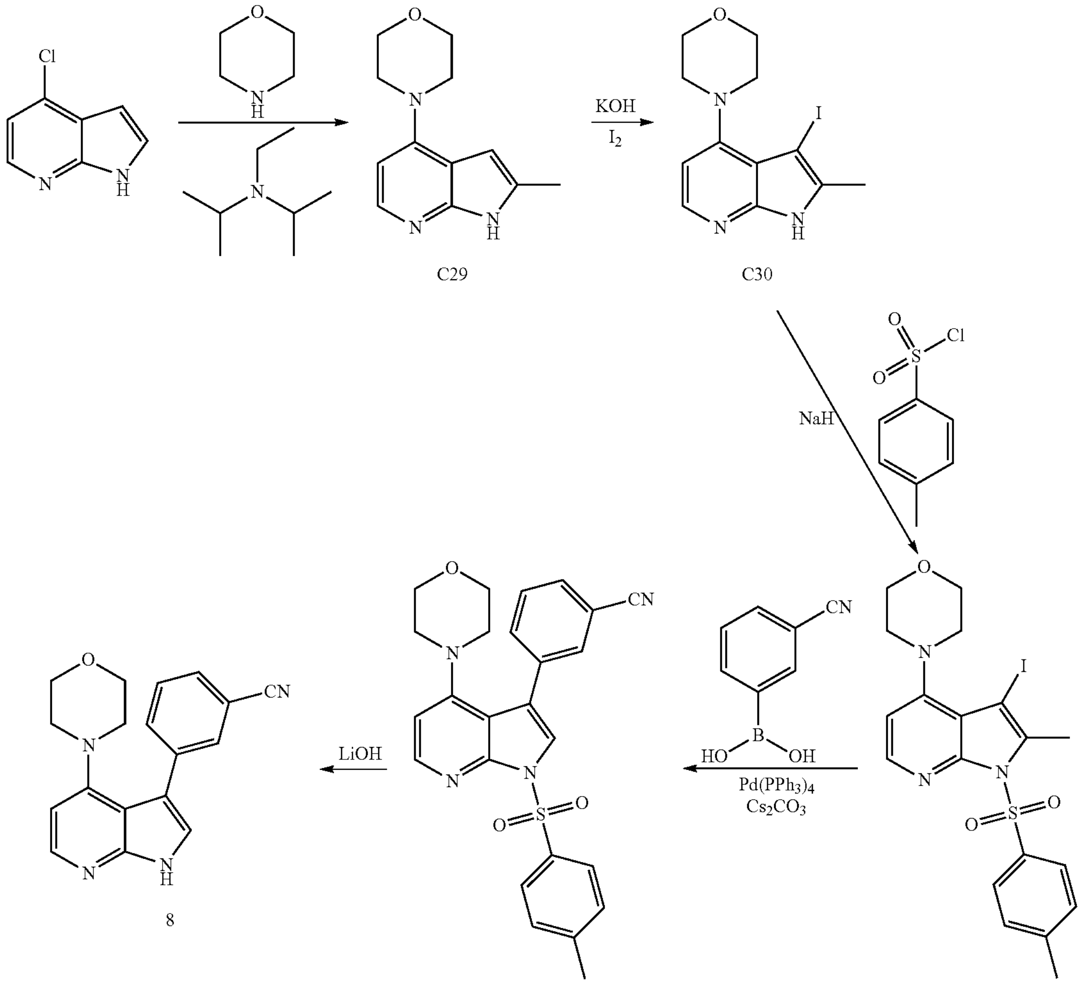

C29 C30 C31 C32 8

Step 1. Synthesis of 2-methyl-4-(morpholin-4-yl)-1H-pyrrolo[2,3-b]pyridine (C29)

Morpholine (1.0 g, 11 mmol) and N,N-diisopropylethylamine (2 mL) were added to a mixture of 4-chloro-2-methyl-1H-pyrrolo[2,3-b]pyridine (1.0 g, 6.0 mmol) in 1-methylpyrrolidin-2-one (15 mL). The reaction mixture was heated at 170° C. for 3 hours in a microwave reactor, then diluted with water (30 mL) and extracted with ethyl acetate (2×50 mL). The combined organic layers were washed with saturated aqueous sodium chloride solution (50 mL), dried over sodium sulfate, filtered, and concentrated in vacuo; chromatography on silica gel (Gradient: 0% to 50% ethyl acetate in petroleum ether) provided the product as a white solid. Yield: 1.0 g, 4.6 mmol, 77%. $^1H$ NMR (400 MHz, DMSO-$d_6$) δ 11.24 (br s, 1H), 7.86 (d, J=5.4 Hz, 1H), 6.38 (d, J=5.5 Hz, 1H), 6.15-6.17 (m, 1H), 3.74-3.79 (m, 4H), 3.26-3.31 (m, 4H), 2.33 (br s, 3H).

Step 2. Synthesis of 3-iodo-2-methyl-4-(morpholin-4-yl)-1H-pyrrolo[2,3-b]pyridine (C30)

To a −20° C. mixture of C29 (1.0 g, 4.6 mmol) in N,N-dimethylformamide (30 mL) was added potassium hydroxide (770 mg, 13.7 mmol). A solution of iodine (1.2 g, 4.7 mmol) in N,N-dimethylformamide (5 mL) was introduced, and the reaction mixture was stirred at −20° C. for 3 hours, then poured into ice water. The product, a white solid, was isolated via filtration. Yield: 0.70 g, 2.0 mmol, 43%. $^1H$ NMR (400 MHz, DMSO-$d_6$) δ 11.98 (br s, 1H), 8.01 (d, J=5.0 Hz, 1H), 6.63 (d, J=5.3 Hz, 1H), 3.84-3.92 (m, 4H), 3.02-3.11 (m, 4H), 2.36 (s, 3H).

Step 3. Synthesis of 3-iodo-2-methyl-1-[(4-methylphenyl)sulfonyl]-4-(morpholin-4-yl)-1H-pyrrolo[2,3-b]pyridine (C31)

A solution of C30 (6.0 g, 17 mmol) in tetrahydrofuran (50 mL) was added in a drop-wise manner to a suspension of sodium hydride (60% in mineral oil, 1.4 g, 35 mmol) in tetrahydrofuran (100 mL) at 0° C. After completion of the addition, the reaction mixture was allowed to stir at 0° C. for a further 30 minutes, whereupon p-toluenesulfonyl chloride (4.0 g, 21 mmol) was added in portions, at a rate that maintained the reaction temperature at approximately 5° C. The reaction mixture was then allowed to stir at 10° C. for 5 hours, at which time it was partitioned between saturated aqueous sodium bicarbonate solution (1.5 L) and ethyl acetate (150 mL). The aqueous layer was extracted with ethyl acetate (3×150 mL), and the combined organic layers were washed with saturated aqueous sodium chloride solution (100 mL), dried over sodium sulfate, filtered, and concentrated in vacuo. Chromatography on silica gel (Eluent: 3:1 petroleum ether/ethyl acetate) afforded the product as a yellow solid. Yield: 3.91 g, 7.86 mmol, 46%. LCMS m/z 498.1 $[M+H]^+$. $^1H$ NMR (400 MHz, DMSO-$d_6$) δ 8.15 (d, J=5.4 Hz, 1H), 7.97-8.02 (m, 2H), 7.37-7.41 (m, 2H), 6.87 (d, J=5.5 Hz, 1H), 3.82-3.87 (m, 4H), 2.98-3.04 (m, 4H), 2.78 (s, 3H), 2.33 (s, 3H).

Step 4. Synthesis of 3-{2-methyl-1-[(4-methylphenyl)sulfonyl]-4-(morpholin-4-yl)-1H-pyrrolo[2,3-b]pyridin-3-yl}benzonitrile (C32)

Compound C31 (100 mg, 0.20 mmol) was converted to the product using the method described for synthesis of C2 in Example 1. In this case, the crude product, a yellow solid, was used directly in the following step.

Step 5. Synthesis of 3-[2-methyl-4-(morpholin-4-yl)-1H-pyrrolo[2,3-b]pyridin-3-yl]benzonitrile, trifluoroacetate salt (8)

To a stirred solution of C32 (from the previous step, 0.20 mmol) in acetonitrile (20 mL) was added potassium hydroxide (28 mg, 0.50 mmol), and the reaction mixture was heated at 50° C. for 5 hours. Purification via reversed phase HPLC (Column: DIKMA Diamonsil(2) C18, 5 μm; Mobile phase A: water containing 0.225% trifluoroacetic acid; Mobile phase B: acetonitrile; Gradient: 10% to 30% B) afforded the product as a white solid. Yield: 4.0 mg, 9.2 μmol, 5% over 2 steps. LCMS m/z 319.1 $[M+H]^+$. $^1H$ NMR (400 MHz, DMSO-$d_6$), characteristic peaks: δ 11.80 (br s, 1H), 8.05 (d, J=5.5 Hz, 1H), 7.72-7.80 (m, 3H), 7.64 (dd, J=8.0, 7.5 Hz, 1H), 6.64 (d, J=5.0 Hz, 1H), 2.72-2.77 (m, 4H), 2.35 (s, 3H).

Example 9

3-[6-Methyl-4-(morpholin-4-yl)-1H-pyrrolo[2,3-b]pyridin-3-yl]benzonitrile (9)

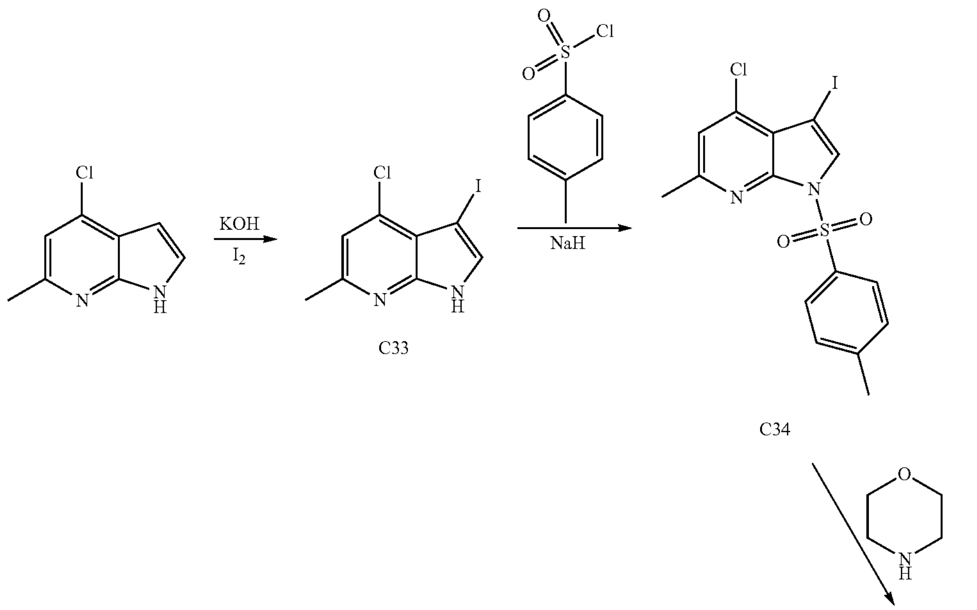

C33

C34

-continued

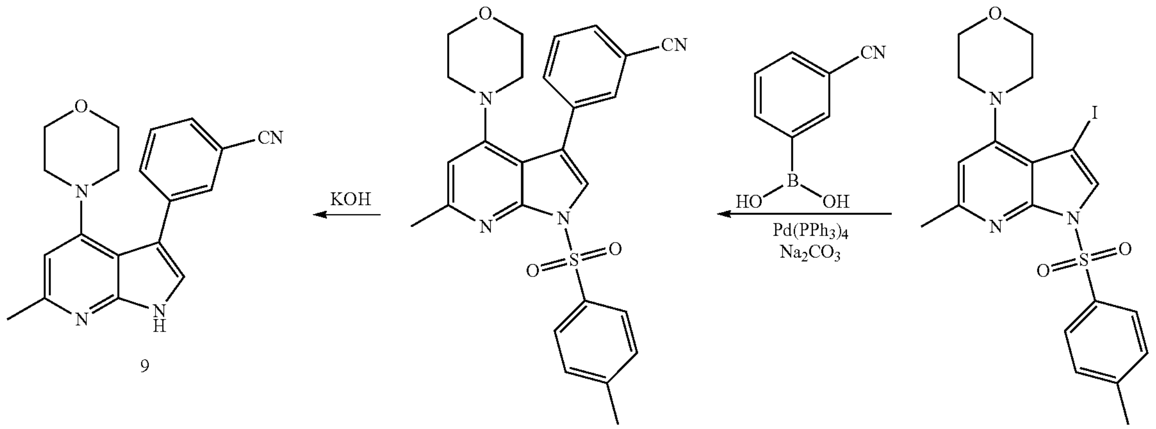

9 C36 C35

Step 1. Synthesis of 4-chloro-3-iodo-6-methyl-1H-pyrrolo[2,3-b]pyridine (C33)

To a 0° C. suspension of 4-chloro-6-methyl-1H-pyrrolo[2,3-b]pyridine (1.7 g, 10 mmol) in N,N-dimethylformamide (20 mL) was added potassium hydroxide (1.14 g, 20.3 mmol), followed by iodine (2.54 g, 10.0 mmol). The reaction mixture was allowed to warm to room temperature and stir for 4 hours, whereupon it was diluted with water and filtered, to afford the product as a white solid. Yield: 1.6 g, 5.5 mmol, 55%. $^{1}H$ NMR (400 MHz, $CD_3OD$) δ 7.47 (s, 1H), 7.04 (s, 1H), 2.54 (s, 3H)

Step 2. Synthesis of 4-chloro-3-iodo-6-methyl-1-[(4-methylphenyl)sulfonyl]-1H-pyrrolo[2,3-b]pyridine (C34)

Sodium hydride (60% in mineral oil, 438 mg, 11.0 mmol) was added to a 0° C. suspension of C33 (1.6 g, 5.5 mmol) in tetrahydrofuran (20 mL). After 20 minutes, p-toluenesulfonyl chloride (1.56 g, 8.18 mmol) was added to the 0° C. reaction mixture; it was then allowed to warm to room temperature and stir for 18 hours. Water was added, and the mixture was extracted with ethyl acetate (3×50 mL); the combined organic layers were washed with saturated aqueous sodium chloride solution (50 mL), dried over sodium sulfate, filtered, and concentrated in vacuo. Purification via silica gel chromatography provided the product as a white solid. Yield: 1.28 g, 2.87 mmol, 52%.

Step 3. Synthesis of 3-iodo-6-methyl-1-[(4-methylphenyl)sulfonyl]-4-(morpholin-4-yl)-1H-pyrrolo[2,3-b]pyridine (C35)

Compound C34 was reacted with morpholine using the method described for synthesis of 1 in Example 1. The product was obtained as a white solid. Yield: 600 mg, 1.2 mmol, 42%. LCMS m/z 498.1 $[M+H]^+$.

Step 4. Synthesis of 3-{6-methyl-1-[(4-methylphenyl)sulfonyl]-4-(morpholin-4-yl)-1H-pyrrolo[2,3-b]pyridin-3-yl}benzonitrile (C36)

Compound C35 was reacted with (3-cyanophenyl)boronic acid using the method described for synthesis of C6 in Example 2. In this case purification was carried out via preparative thin layer chromatography, providing the product as a yellow solid. Yield: 50 mg, 0.11 mmol, 55%. LCMS m/z 473.2 $[M+H]^+$.

Step 5. Synthesis of 3-[6-methyl-4-(morpholin-4-yl)-1H-pyrrolo[2,3-b]pyridin-3-yl]benzonitrile (9)

To a solution of C36 (50 mg, 0.11 mmol) in 1,4-dioxane (3 mL) was added potassium hydroxide (12 mg, 0.21 mmol). The reaction mixture was stirred at 30° C. for 4 hours, then filtered and concentrated under reduced pressure. Reversed phase HPLC (Column: Phenomenex Gemini C18, 5 μm; Mobile phase A: aqueous ammonia, pH 10; Mobile phase B: acetonitrile; Gradient: 28% to 48% B) afforded the product as a white solid. Yield: 7.0 mg, 22 μmol, 20%. LCMS m/z 319.1 $[M+H]^+$. $^{1}H$ NMR (400 MHz, $CDCl_3$) δ 9.8 (br s, 1H), 7.94-7.96 (m, 1H), 7.83-7.87 (m, 1H), 7.57-7.61 (m, 1H), 7.53 (dd, J=8, 8 Hz, 1H), 7.23 (s, 1H), 6.57 (s, 1H), 3.47-3.53 (m, 4H), 2.92-2.97 (m, 4H), 2.65 (s, 3H).

Example 10

3-[5-(Hydroxymethyl)-4-(morpholin-4-yl)-1H-pyrrolo[2,3-b]pyridin-3-yl]benzonitrile (10)

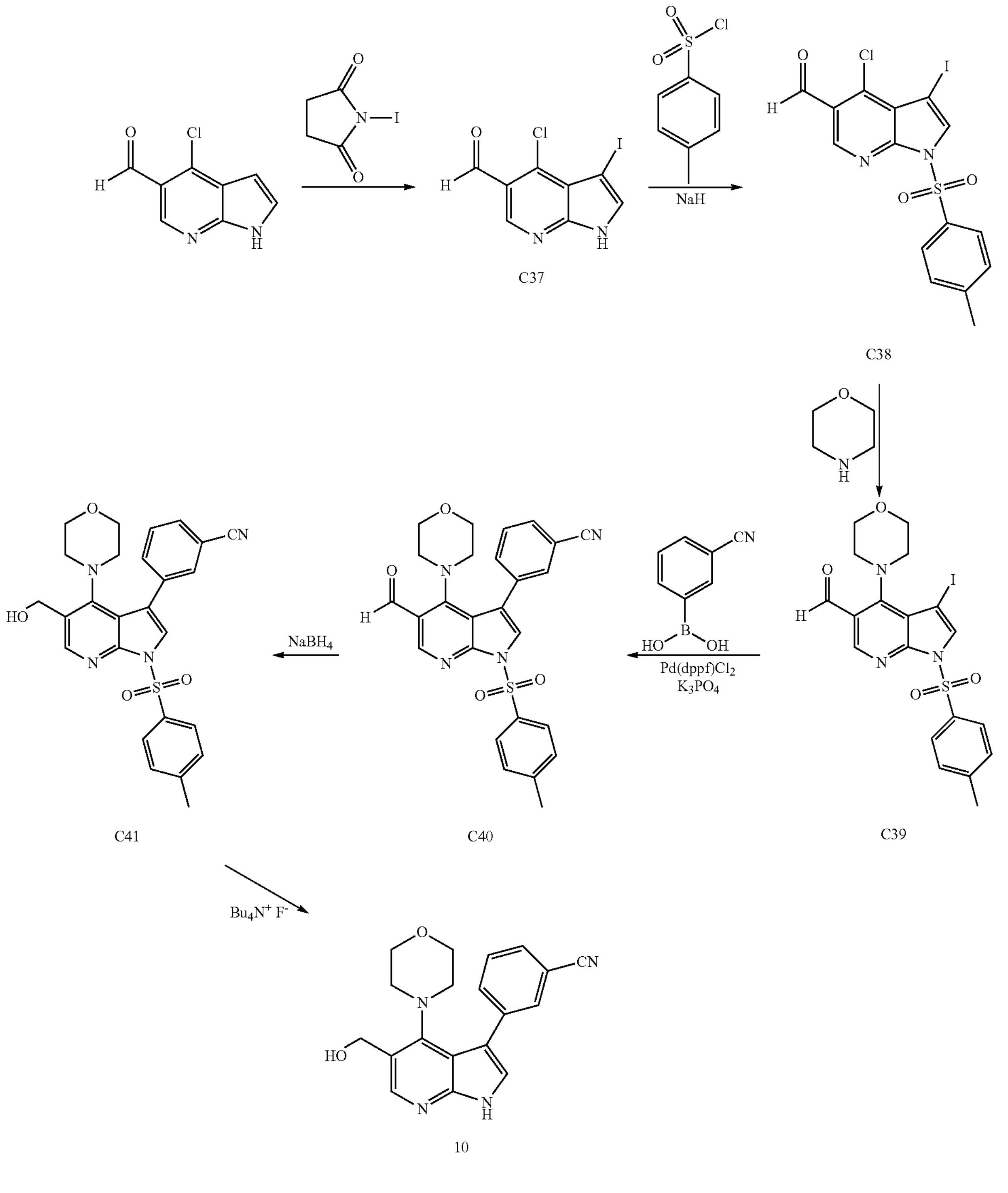

Step 1. Synthesis of 4-chloro-3-iodo-1H-pyrrolo[2,3-b]pyridine-5-carbaldehyde (C37)

A solution of 4-chloro-1H-pyrrolo[2,3-b]pyridine-5-carbaldehyde (1.59 g, 8.80 mmol) and N-iodosuccinimide (97%, 2.14 g, 9.23 mmol) in dichloromethane (30 mL) was allowed to stir at room temperature for 30 minutes. The reaction was quenched by addition of aqueous sodium sulfite solution (1 M, 70 mL), concentrated in vacuo to remove dichloromethane, and diluted with acetone (40 mL). After stirring for 15 minutes, the mixture was filtered to provide the product as a solid. Yield: 2.5 g, 8.16 mmol, 93%. LCMS m/z 306.9, 308.9 [M+H]$^+$. $^1$H NMR (400 MHz, DMSO-$d_6$) δ 12.91 (br s, 1H), 10.42 (s, 1H), 8.66 (s, 1H), 7.97 (s, 1H).

Step 2. Synthesis of 4-chloro-3-iodo-1-[(4-methylphenyl)sulfonyl]-1H-pyrrolo[2,3-b]pyridine-5-carbaldehyde (C38)

Sodium hydride (60% in mineral oil, 384 mg, 9.60 mmol) was added in a single portion to a solution of C37 (2.45 g, 7.99 mmol) in N,N-dimethylformamide (25 mL). After 5 minutes, p-toluenesulfonyl chloride (98%, 1.71 g, 8.79 mmol) was introduced. The reaction mixture was stirred at room temperature for 30 minutes, whereupon water (175 mL) was added and stirring was continued for 10 minutes. The product, an off-white solid, was collected via filtration and washed with water. Yield: 3.20 g, 6.95 mmol, 87%. LCMS m/z 461.0, 463.0 [M+H]$^+$. $^1$H NMR (400 MHz, $CDCl_3$) δ 10.55 (s, 1H), 8.87 (s, 1H), 8.10 (br d, J=8.5 Hz, 2H), 8.03 (s, 1H), 7.33 (br d, J=8 Hz, 2H), 2.41 (s, 3H).

Step 3. Synthesis of 3-iodo-1-[(4-methylphenyl)sulfonyl]-4-(morpholin-4-yl)-1H-pyrrolo[2,3-b]pyridine-5-carbaldehyde (C39)

Morpholine (1.5 mL, 17 mmol) was added to a suspension of C38 (1.00 g, 2.17 mmol) in N,N-dimethylformamide (1 mL), and the resulting solution was heated at 75° C. for 1 hour. Additional morpholine (1 mL) was introduced, and heating was continued at 50° C. for 1.5 hours. The reaction mixture was allowed to cool to room temperature, and diluted with water. After the mixture had stirred for 10 minutes, the solid was collected via filtration, dissolved in dichloromethane, dried over magnesium sulfate, and chromatographed on silica gel (Gradient: 10% to 40% ethyl acetate in heptane). The product was obtained as a white solid. Yield: 250 mg, 0.489 mmol, 22%.

It was subsequently determined that the heat source may have malfunctioned in the course of this experiment. LCMS m/z 512.1 [M+H]$^+$. $^1$H NMR (400 MHz, $CDCl_3$) δ 10.48 (s, 1H), 8.80 (s, 1H), 8.12 (br d, J=8.4 Hz, 2H), 7.96 (s, 1H), 7.33 (br d, J=8 Hz, 2H), 4.00-4.05 (m, 4H), 3.34-3.39 (m, 4H), 2.41 (s, 3H).

Step 4. Synthesis of 3-{5-formyl-1-[(4-methylphenyl)sulfonyl]-4-(morpholin-4-yl)-1H-pyrrolo[2,3-b]pyridin-3-yl}benzonitrile (C40)

A mixture of C39 (216 mg, 0.422 mmol), [1,1'-bis(diphenylphosphino)ferrocene]dichloropalladium(II), dichloromethane complex (17.1 mg, 20.9 μmol) and potassium phosphate (271 mg, 1.28 mmol) was subjected to three cycles of vacuum/nitrogen fill. 2-Methyltetrahydrofuran (4 mL) and water (1.5 mL) were added, and the reaction mixture was again subjected to three cycles of vacuum/nitrogen fill. After the reaction mixture had been heated at 65° C. for 1.5 hours, it was cooled, diluted with water, and extracted twice with dichloromethane. The combined organic layers were dried over magnesium sulfate, filtered, and concentrated in vacuo. Chromatography on silica gel (Gradient: 10% to 40% ethyl acetate in heptane) afforded the product as a sticky white solid. Yield: 133 mg, 0.273 mmol, 65%. $^1$H NMR (400 MHz, $CDCl_3$) δ 10.36 (s, 1H), 8.75 (s, 1H), 8.16 (br d, J=8.5 Hz, 2H), 7.72-7.76 (m, 1H), 7.70-7.72 (m, 1H), 7.67 (s, 1H), 7.65-7.69 (m, 1H), 7.60 (dd, J=7.7, 7.5 Hz, 1H), 7.35 (br d, J=8.2 Hz, 2H), 3.26-3.30 (m, 4H), 3.04-3.09 (m, 4H), 2.43 (s, 3H).

Step 5. Synthesis of 3-[5-(hydroxymethyl)-1-[(4-methylphenyl)sulfonyl]-4-(morpholin-4-yl)-1H-pyrrolo[2,3-b]pyridin-3-yl]benzonitrile (C41)

To a suspension of C40 (14 mg, 29 μmol) in methanol (1 mL) was added sodium borohydride (90%, 1.2 mg, 29 μmol) in a single portion. The reaction mixture was stirred at room temperature for 20 minutes, whereupon it was quenched with saturated aqueous ammonium chloride solution, diluted with water, and filtered, affording the product as a white solid (17 mg). By $^1$H NMR analysis, this material consisted of a roughly 2:1 mixture of product and starting material; this was taken directly into the following step. LCMS m/z 489.2 [M+H]$^+$. $^1$H NMR (400 MHz, $CDCl_3$), characteristic product peaks: δ 8.38 (s, 1H), 8.15 (br d, J=8.5 Hz, 2H), 7.61 (s, 1H), 4.83 (s, 2H), 2.41 (s, 3H).

Step 6. Synthesis of 3-[5-(hydroxymethyl)-4-(morpholin-4-yl)-1H-pyrrolo[2,3-b]pyridin-3-yl]benzonitrile (10)

Compound C41 (from the preceding step, 17 mg, <29 μmol) was combined with tetrabutylammonium fluoride (1 M solution in tetrahydrofuran, 0.2 mL, 0.2 mmol), and the reaction mixture was stirred for 18 hours at 60° C. Saturated aqueous sodium bicarbonate solution was added, and the resulting mixture was extracted twice with dichloromethane. The combined organic layers were dried over magnesium sulfate, filtered, and concentrated in vacuo. Purification via reversed phase HPLC (Column: Waters XBridge C18, 5 μm; Mobile phase A: 0.03% ammonium hydroxide in water (v/v); Mobile phase B: 0.03% ammonium hydroxide in acetonitrile (v/v); Gradient: 5% to 100% B) provided the product. Yield: 1.75 mg, 5.23 μmol, 18% over 2 steps. LCMS m/z 335.3 [M+H]$^+$. $^1$H NMR (600 MHz, DMSO-$d_6$) δ 8.03 (s, 1H), 7.87 (dd, J=1.6, 1.3 Hz, 1H), 7.80 (ddd, J=7.8, 1.6, 1.2 Hz, 1H), 7.68 (br ddd, J=7.8, 1, 1 Hz, 1H), 7.57 (dd, J=7.8, 7.8 Hz, 1H), 7.44 (s, 1H), 4.65 (s, 2H), 3.13-3.20 (m, 4H), 3.04-3.10 (m, 4H).

Example 11
3-(3-Cyanophenyl)-4-(morpholin-4-yl)-1H-pyrrolo[2,3-b]pyridine-5-carbonitrile (11)
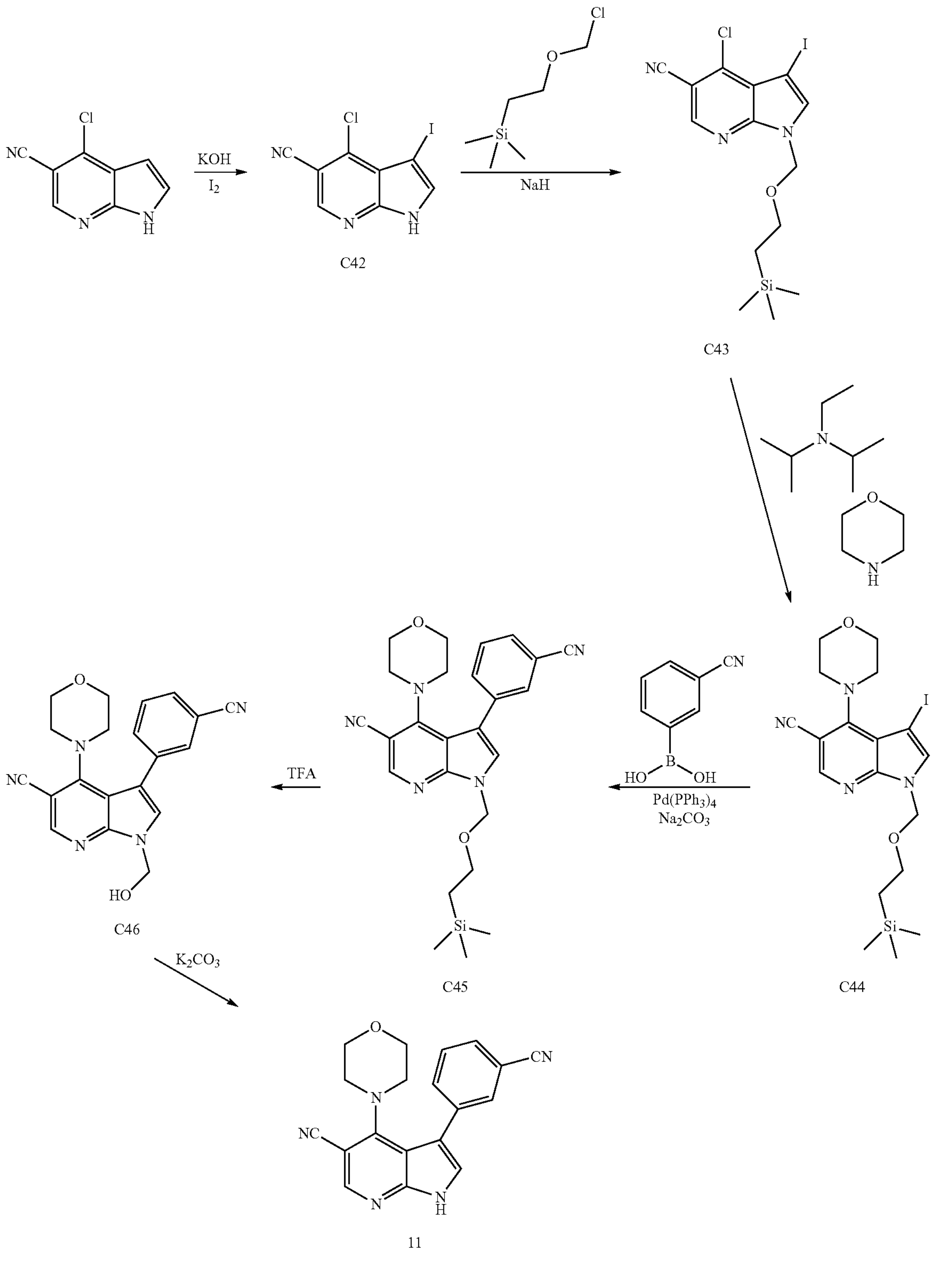
C42 C43 C44 C45 C46 11

Step 1. Synthesis of 4-chloro-3-iodo-1H-pyrrolo[2,3-b]pyridine-5-carbonitrile (C42)

Potassium hydroxide (0.63 g, 11 mmol) and iodine (2.15 g, 8.47 mmol) were added to a 0° C. suspension of 4-chloro-1H-pyrrolo[2,3-b]pyridine-5-carbonitrile (1.0 g, 5.63 mmol) in N,N-dimethylformamide (20 mL). The reaction mixture was stirred at room temperature for 4 hours, whereupon it was diluted with water and extracted with ethyl acetate (3×50 mL). The combined organic layers were washed with saturated aqueous sodium chloride solution (50 mL), dried over sodium sulfate, filtered, and concentrated under reduced pressure. Purification via silica gel chromatography afforded the product as an off-white solid. Yield: 1.1 g, 3.6 mmol, 64%. $^1$H NMR (400 MHz, DMSO-$d_6$) δ 13.06 (br s, 1H), 8.67 (s, 1H), 8.05 (d, J=2.5 Hz, 1H).

Step 2. Synthesis of 4-chloro-3-iodo-1-{[2-(trimethylsilyl)ethoxy]methyl}-1H-pyrrolo[2,3-b]pyridine-5-carbonitrile (C43)

Sodium hydride (60% in mineral oil, 290 mg, 7.2 mmol) was added to a 0° C. suspension of C42 (1.1 g, 3.6 mmol) in tetrahydrofuran (20 mL). After 30 minutes, 2-(trimethylsilyl)ethoxymethyl chloride (0.90 g, 5.4 mmol) was added to the 0° C. reaction mixture, whereupon it was allowed to warm to room temperature and stir for 18 hours. After being diluted with water, the mixture was extracted with ethyl acetate (3×50 mL), and the combined organic layers were washed with saturated aqueous sodium chloride solution (50 mL), dried over sodium sulfate, filtered, and concentrated in vacuo. Silica gel chromatography provided the product as a red solid. By $^1$H NMR analysis, this material was contaminated with extraneous [2-(trimethylsilyl)ethoxy]methyl-containing impurities. It was taken directly into the following step. Yield: 1.0 g, <2.3 mmol, <64%. $^1$H NMR (400 MHz, $CDCl_3$), product peaks only: δ 8.52 (s, 1H), 7.65 (s, 1H), 5.65 (s, 2H), 3.49-3.56 (m, 2H), 0.89-0.95 (m, 2H), −0.04 (s, 9H).

Step 3. Synthesis of 3-iodo-4-(morpholin-4-yl)-1-{[2-(trimethylsilyl)ethoxy]methyl}-1H-pyrrolo[2,3-b]pyridine-5-carbonitrile (C44)

Morpholine (0.40 g, 4.6 mmol) was added to a solution of C43 (from the previous step, 1.0 g, <2.3 mmol) in n-butanol (6 mL) and N,N-diisopropylethylamine (3 mL). The reaction mixture was stirred at 100° C. for 18 hours, whereupon it was concentrated in vacuo. Chromatography on silica gel provided the product as a yellow oil. Yield: 700 mg, 1.4 mmol, 39% over two steps. $^1$H NMR (400 MHz, $CDCl_3$) δ 8.39 (s, 1H), 7.53 (s, 1H), 5.61 (s, 2H), 4.02-4.08 (m, 4H), 3.58-3.64 (m, 4H), 3.50-3.57 (m, 2H), 0.88-0.96 (m, 2H), −0.04 (s, 9H).

Step 4. Synthesis of 3-(3-cyanophenyl)-4-(morpholin-4-yl)-1-{[2-(trimethylsilyl)ethoxy]methyl}-1H-pyrrolo[2,3-b]pyridine-5-carbonitrile (C45)

Compound C44 was reacted with (3-cyanophenyl)boronic acid according to the procedure described for synthesis of C6 in Example 2. In this case, purification was carried out by preparative thin layer chromatography, affording the product as a brown oil. Yield: 150 mg, 0.326 mmol, 79%. LCMS m/z 460.2 $[M+H]^+$.

Step 5. Synthesis of 3-(3-cyanophenyl)-1-(hydroxymethyl)-4-(morpholin-4-yl)-1H-pyrrolo[2,3-b]pyridine-5-carbonitrile (C46)

Compound C45 (150 mg, 0.326 mmol) was dissolved in trifluoroacetic acid (3 mL). The reaction mixture was stirred at room temperature for 2 hours, and then concentrated in vacuo, providing the product as a brown oil (110 mg); this was used directly in the next step, without additional purification.

Step 6. Synthesis of 3-(3-cyanophenyl)-4-(morpholin-4-yl)-1H-pyrrolo[2,3-b]pyridine-5-carbonitrile (11)

Compound C46 (from the previous step, 110 mg, <1.326 mmol) was dissolved in acetonitrile (3 mL); solid potassium carbonate was added to adjust the pH to >12, and the reaction mixture was stirred at room temperature for 30 minutes. Solids were removed via filtration, and the filtrate was concentrated under reduced pressure. Purification by reversed phase HPLC (Column: Phenomenex Gemini C18, 8 μm; Mobile phase A: aqueous ammonia, pH 10; Mobile phase B: acetonitrile; Gradient: 28% to 48% B) afforded the product as a white solid. Yield: 67 mg, 0.20 mmol, 61% over 2 steps. LCMS m/z 330.2 $[M+H]^+$. $^1$H NMR (400 MHz, $CDCl_3$) δ 10.30 (br s, 1H), 8.45 (s, 1H), 7.76 (dd, J=1.5, 1.4 Hz, 1H), 7.67-7.72 (m, 2H), 7.58 (dd, J=7.8, 7.8 Hz, 1H), 7.31 (s, 1H), 3.37 (s, 8H).

Example 12

4-(3,6-Dihydro-2H-pyran-4-yl)-3-(1-methyl-1H-pyrazol-4-yl)-1H-pyrrolo[2,3-b]pyridine (12)

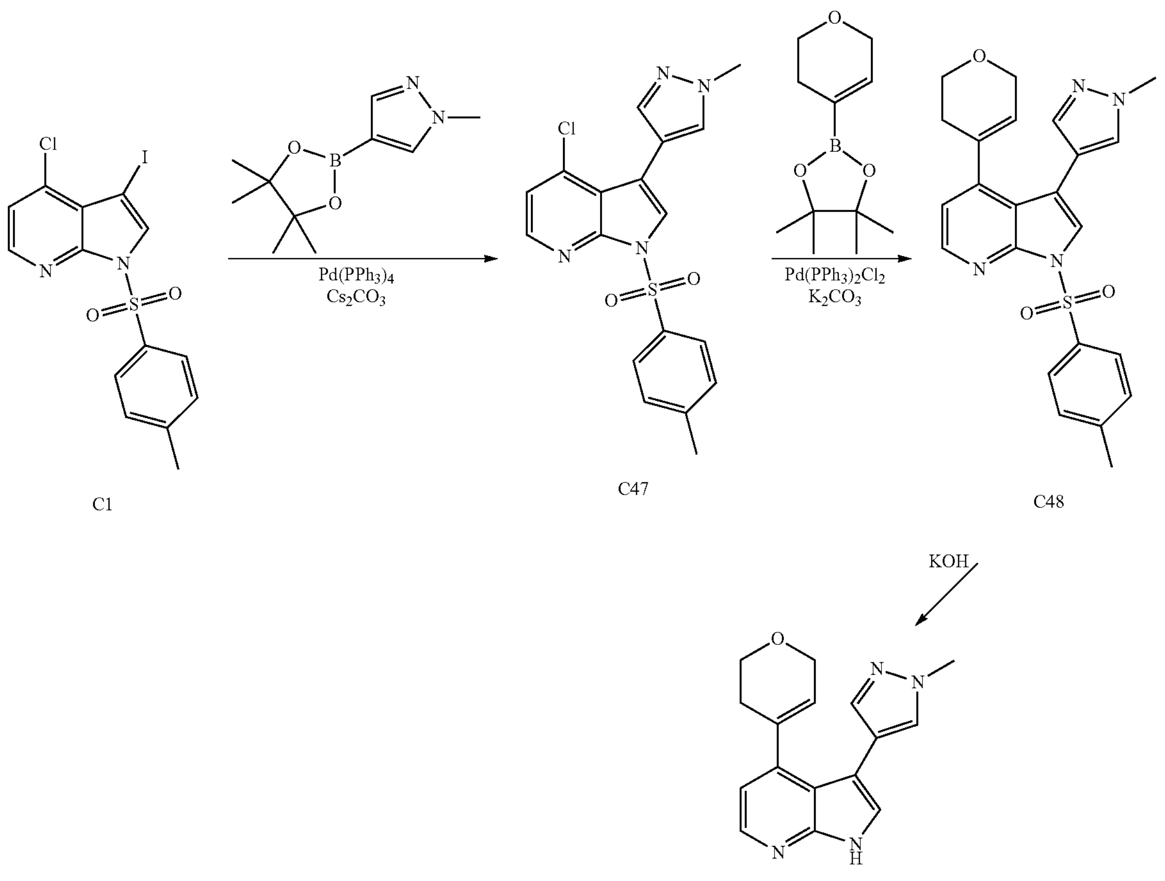

C1 C47 C48 12

Step 1. Synthesis of 4-chloro-1-[(4-methylphenyl)sulfonyl]-3-(1-methyl-1H-pyrazol-4-yl)-1H-pyrrolo[2,3-b]pyridine (C47)

This experiment was carried out in 12 batches. Compound C1 was reacted with 1-methyl-4-(4,4,5,5-tetramethyl-1,3,2-dioxaborolan-2-yl)-1H-pyrazole using the method described for synthesis of C2 in Example 1. The product was obtained as a white solid. Yield: 6.1 g, 16 mmol, 58%. $^1$H NMR (400 MHz, $CDCl_3$) δ 8.31 (d, J=5.3 Hz, 1H), 8.10 (br d, J=8.3 Hz, 2H), 7.71 (s, 1H), 7.64 (s, 1H), 7.55 (s, 1H), 7.30 (br d, J=8.2 Hz, 2H), 7.19 (d, J=5.2 Hz, 1H), 3.98 (s, 3H), 2.39 (s, 3H).

Step 2. Synthesis of 4-(3,6-dihydro-2H-pyran-4-yl)-1-[(4-methylphenyl)sulfonyl]-3-(1-methyl-1H-pyrazol-4-yl)-1H-pyrrolo[2,3-b]pyridine (C48)

Dichlorobis(triphenylphosphine)palladium(II) (36.7 mg, 52.3 μmol) and potassium carbonate (143 mg, 1.03 mmol) were added to a solution of C47 (200 mg, 0.517 mmol) and 4-(4,4,5,5-tetramethyl-1,3,2-dioxaborolan-2-yl)-3,6-dihydro-2H-pyran (109 mg, 0.519 mmol) in tetrahydrofuran (10 mL). The reaction mixture was degassed and purged with nitrogen three times, then heated at 80° C. for 18 hours. After cooling to room temperature, it was extracted with ethyl acetate (3×20 mL), washed with saturated aqueous sodium chloride solution (30 mL), dried over sodium sulfate, filtered, and concentrated in vacuo. Preparative thin layer chromatography (Eluent: 1:1 petroleum ether/ethyl acetate) afforded the product as a yellow oil. Yield: 50 mg, 0.12 mmol, 23%. LCMS m/z 435.0 $[M+H]^+$.

Step 3. Synthesis of 4-(3,6-dihydro-2H-pyran-4-yl)-3-(1-methyl-1H-pyrazol-4-yl)-1H-pyrrolo[2,3-b]pyridine (12)

To a solution of C48 (100 mg, 0.23 mmol) in methanol (15 mL) was added potassium hydroxide (26 mg, 0.46 mmol). The reaction mixture was heated at 50° C. for 2 hours, then concentrated in vacuo. Purification via reversed phase HPLC (Column: Phenomenex Gemini C18, 8 μm; Mobile phase A: aqueous ammonia, pH 10; Mobile phase B: acetonitrile; Gradient: 16% to 36% B) provided the product as a white solid. Yield: 35 mg, 0.12 mmol, 52%. LCMS m/z 281.1 $[M+H]^+$. $^1$H NMR (400 MHz, $CD_3OD$) δ 8.17 (d, J=5.0 Hz, 1H), 7.60 (s, 1H), 7.48 (s, 1H), 7.38 (s, 1H), 6.94 (d, J=5.0 Hz, 1H), 5.65-5.68 (m, 1H), 4.10-4.14 (m, 2H), 3.94 (s, 3H), 3.65 (t, J=5.4 Hz, 2H), 2.20-2.26 (m, 2H).

Method A

Synthesis of 3-substituted 4-(morpholin-4-yl)-1H-pyrrolo[2,3-b]pyridines via Suzuki reaction

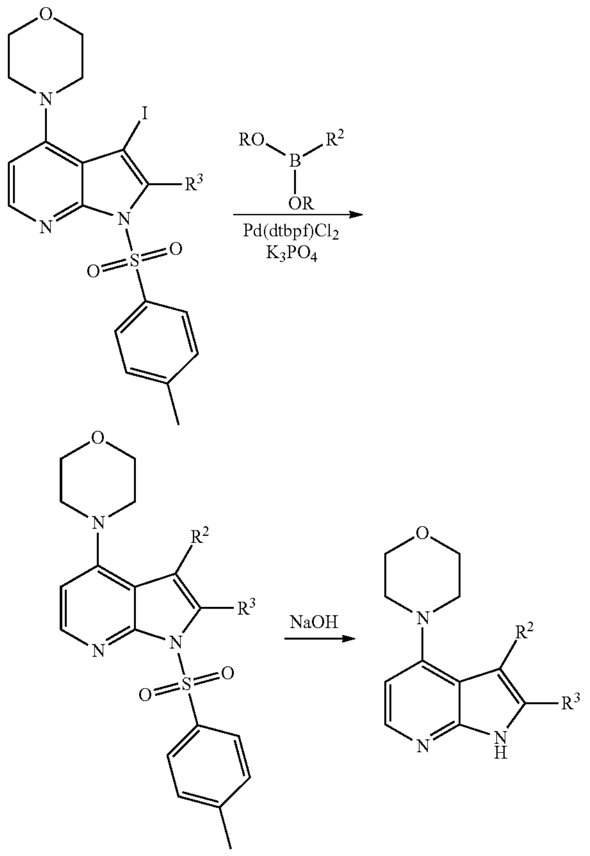

C49

Step 1. Synthesis of 3-substituted 1-[(4-methylphenyl)sulfonyl]-4-(morpholin-4-yl)-1H-pyrrolo[2,3-b]pyridines (C49)

A solution of the appropriate 3-iodo-1-[(4-methylphenyl)sulfonyl]-4-(morpholin-4-yl)-1H-pyrrolo[2,3-b]pyridine in 1,4-dioxane (0.167 M, 600 μL, 100 μmol) was added to the requisite boronic acid or boronate (120 μmol) in a reaction vial. Aqueous potassium phosphate solution (0.5 M, 400 μL, 200 μmol) was added, followed by [1,1'-bis(di-tert-butylphosphino)ferrocene]dichloropalladium(II) (4 mg, 6 μmol), and the reaction mixture was shaken at 110° C. for 16 hours, whereupon it was taken directly to the following step.

Step 2. Synthesis of 3-substituted 4-(morpholin-4-yl)-1H-pyrrolo[2,3-b]pyridines The crude reaction mixture containing C49 (from the preceding step, 5100 μmol) was treated with aqueous sodium hydroxide solution (1.0 M, 1.0 mL, 1.0 mmol), and shaken at 110° C. for 16 hours. After removal of solvents using a SpeedVac concentrator, the residue was dissolved in methanol and filtered. Purification was carried out by reversed phase HPLC using an appropriate gradient in one of the following systems: 1) Column: Phenomenex Synergi C18, 4 μm or DIKMA Diamonsil(2) C18, 5 μm; Mobile phase A: water containing 0.225% formic acid; Mobile phase B: acetonitrile; or 2) Column: Phenomenex Gemini C18 (10 μm, 8 μm, or 5 μm) or YMC-Actus Triart C18, 5 μm; Mobile phase A: aqueous ammonium hydroxide, pH 10; Mobile phase B: acetonitrile.

Method B

Synthesis of 4-amino-substituted 1H-pyrrolo[2,3-b]pyridines via nucleophilic aromatic substitution reaction

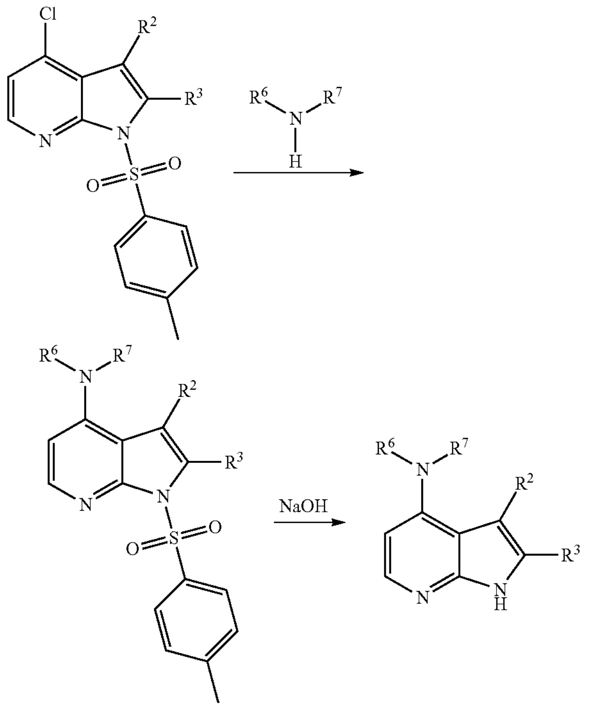

C50

Step 1. Synthesis of 4-amino-substituted 1-[(4-methylphenyl)sulfonyl]-1H-pyrrolo[2,3-b]pyridines (C50)

A solution of the appropriate 4-chloro-1-[(4-methylphenyl)sulfonyl]-1H-pyrrolo[2,3-b]pyridine in 1-methylpyrrolidin-2-one (0.333 M, 300 μL, 100 μmol) was added to the requisite amine (700 μmol, or 1 mmol if volatile). N,N-Diisopropylethylamine (1 equivalent) was added if a salt of the amine was employed. The reaction vessel was sealed and irradiated at 180° C. for 2 hours in a Biotage microwave reactor. Solvent was removed using a SpeedVac concentrator, and the crude residue was utilized directly in the following step.

Step 2. Synthesis of 4-amino-substituted 1H-pyrrolo[2,3-b]pyridines

The crude residue containing C50 (from the preceding step, 100 μmol) was mixed with 1,4-dioxane (1 mL) and treated with aqueous sodium hydroxide solution (1.0 M, 500 μL, 500 μmol). The reaction vial was capped and shaken at 100° C. for 16 hours, and solvents were removed using a SpeedVac concentrator. Purification was effected via reversed phase HPLC with an appropriate gradient, using one of the following systems: 1) Column: DIKMA Diamonsil(2) C18, 5 μm; Mobile phase A: water containing 0.225% formic acid; Mobile phase B: acetonitrile; or 2) Column: Phenomenex Gemini C18, 8 μm; Mobile phase A: aqueous ammonium hydroxide, pH 10; Mobile phase B: acetonitrile.

Method C

Synthesis of 4-substituted 1H-pyrrolo[2,3-b]pyridines via Suzuki reaction

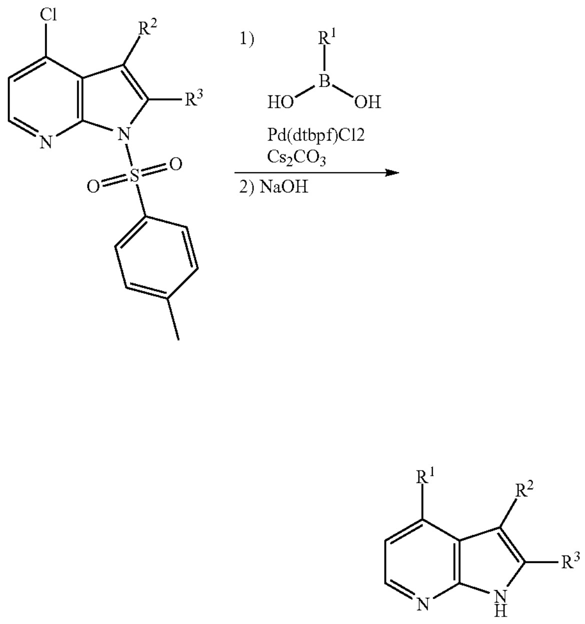

A solution of the appropriate 4-chloro-1-[(4-methylphenyl)sulfonyl]-1H-pyrrolo[2,3-b]pyridine in 1,4-dioxane (0.2 M, 500 μL, 100 μmol) was treated with the desired boronic acid (0.3 M solution in 1,4-dioxane, 500 μL, 150 μmol). Aqueous cesium carbonate solution (1.0 M, 200 μL, 200 μmol) was added, followed by [1,1'-bis(di-tert-butylphosphino)ferrocene]dichloropalladium(II) (1.3 mg, 2.0 μmol), and the vial was capped and shaken at 100° C. for 16 hours. The reaction mixture was then treated with aqueous sodium hydroxide solution (2.0 M, 500 μL, 1.0 mmol) and shaken at 60° C. for 4 hours. Solvents were removed using a SpeedVac concentrator, and the residue was purified by reversed phase HPLC using an appropriate gradient with one of the following systems: 1) Column: DIKMA Diamonsil(2) C18, 5 μm or Agella Venusil ASB C18, 5 μm or YMC-Actus Triart C18, 5 μm; Mobile phase A: water containing 0.225% formic acid; Mobile phase B: acetonitrile; or 2) Column: Phenomenex Gemini C18, 8 μm; Mobile phase A: aqueous ammonium hydroxide, pH 10; Mobile phase B: acetonitrile.

Method D

Synthesis of 4-amino-substituted 1H-pyrrolo[2,3-b]pyridines via Buchwald-Hartwig amination

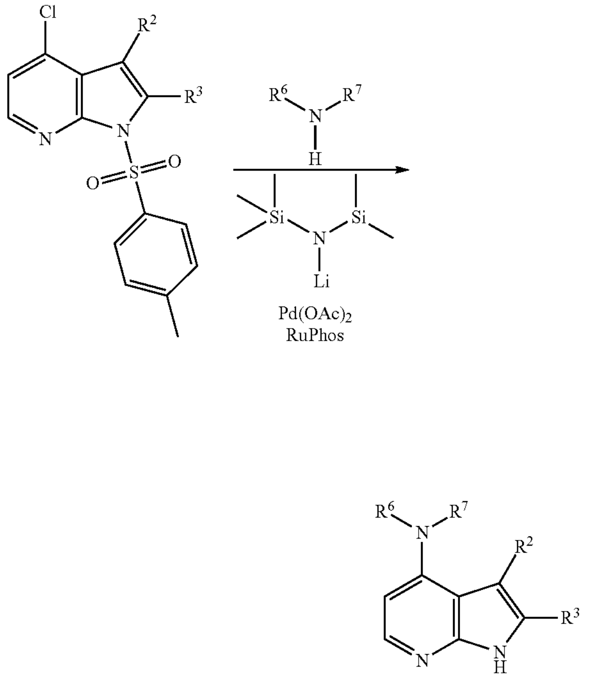

The appropriate 4-chloro-1-[(4-methylphenyl)sulfonyl]-1H-pyrrolo[2,3-b]pyridine (100 μmol) was combined with the desired amine (180 μmol), palladium(II) acetate (1.1 mg, 5 μmol) and [2',6'-bis(propan-2-yloxy)biphenyl-2-yl](dicyclohexyl)phosphane (RuPhos, 4.7 mg, 10 μmol). Tetrahydrofuran, which had been purged with a nitrogen stream for 2 hours, (300 μL) was added, the reaction mixture was purged with nitrogen, and lithium bis(trimethylsilyl)amide (1.0 M solution in tetrahydrofuran, 600 μL, 600 μmol) was introduced. After being purged with nitrogen for 3 minutes, the reaction mixture was shaken at 60° C. for 6 hours. Solvent was removed using a SpeedVac concentrator, and the residue was purified by reversed phase HPLC using an appropriate gradient with one of the following systems: 1) Column: Phenomenex Gemini C18, 8 μm; Mobile phase A: water containing 0.225% formic acid; Mobile phase B: acetonitrile; or 2) Phenomenex Gemini C18, 8 μm; Mobile phase A: aqueous ammonium hydroxide, pH 10; Mobile phase B: acetonitrile; or 3) Column: Waters Sunfire C18, 5 μm; Mobile phase A: water containing 0.05% formic acid; Mobile phase B: acetonitrile containing 0.05% formic acid.

TABLE 1

| Method of preparation and physicochemical properties for Examples 13-112 | | | |
|---|---|---|---|
| Example Number | Method of Preparation; Non-commercial starting materials | Structure | $^1H$ NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
| 13 | Example 9[1]; C5[2] | 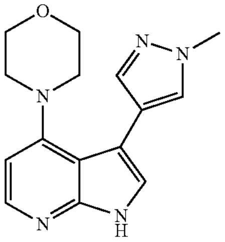 [SMILES: Cn1cc(-c2c[nH]c3nccc(N4CCOCC4)c23)cn1] | $^1H$ NMR (400 MHz, DMSO-$d_6$) δ 11.63 (br s, 1H), 8.07 (d, J = 5.1 Hz, 1H), 7.83 (s, 1H), 7.61 (s, 1H), 7.33 (br s, 1H), 6.62 (d, J = 5.3 Hz, 1H), 3.89 (s, 3H), 3.51-3.59 (m, 4H), 2.85-2.93 (m, 4H); 284.1 |
| 14 | Example 11[3] | 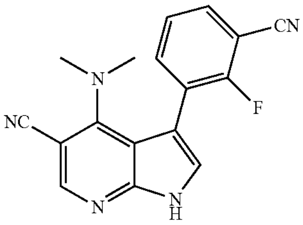 [SMILES: CN(C)c1c(C#N)cnc2[nH]cc(-c3cccc(C#N)c3F)c12] | $^1H$ NMR (500 MHz, DMSO-$d_6$) δ 12.51 (br s, 1H), 8.31 (s, 1H), 7.90 (ddd, J = 7.5, 6, 1.7 Hz, 1H), 7.77 (ddd, J = 7.7, 7.6, 1.6 Hz, 1H), 7.68 (d, J = 3 Hz, 1H), 7.46 (dd, J = 7.8, 7.8 Hz, 1H), 2.75 (s, 6H); 306.3 |
| 15 | Example 1; C1 | 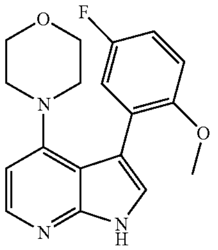 [SMILES: COc1ccc(F)cc1-c1c[nH]c2nccc(N3CCOCC3)c12] | $^1H$ NMR (400 MHz, $CD_3OD$) δ 8.07 (d, J = 5.8 Hz, 1H), 7.36 (s, 1H), 7.09-7.14 (m, 1H), 7.03-7.07 (m, 2H), 6.74 (d, J = 5.8 Hz, 1H), 3.77 (s, 3H), 3.35-3.40 (m, 4H), 2.97-3.03 (m, 4H); 328.1 |
| 16 | Example 1; C1 | 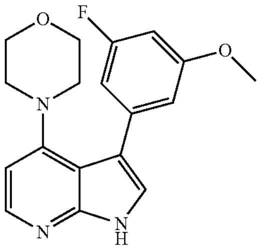 [SMILES: COc1cc(F)cc(-c2c[nH]c3nccc(N4CCOCC4)c23)c1] | $^1H$ NMR (400 MHz, $CD_3OD$) δ 8.10 (d, J = 5.5 Hz, 1H), 7.38 (s, 1H), 6.96-6.98 (m, 1H), 6.92 (ddd, J = 9.7, 2.3, 1.3 Hz, 1H), 6.74 (d, J = 5.6 Hz, 1H), 6.65 (ddd, J = 10.9, 2.4, 2.3 Hz, 1H), 3.87 (s, 3H), 3.51-3.55 (m, 4H), 2.97-3.01 (m, 4H); 328.1 |
| 17 | Example 9; C31[2] | 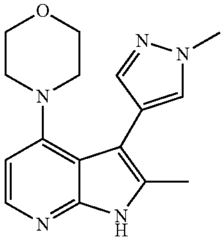 [SMILES: Cc1[nH]c2nccc(N3CCOCC3)c2c1-c1cnn(C)c1] | $^1H$ NMR (400 MHz, DMSO-$d_6$ + $D_2O$) δ 7.94 (d, J = 5.3 Hz, 1H), 7.70 (s, 1H), 7.47 (s, 1H), 6.56 (d, J = 5.5 Hz, 1H), 3.87 (s, 3H, assumed; partially obscured by water peak), 3.36-3.41 (m, 4H), 2.77-2.82 (m, 4H), 2.29 (s, 3H); 298.1 |

TABLE 1-continued

Method of preparation and physicochemical properties for Examples 13-112

| Example Number | Method of Preparation; Non-commercial starting materials | Structure | $^1$H NMR (400 MHz, $CDCl_3$) δ (ppm); Mass spectrum, observed ion m/z ($M + H^+$) or HPLC retention time; Mass spectrum m/z $[M + H]^+$ (unless otherwise indicated) |
|---|---|---|---|
| 18 | Example 9; C35 | 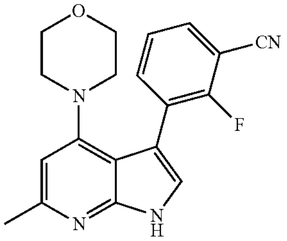 [SMILES: Cc1cc(N2CCOCC2)c2c(-c3cccc(C#N)c3F)c[nH]c2n1] | 7.76 (ddd, J = 7.6, 7.3, 1.8 Hz, 1H), 7.63 (ddd, J = 7.7, 5.8, 1.7 Hz, 1H), 7.36 (dd, J = 7.8, 7.6 Hz, 1H), 7.32-7.34 (m, 1H), 6.54 (s, 1H), 3.40-3.45 (m, 4H), 3.00-3.05 (m, 4H), 2.69 (s, 3H); 337.1 |
| 19 | Example 3; C7 | 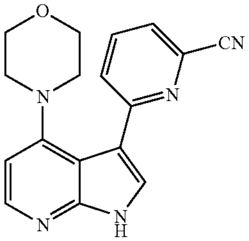 [SMILES: N#Cc1cccc(-c2c[nH]c3nccc(N4CCOCC4)c23)n1] | $^1$H NMR (400 MHz, DMSO-$d_6$) δ 8.07-8.18 (m, 3H), 7.86 (br d, J = 7 Hz, 1H), 7.84 (s, 1H), 6.75 (d, J = 5.5 Hz, 1H), 3.49-3.54 (m, 4H), 2.86-2.91 (m, 4H); 306.1 |
| 20 | Method A; C5 | 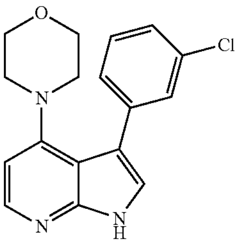 [SMILES: Clc1cccc(-c2c[nH]c3nccc(N4CCOCC4)c23)c1] | 2.44 minutes[4]; 314.1, 316.1 |
| 21 | Method A; C5 | 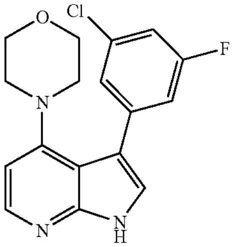 [SMILES: Fc1cc(Cl)cc(-c2c[nH]c3nccc(N4CCOCC4)c23)c1] | 2.51 minutes[4]; 332.1, 334.1 |
| 22 | Method A; C5 | 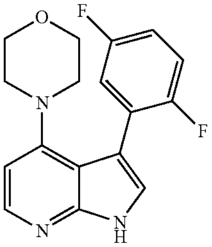 [SMILES: Fc1ccc(F)c(-c2c[nH]c3nccc(N4CCOCC4)c23)c1] | 2.26 minutes[4]; 316.1 |

TABLE 1-continued

Method of preparation and physicochemical properties for Examples 13-112

| Example Number | Method of Preparation; Non-commercial starting materials | Structure | $^1$H NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
|---|---|---|---|
| 23 | Method A; C5 | 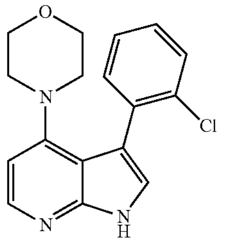 [SMILES: Clc1ccccc1-c1c[nH]c2nccc(N3CCOCC3)c12] | 2.33 minutes[4]; 314.1, 316.1 |
| 24 | Method A; C5 | 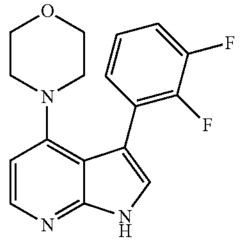 [SMILES: Fc1cccc(-c2c[nH]c3nccc(N4CCOCC4)c23)c1F] | 2.29 minutes[4]; 316.1 |
| 25 | Method A; C5 | 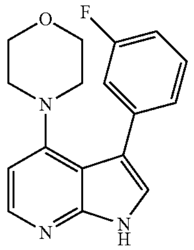 [SMILES: Fc1cccc(-c2c[nH]c3nccc(N4CCOCC4)c23)c1] | 2.29 minutes[4]; 298.1 |
| 26 | Method A; C5 | 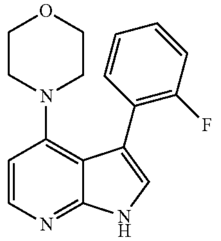 [SMILES: Fc1ccccc1-c1c[nH]c2nccc(N3CCOCC3)c12] | 2.22 minutes[4]; 298.1 |
| 27 | Method A; C5 | 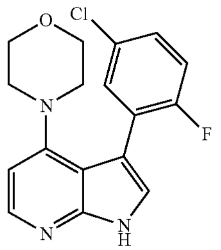 [SMILES: Fc1ccc(Cl)cc1-c1c[nH]c2nccc(N3CCOCC3)c12] | 2.41 minutes[4]; 332.1 |

TABLE 1-continued

| Method of preparation and physicochemical properties for Examples 13-112 | | | |
|---|---|---|---|
| Example Number | Method of Preparation; Non-commercial starting materials | Structure | $^1$H NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
| 28 | Method A; C5 | 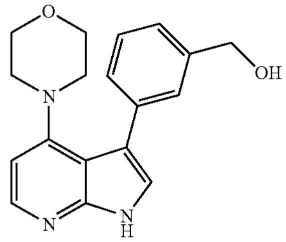 [SMILES: OCc1cccc(-c2c[nH]c3nccc(N4CCOCC4)c23)c1] | 2.21 minutes[5]; 310.2 |
| 29 | Method A; C5 | 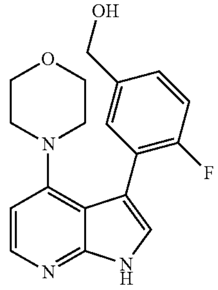 [SMILES: OCc1ccc(F)c(-c2c[nH]c3nccc(N4CCOCC4)c23)c1] | 2.22 minutes[5]; 328.1 |
| 30 | Method A; C5 | 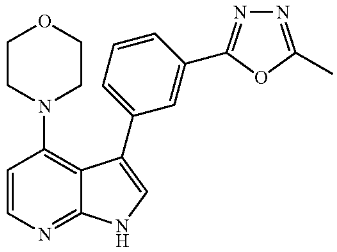 [SMILES: Cc1nnc(-c2cccc(-c3c[nH]c4nccc(N5CCOCC5)c34)c2)o1] | 2.33 minutes[5]; 362.2 |
| 31 | Method A; C5 | 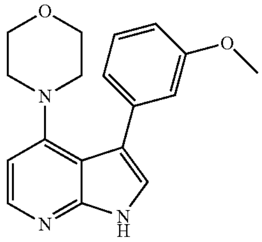 [SMILES: COc1cccc(-c2c[nH]c3nccc(N4CCOCC4)c23)c1] | 2.52 minutes[5]; 310.2 |
| 32 | Method A; C5 | 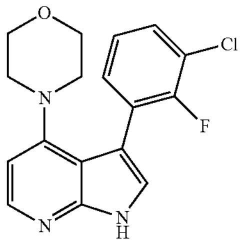 [SMILES: Fc1c(Cl)cccc1-c1c[nH]c2nccc(N3CCOCC3)c12] | 2.42 minutes[4]; 332.1, 334.1 |

TABLE 1-continued

| Method of preparation and physicochemical properties for Examples 13-112 | | | |
|---|---|---|---|
| Example Number | Method of Preparation; Non-commercial starting materials | Structure | $^1$H NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
| 33 | Method A; C5 | 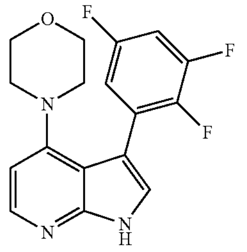 [SMILES: Fc1cc(F)c(F)c(-c2c[nH]c3nccc(N4CCOCC4)c23)c1] | 2.35 minutes[4]; 334.1 |
| 34 | Method A; C5 | 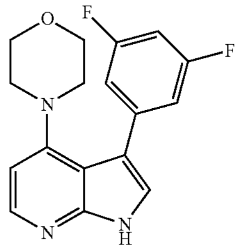 [SMILES: Fc1cc(F)cc(-c2c[nH]c3nccc(N4CCOCC4)c23)c1] | 2.37 minutes[4]; 316.1 |
| 35 | Method A; C5 | 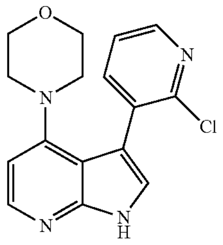 [SMILES: Clc1ncccc1-c1c[nH]c2nccc(N3CCOCC3)c12] | 2.15 minutes[5]; 315.1, 317.1 |
| 36 | Method A; C5 | 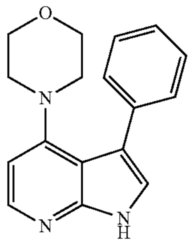 [SMILES: c1ccc(-c2c[nH]c3nccc(N4CCOCC4)c23)cc1] | 2.50 minutes[5]; 280.1 |
| 37 | Method A; C5 | 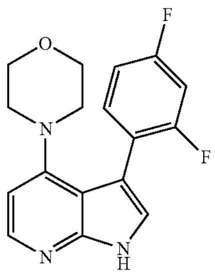 [SMILES: Fc1ccc(-c2c[nH]c3nccc(N4CCOCC4)c23)c(F)c1] | 2.28 minutes[4]; 316.1 |

TABLE 1-continued

| Example Number | Method of Preparation; Non-commercial starting materials | Structure | $^1$H NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
|---|---|---|---|
| | Method of preparation and physicochemical properties for Examples 13-112 | | |
| 38 | Method A; C5 | 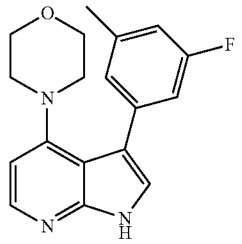 [SMILES: Cc1cc(F)cc(-c2c[nH]c3nccc(N4CCOCC4)c23)c1] | 2.45 minutes[4]; 312.1 |
| 39 | Method A; C5 | 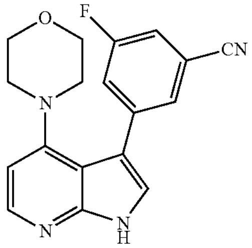 [SMILES: N#Cc1cc(F)cc(-c2c[nH]c3nccc(N4CCOCC4)c23)c1] | 2.38 minutes[5]; 323.1 |
| 40 | Method A; C5 | 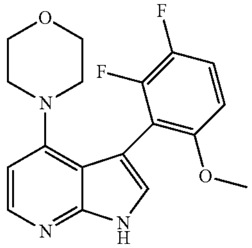 [SMILES: COc1ccc(F)c(F)c1-c1c[nH]c2nccc(N3CCOCC3)c12] | 2.62 minutes[5]; 346.1 |
| 41 | Method A; C5 | 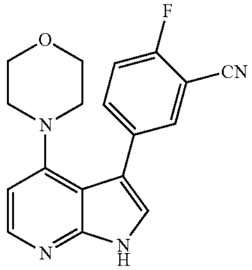 [SMILES: N#Cc1cc(-c2c[nH]c3nccc(N4CCOCC4)c23)ccc1F] | 2.48 minutes[5]; 323.1 |
| 42 | Method A; C5 | 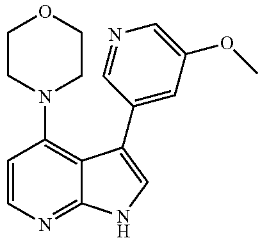 [SMILES: COc1cncc(-c2c[nH]c3nccc(N4CCOCC4)c23)c1] | 1.90 minutes[5]; 311.1 |

TABLE 1-continued

Method of preparation and physicochemical properties for Examples 13-112

| Example Number | Method of Preparation; Non-commercial starting materials | Structure | $^1$H NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
|---|---|---|---|
| 43 | Example 3; C31 | 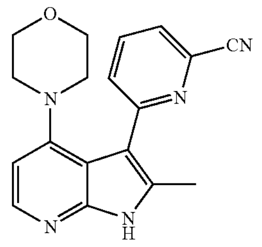 [SMILES: Cc1[nH]c2nccc(N3CCOCC3)c2c1-c1cccc(C#N)n1] | 10.09 (br s, 1H), 8.19 (d, J = 5.5 Hz, 1H), 7.89 (dd, J = 8.0, 7.8 Hz, 1H), 7.79 (dd, J = 7.9, 1.0 Hz, 1H), 7.61 (dd, J = 7.5, 0.9 Hz, 1H), 6.69 (d, J = 5.5 Hz, 1H), 3.41-3.47 (m, 4H), 2.91-2.96 (m, 4H), 2.64 (s, 3H); 320.1 |
| 44 | Example 11[6]; C44 | 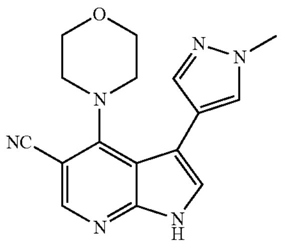 [SMILES: Cn1cc(-c2c[nH]c3ncc(C#N)c(N4CCOCC4)c23)cn1] | 10.19 (br s, 1H), 8.38 (s, 1H), 7.56 (d, J = 0.6 Hz, 1H), 7.46 (br s, 1H), 7.20 (br s, 1H), 4.01 (s, 3H), 3.47-3.52 (m, 4H), 3.41-3.47 (m, 4H); 309.1 |
| 45 | Example 11; C44 | 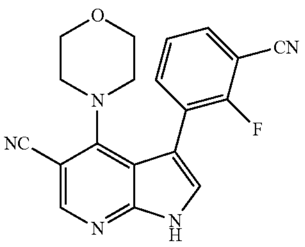 [SMILES: N#Cc1cccc(-c2c[nH]c3ncc(C#N)c(N4CCOCC4)c23)c1F] | $^1$H NMR (400 MHz, $CD_3OD$) δ 8.38 (s, 1H), 7.78-7.85 (m, 2H), 7.53 (s, 1H), 7.47 (dd, J = 7.9, 7.6 Hz, 1H), 3.23-3.3 (m, 8H, assumed; partially obscured by solvent peak); 348.2 |
| 46 | Example 11; C44 | 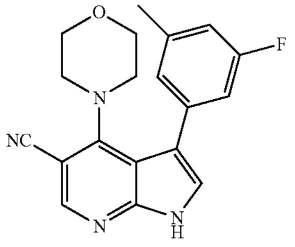 [SMILES: Cc1cc(F)cc(-c2c[nH]c3ncc(C#N)c(N4CCOCC4)c23)c1] | $^1$H NMR (400 MHz, $CD_3OD$) δ 8.31 (s, 1H), 7.37 (s, 1H), 7.09-7.12 (m, 1H), 7.00 (br d, J = 10 Hz, 1H), 6.95 (br d, J = 10 Hz, 1H), 3.36 (s, 8H), 2.43 (s, 3H); 337.2 |
| 47 | Method A; C5 | 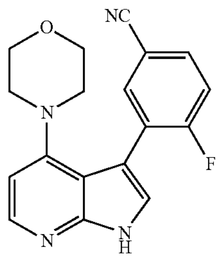 [SMILES: N#Cc1ccc(F)c(-c2c[nH]c3nccc(N4CCOCC4)c23)c1] | 2.35 minutes[5]; 323 |

TABLE 1-continued

| Example Number | Method of Preparation; Non-commercial starting materials | Structure | $^1$H NMR (400 MHz, $CDCl_3$) δ (ppm); Mass spectrum, observed ion m/z ($M + H^+$) or HPLC retention time; Mass spectrum m/z $[M + H]^+$ (unless otherwise indicated) |
|---|---|---|---|
| | Method of preparation and physicochemical properties for Examples 13-112 | | |
| 48 | Method A; C5 | 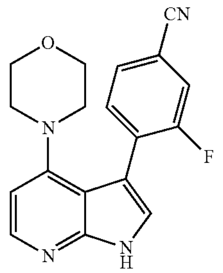 [SMILES: N#Cc1ccc(-c2c[nH]c3nccc(N4CCOCC4)c23)c(F)c1] | 2.37 minutes[5]; 323 |
| 49 | Method A; C5 | 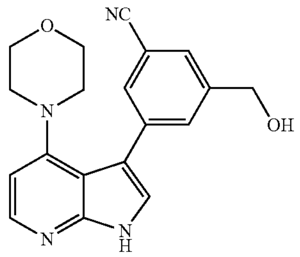 [SMILES: N#Cc1cc(CO)cc(-c2c[nH]c3nccc(N4CCOCC4)c23)c1] | 2.15 minutes[5]; 335 |
| 50 | Method A; C5 | 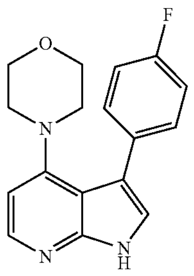 [SMILES: Fc1ccc(-c2c[nH]c3nccc(N4CCOCC4)c23)cc1] | 2.26 minutes[4]; 298 |
| 51 | Method A; C31 | 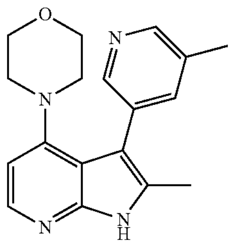 [SMILES: Cc1cncc(-c2c(C)[nH]c3nccc(N4CCOCC4)c23)c1] | 1.77 minutes[5]; 309 |
| 52 | Method A; C31 | 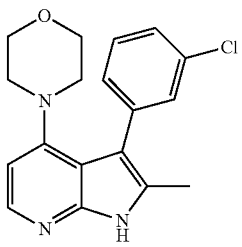 [SMILES: Cc1[nH]c2nccc(N3CCOCC3)c2c1-c1cccc(Cl)c1] | 2.51 minutes[4]; 328 |

TABLE 1-continued

Method of preparation and physicochemical properties for Examples 13-112

| Example Number | Method of Preparation; Non-commercial starting materials | Structure | $^1H$ NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
|---|---|---|---|
| 53 | Method A; C31 | 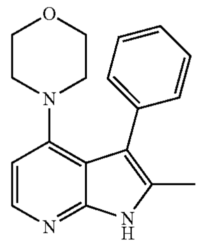 [SMILES: Cc1[nH]c2nccc(N3CCOCC3)c2c1-c1ccccc1] | 2.28 minutes[4]; 294 |
| 54 | Method A; C31 | 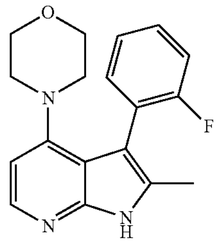 [SMILES: Cc1[nH]c2nccc(N3CCOCC3)c2c1-c1ccccc1F] | 2.24 minutes[4]; 312 |
| 55 | Method A; C31 | 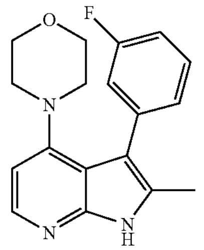 [SMILES: Cc1[nH]c2nccc(N3CCOCC3)c2c1-c1cccc(F)c1] | 2.30 minutes[4]; 312 |
| 56 | Method A; C31 | 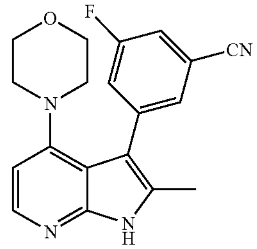 [SMILES: Cc1[nH]c2nccc(N3CCOCC3)c2c1-c1cc(F)cc(C#N)c1] | 2.44 minutes[5]; 337 |
| 57 | Method B; C47 | 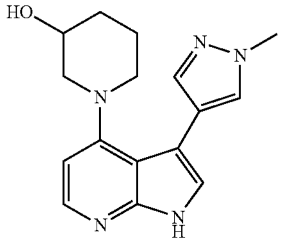 [SMILES: Cn1cc(-c2c[nH]c3nccc(N4CCCC(O)C4)c23)cn1] | 1.89 minutes[5]; 298 |

TABLE 1-continued

| Example Number | Method of Preparation; Non-commercial starting materials | Structure | $^1H$ NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
| --- | --- | --- | --- |
| Method of preparation and physicochemical properties for Examples 13-112 | | | |
| 58 | Method B; C47 | 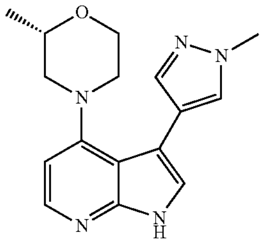 | 1.98 minutes[5]; 298 |
| 59 | Method B; C47 | 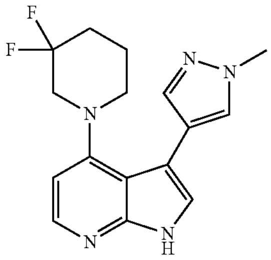 [SMILES: Cn1cc(-c2c[nH]c3nccc(N4CCCC(F)(F)C4)c23)cn1] | 2.17 minutes[5]; 318 |
| 60 | Method B; C47 | 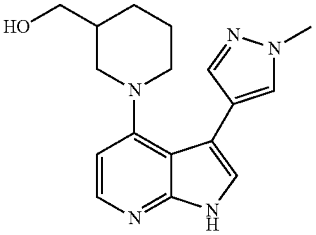 [SMILES: Cn1cc(-c2c[nH]c3nccc(N4CCCC(CO)C4)c23)cn1] | 1.99 minutes[5]; 312 |
| 61 | Method B; C47 | 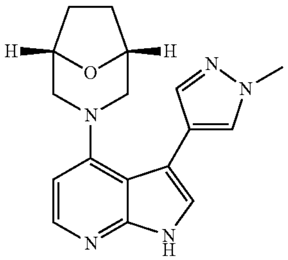 [SMILES: Cn1cc(-c2c[nH]c3nccc(N4C[C@H]5CC[C@@H](C4)O5)c23)cn1] | 2.09 minutes[5]; 310 |
| 62 | Method B; C47 | 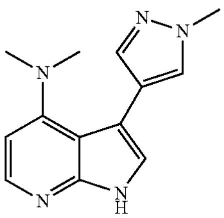 [SMILES: CN(C)c1ccnc2[nH]cc(-c3cnn(C)c3)c12] | 1.93 minutes[5]; 242 |

TABLE 1-continued

| Method of preparation and physicochemical properties for Examples 13-112 | | | |
|---|---|---|---|
| Example Number | Method of Preparation; Non-commercial starting materials | Structure | $^1$H NMR (400 MHz, $CDCl_3$) δ (ppm); Mass spectrum, observed ion m/z (M + H$^+$) or HPLC retention time; Mass spectrum m/z [M + H]$^+$ (unless otherwise indicated) |
| 63 | Method B; C47 | 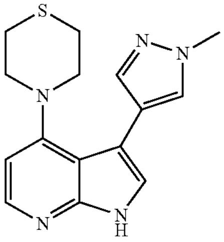 [SMILES: Cn1cc(-c2c[nH]c3nccc(N4CCSCC4)c23)cn1] | 2.10 minutes[5]; 300 |
| 64 | Method B; C47 | 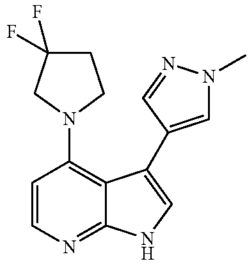 [SMILES: Cn1cc(-c2c[nH]c3nccc(N4CCC(F)(F)C4)c23)cn1] | 2.37 minutes[7]; 304 |
| 65 | Method C; C2 | 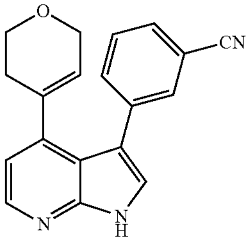 [SMILES: N#Cc1cccc(-c2c[nH]c3nccc(C4=CCOCC4)c23)c1] | 2.47 minutes[5]; 302 |
| 66 | Method D; C2 | 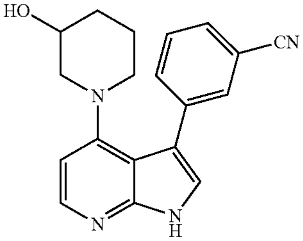 [SMILES: N#Cc1cccc(-c2c[nH]c3nccc(N4CCCC(O)C4)c23)c1] | 1.80 minutes[8], 319.3 |
| 67 | Method D; C2 | 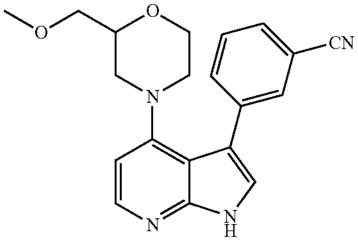 [SMILES: COCC1CN(c2ccnc3[nH]cc(-c4cccc(C#N)c4)c23)CCO1] | 2.36 minutes[5]; 349 |

TABLE 1-continued

| Method of preparation and physicochemical properties for Examples 13-112 | | | |
|---|---|---|---|
| Example Number | Method of Preparation; Non-commercial starting materials | Structure | $^1H$ NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
| 68 | Example 9[1,9,10]; C5 | 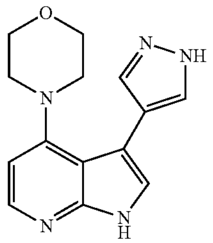 [SMILES: c1cc(N2CCOCC2)c2c(-c3cn[nH]c3)c[nH]c2n1] | $^1H$ NMR (400 MHz, DMSO-$d_6$) δ 12.7 (v br s, 1H), 11.65 (v br s, 1H), 8.07 (d, J = 5.3 Hz, 1H), 7.78 (s, 2H), 7.34 (s, 1H), 6.60 (d, J = 5.4 Hz, 1H), 3.49-3.55 (m, 4H), 2.84-2.91 (m, 4H); 270.2 |
| 69 | Method D; C2 | 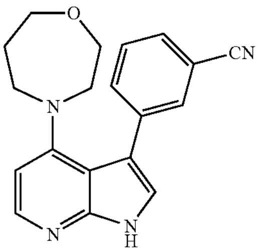 [SMILES: N#Cc1cccc(-c2c[nH]c3nccc(N4CCCOCC4)c23)c1] | 2.37 minutes[5]; 319 |
| 70 | Method D; C2 | 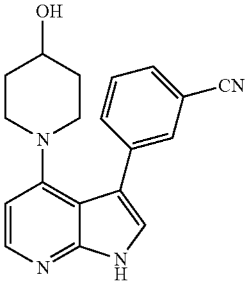 [SMILES: N#Cc1cccc(-c2c[nH]c3nccc(N4CCC(O)CC4)c23)c1] | 2.23 minutes[5]; 319 |
| 71 | Method D; C2 | 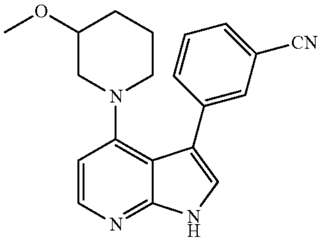 [SMILES: COC1CCCN(c2ccnc3[nH]cc(-c4cccc(C#N)c4)c23)C1] | 2.30 minutes[4]; 333 |
| 72 | Method D; C2 | 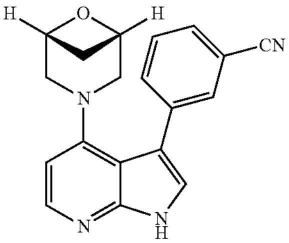 [SMILES: N#Cc1cccc(-c2c[nH]c3nccc(N4C[C@H]5C[C@@H](C4)O5)c23)c1] | 2.29 minutes[5]; 317 |

TABLE 1-continued

| Example Number | Method of Preparation; Non-commercial starting materials | Structure | $^1$H NMR (400 MHz, $CDCl_3$) δ (ppm); Mass spectrum, observed ion m/z ($M + H^+$) or HPLC retention time; Mass spectrum m/z $[M + H]^+$ (unless otherwise indicated) |
|---|---|---|---|
| Method of preparation and physicochemical properties for Examples 13-112 | | | |
| 73 | Method D; C2 | 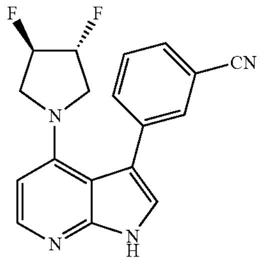 [SMILES: N#Cc1cccc(-c2c[nH]c3nccc(N4C[C@@H](F)[C@H](F)C4)c23)c1] | 2.20 minutes[4]; 325 |
| 74 | Method D; C2 | 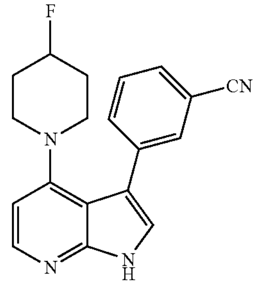 [SMILES: N#Cc1cccc(-c2c[nH]c3nccc(N4CCC(F)CC4)c23)c1] | 2.31 minutes[4]; 321 |
| 75 | Method D; C2 | 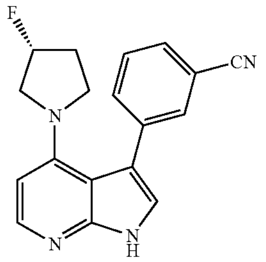 [SMILES: N#Cc1cccc(-c2c[nH]c3nccc(N4CC[C@@H](F)C4)c23)c1] | 2.18 minutes[4]; 307 |
| 76 | Method D; C2 | 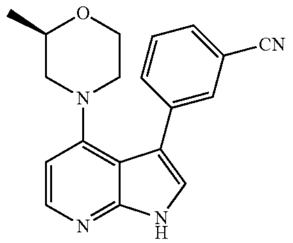 [SMILES: C[C@@H]1CN(c2ccnc3[nH]cc(-c4cccc(C#N)c4)c23)CCO1] | 2.44 minutes[5]; 319 |
| 77 | Method D; C2 | 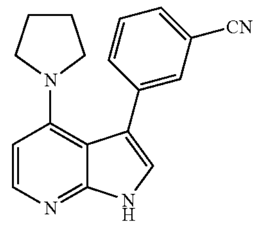 [SMILES: N#Cc1cccc(-c2c[nH]c3nccc(N4CCCC4)c23)c1] | 2.29 minutes[4]; 289 |

TABLE 1-continued

| Method of preparation and physicochemical properties for Examples 13-112 | | | |
|---|---|---|---|
| Example Number | Method of Preparation; Non-commercial starting materials | Structure | $^1$H NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
| 78 | Method D; C2 | 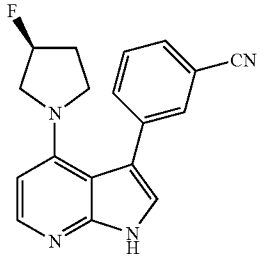 [SMILES: N#Cc1cccc(-c2c[nH]c3nccc(N4CC[C@H](F)C4)c23)c1] | 2.18 minutes[4]; 307 |
| 79 | Method D; C2 | 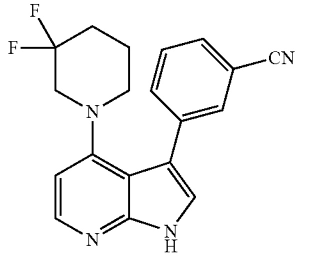 [SMILES: N#Cc1cccc(-c2c[nH]c3nccc(N4CCCC(F)(F)C4)c23)c1] | 2.38 minutes[4]; 339 |
| 80 | Method D; C2 | 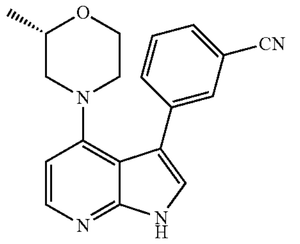 [SMILES: C[C@H]1CN(c2ccnc3[nH]cc(-c4cccc(C#N)c4)c23)CCO1] | 2.43 minutes[5]; 319 |
| 81 | Example 3[11,12] | 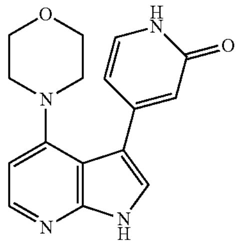 [SMILES: O=c1cc(-c2c[nH]c3nccc(N4CCOCC4)c23)cc[nH]1] | $^1$H NMR (400 MHz, DMSO-$d_6$) δ 8.13 (d, J = 5.0 Hz, 1H), 7.74 (s, 1H), 7.35 (d, J = 7.0 Hz, 1H), 6.69 (d, J = 5.5 Hz, 1H), 6.62 (s, 1H), 6.50 (br d, J = 6.5 Hz, 1H), 3.60-3.68 (m, 4H), 2.89-2.98 (m, 4H); 296.9 |
| 82 | Example 10[13,14] | 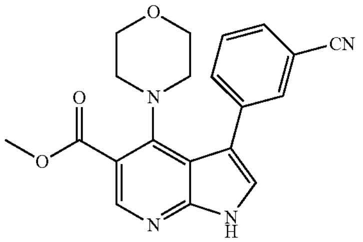 [SMILES: COC(=O)c1cnc2[nH]cc(-c3cccc(C#N)c3)c2c1N1CCOCC1] | $^1$H NMR (600 MHz, DMSO-$d_6$) δ 8.28 (s, 1H), 7.94-7.96 (m, 1H), 7.84 (br d, J = 7.8 Hz, 1H), 7.80 (br d, J = 7.7 Hz, 1H), 7.64 (dd, J = 7.8, 7.8 Hz, 1H), 7.57 (s, 1H), 3.88 (s, 3H), 3.09-3.13 (m, 4H), 2.91-2.95 (m, 4H); 363.1 |

TABLE 1-continued

Method of preparation and physicochemical properties for Examples 13-112

| Example Number | Method of Preparation; Non-commercial starting materials | Structure | $^1$H NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
|---|---|---|---|
| 83 | C40[15] | 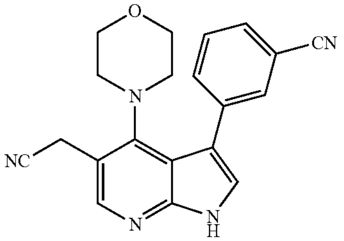 [SMILES: N#CCc1cnc2[nH]cc(-c3cccc(C#N)c3)c2c1N1CCOCC1] | $^1$H NMR (600 MHz, DMSO-$d_6$) δ 8.16 (s, 1H), 7.89 (dd, J = 1.6, 1.2 Hz, 1H), 7.78-7.82 (m, 2H), 7.64 (dd, J = 7.8, 7.7 Hz, 1H), 7.51 (d, J = 2.6 Hz, 1H), 4.12 (s, 2H), 3.12-3.22 (br m, 4H), 3.05 (br s, 4H); 344.3 |
| 84 | C37[16] | 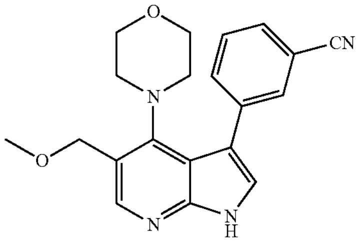 [SMILES: COCc1cnc2[nH]cc(-c3cccc(C#N)c3)c2c1N1CCOCC1] | $^1$H NMR (600 MHz, DMSO-$d_6$) δ 8.10 (s, 1H), 7.90 (br dd, J = 1.6, 1.3 Hz, 1H), 7.82 (ddd, J = 7.7, 1.6, 1.2 Hz, 1H), 7.78 (ddd, J = 7.7, 1.6, 1.2 Hz, 1H), 7.62 (br dd, J = 7.8, 7.7 Hz, 1H), 7.47 (d, J = 2.5 Hz, 1H), 4.56 (s, 2H) 3.24 (s, 3H), 3.12 (br s, 4H), 2.96-3.01 (m, 4H); 349.2 |
| 85 | 4[17] | 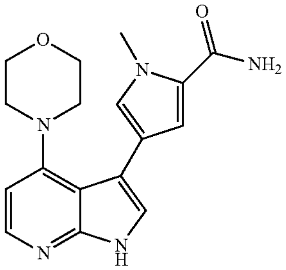 [SMILES: Cn1cc(-c2c[nH]c3nccc(N4CCOCC4)c23)cc1C(N)=O] | $^1$H NMR (400 MHz, DMSO-$d_6$) δ 11.53 (br s, 1H), 8.05 (d, J = 5.3 Hz, 1H), 7.21-7.23 (m, 1H), 7.09 (d, J = 1.6 Hz, 1H), 7.03 (d, J = 1.9 Hz, 1H), 6.59 (d, J = 5.3 Hz, 1H), 3.90 (s, 3H), 3.53-3.58 (m, 4H), 2.88-2.94 (m, 4H); 325.9 |
| 86 | Example 5; C15 | 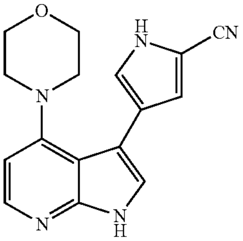 [SMILES: N#Cc1cc(-c2c[nH]c3nccc(N4CCOCC4)c23)c[nH]1] | $^1$H NMR (400 MHz, DMSO-$d_6$) δ 12.31 (br s, 1H), 11.65 (br s, 1H), 8.30 (br s, 1H), 8.07 (d, J = 5.2 Hz, 1H), 7.36 (d, J = 2.4 Hz, 1H), 7.34 (br s, 1H), 7.11 (br s, 1H), 6.62 (d, J = 5.4 Hz, 1H), 3.51-3.56 (m, 4H), 2.86-2.91 (m, 4H); 293.9 |
| 87 | Example 4; C31 C9 | 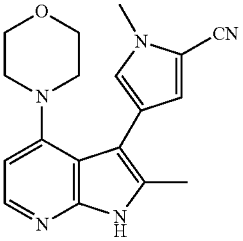 [SMILES: Cc1[nH]c2nccc(N3CCOCC3)c2c1-c1cc(C#N)n(C)c1] | $^1$H NMR (400 MHz, DMSO-$d_6$), characteristic peaks: δ 11.52 (br s, 1H), 7.96 (d, J = 5.3 Hz, 1H), 7.22 (d, J = 1.6 Hz, 1H), 6.98 (d, J = 1.8 Hz, 1H), 6.55 (d, J = 5.4 Hz, 1H), 3.82 (s, 3H), 2.77-2.85 (m, 4H), 2.31 (s, 3H); 321.9 |

TABLE 1-continued

Method of preparation and physicochemical properties for Examples 13-112

| Example Number | Method of Preparation; Non-commercial starting materials | Structure | $^{1}H$ NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
|---|---|---|---|
| 88 | Method C; C2 | 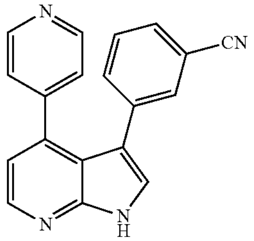 [SMILES: N#Cc1cccc(-c2c[nH]c3nccc(-c4ccncc4)c23)c1] | 2.09 minutes[5]; 297 |
| 89 | Method C; C47 | 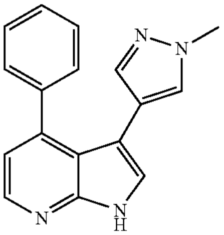 [SMILES: Cn1cc(-c2c[nH]c3nccc(-c4ccccc4)c23)cn1] | 2.31 minutes[5]; 275 |
| 90 | Example 6[18]; C25 | 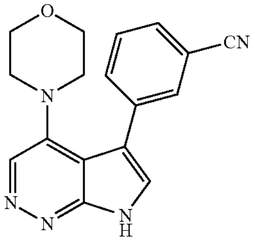 [SMILES: N#Cc1cccc(-c2c[nH]c3nncc(N4CCOCC4)c23)c1] | $^{1}H$ NMR (400 MHz, DMSO-$d_6$) δ 8.67 (s, 1H), 8.08 (s, 1H), 8.06-8.08 (m, 1H), 7.97 (br d, J = 7.9 Hz, 1H), 7.78 (br d, J = 8 Hz, 1H), 7.69 (dd, J = 7.7, 7.6 Hz, 1H), 3.46-3.53 (m, 4H), 2.92-2.99 (m, 4H); 305.8 |
| 91 | Method C; C2 | 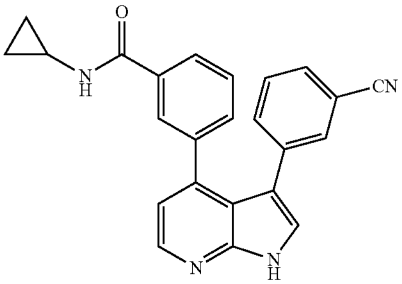 [SMILES: N#Cc1cccc(-c2c[nH]c3nccc(-c4cccc(C(=O)NC5CC5)c4)c23)c1] | 2.30 minutes[4]; 379 |
| 92 | Example 6[18]; C25 | 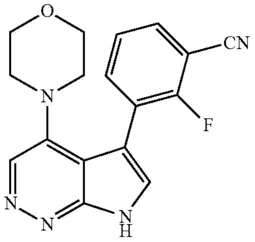 [SMILES: N#Cc1cccc(-c2c[nH]c3nncc(N4CCOCC4)c23)c1F] | $^{1}H$ NMR (400 MHz, DMSO-$d_6$ + $D_2O$) δ 8.63 (s, 1H), 7.99 (s, 1H), 7.84-7.93 (m, 2H), 7.54 (dd, J = 7.8, 7.6 Hz, 1H), 3.30-3.37 (m, 4H), 2.87-2.93 (m, 4H); 323.9 |

TABLE 1-continued

| Example Number | Method of Preparation; Non-commercial starting materials | Structure | $^1$H NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
|---|---|---|---|
| Method of preparation and physicochemical properties for Examples 13-112 | | | |
| 93 | Method C; C2 | 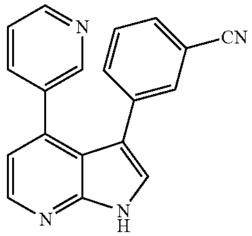 [SMILES: N#Cc1cccc(-c2c[nH]c3nccc(-c4cccnc4)c23)c1] | 2.15 minutes[5]; 297 |
| 94 | Method C; C47 | 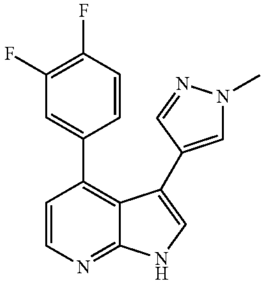 [SMILES: Cn1cc(-c2c[nH]c3nccc(-c4ccc(F)c(F)c4)c23)cn1] | 2.50 minutes[5]; 311 |
| 95 | Method C; C47 | 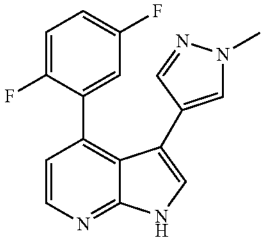 [SMILES: Cn1cc(-c2c[nH]c3nccc(-c4cc(F)ccc4F)c23)cn1] | 2.49 minutes[5]; 311 |
| 96 | Method C; C47 | 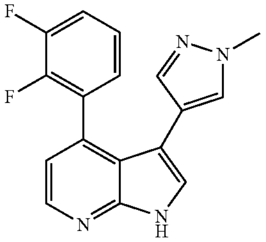 [SMILES: Cn1cc(-c2c[nH]c3nccc(-c4cccc(F)c4F)c23)cn1] | 2.50 minutes[5]; 311 |
| 97 | Method C; C47 | 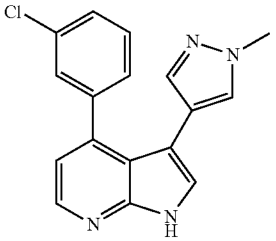 [SMILES: Cn1cc(-c2c[nH]c3nccc(-c4cccc(Cl)c4)c23)cn1] | 2.29 minutes[4]; 309 |

TABLE 1-continued

| Method of preparation and physicochemical properties for Examples 13-112 | | | |
|---|---|---|---|
| Example Number | Method of Preparation; Non-commercial starting materials | Structure | $^1H$ NMR (400 MHz, $CDCl_3$) δ (ppm); Mass spectrum, observed ion m/z $(M + H^+)$ or HPLC retention time; Mass spectrum m/z $[M + H]^+$ (unless otherwise indicated) |
| 98 | Method C; C47 | 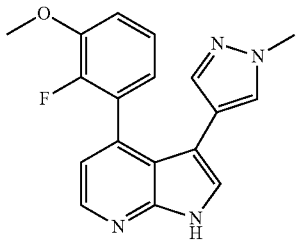 | 2.36 minutes[5]; 323 |
| 99 | Method C; C2 | 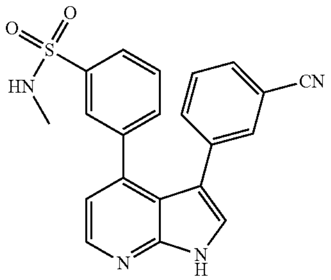 [SMILES: CNS(=O)(=O)c1cccc(-c2ccnc3[nH]cc(-c4cccc(C#N)c4)c23)c1] | 2.57 minutes[5]; 389 |
| 100 | Example 11[19,20] | 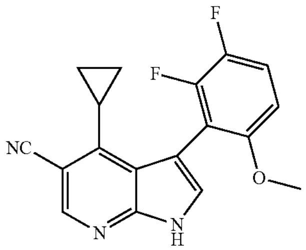 [SMILES: COc1ccc(F)c(F)c1-c1c[nH]c2ncc(C#N)c(C3CC3)c12] | 10.08 (br s, 1H), 8.53 (s, 1H), 7.44 (d, J = 2.4 Hz, 1H), 7.18 (ddd, J = 9, 9, 9 Hz, 1H), 6.67 (ddd, J = 9.1, 3.6, 1.8 Hz, 1H), 3.75 (s, 3H), 2.00-2.09 (m, 1H), 0.69-0.77 (m, 1H), 0.60-0.69 (m, 2H), 0.49-0.58 (m, 1H); 325.9 |
| 101 | Method C[21]; C2 | 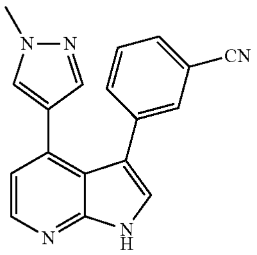 [SMILES: Cn1cc(-c2ccnc3[nH]cc(-c4cccc(C#N)c4)c23)cn1] | 2.25 minutes[5]; 300 |
| 102 | Method C; C47 | 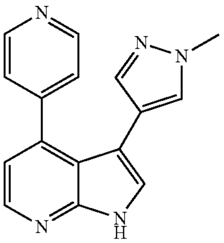 [SMILES: Cn1cc(-c2c[nH]c3nccc(-c4ccncc4)c23)cn1] | 1.73 minutes[5]; 276 |

TABLE 1-continued

Method of preparation and physicochemical properties for Examples 13-112

| Example Number | Method of Preparation; Non-commercial starting materials | Structure | $^{1}H$ NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
|---|---|---|---|
| 103 | Method C; C47 | 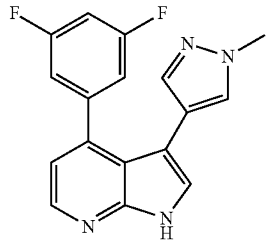 [SMILES: Cn1cc(-c2c[nH]c3nccc(-c4cc(F)cc(F)c4)c23)cn1] | 2.55 minutes[5]; 311 |
| 104 | Method C; C47 | 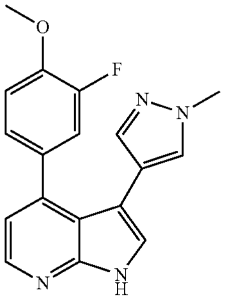 [SMILES: COc1ccc(-c2ccnc3[nH]cc(-c4cnn(C)c4)c23)cc1F] | 2.37 minutes[5]; 323 |
| 105 | Method C; C47 | 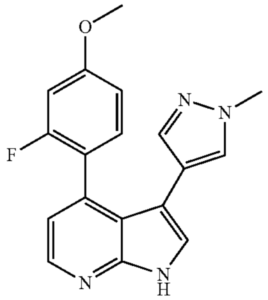 [SMILES: COc1ccc(-c2ccnc3[nH]cc(-c4cnn(C)c4)c23)c(F)c1] | 2.48 minutes[7]; 323 |
| 106 | Method C[21]; C47 | 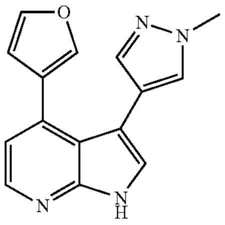 [SMILES: Cn1cc(-c2c[nH]c3nccc(-c4ccoc4)c23)cn1] | 2.12 minutes[5]; 265 |
| 107 | Method C; C47 | 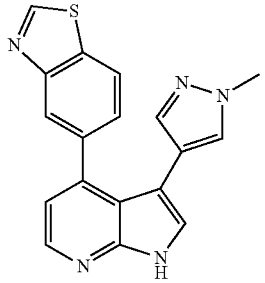 [SMILES: Cn1cc(-c2c[nH]c3nccc(-c4ccc5scnc5c4)c23)cn1] | 2.22 minutes[5]; 332 |

TABLE 1-continued

| Method of preparation and physicochemical properties for Examples 13-112 | | | |
|---|---|---|---|
| Example Number | Method of Preparation; Non-commercial starting materials | Structure | $^1$H NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
| 108 | Method C; C47 | 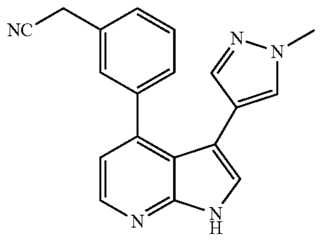 [SMILES: Cn1cc(-c2c[nH]c3nccc(-c4cccc(CC#N)c4)c23)cn1] | 2.24 minutes[5]; 314 |
| 109 | Method C; C47 | 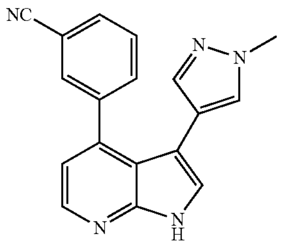 [SMILES: Cn1cc(-c2c[nH]c3nccc(-c4cccc(C#N)c4)c23)cn1] | 2.31 minutes[5]; 300 |
| 110 | Example 6[18]; C25 | 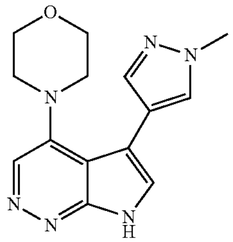 [SMILES: Cn1cc(-c2c[nH]c3nncc(N4CCOCC4)c23)cn1] | $^1$H NMR (400 MHz, DMSO-$d_6$) δ 12.38 (br s, 1H), 8.57 (s, 1H), 7.88 (s, 1H), 7.74 (s, 1H), 7.64 (s, 1H), 3.90 (s, 3H), 3.56-3.62 (m, 4H), 2.97-3.04 (m, 4H); 284.9 |
| 111 | Method C; C47 | 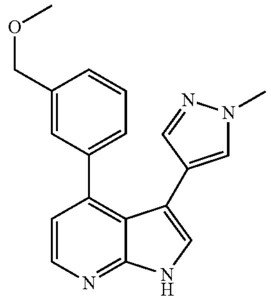 [SMILES: COCc1cccc(-c2ccnc3[nH]cc(-c4cnn(C)c4)c23)c1] | 2.30 minutes[5]; 319 |

TABLE 1-continued

Method of preparation and physicochemical properties for Examples 13-112

| Example Number | Method of Preparation; Non-commercial starting materials | Structure | $^1H$ NMR (400 MHz, $CDCl_3$) δ (ppm); Mass spectrum, observed ion m/z (M + $H^+$) or HPLC retention time; Mass spectrum m/z $[M + H]^+$ (unless otherwise indicated) |
|---|---|---|---|
| 112 | Method C; C2 | 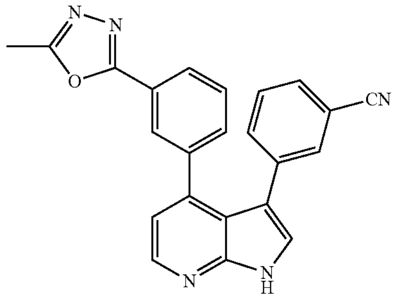 [SMILES: Cc1nnc(-c2cccc(-c3ccnc4[nH]cc(-c5cccc(C#N)c5)c34)c2)o1] | 2.65 minutes[5]; 378 |

[1]In this case, potassium phosphate was used in place of cesium carbonate in the Suzuki reaction.

[2]1-Methyl-4-(4,4,5,5-tetramethyl-1,3,2-dioxaborolan-2-yl)-1H-pyrazole was employed.

[3]The requisite 3-bromo-4-(dimethylamino)-1-{[2-(trimethylsilyl)ethoxy]methyl}-1H-pyrrolo[2,3-b]pyridine-5-carbonitrile was prepared as follows: 4-chloro-1H-pyrrolo[2,3-b]pyridine-5-carbonitrile was protected as its 2-(trimethylsilyl)ethoxy]methyl derivative. Nucleophilic aromatic substitution with dimethylamine afforded 4-(dimethylamino)-1-{[2-(trimethylsilyl)ethoxy]methyl}-1H-pyrrolo[2,3-b]pyridine-5-carbonitrile, which was brominated with N-bromosuccinimide.

[4]Conditions for analytical HPLC. Column: Waters XBridge C18, 2.1 x 50 mm, 5 μm; Mobile phase A: 0.0375% trifluoroacetic acid in water; Mobile phase B: 0.01875% trifluoroacetic acid in acetonitrile; Gradient: 10% B for 0.5 minutes, then linear to 100% B over 3.5 minutes; Flow rate: 0.8 mL/minute.

[5]Conditions for analytical HPLC. Identical to footnote 4, except that the gradient used was 1% to 5% B over 0.60 minutes, then 5% to 100% B over 3.40 minutes.

[6]1-Methyl-4-(4,4,5,5-tetramethyl-1,3,2-dioxaborolan-2-yl)-1H-pyrazole was employed.

[7]Conditions for analytical HPLC. Column: Water XBridge C18, 2.1 x 50 mm, 5 μm; Mobile phase A: 0.05% ammonium hydroxide in water; Mobile phase B: acetonitrile; Gradient 5% B for 0.5 minutes, then linear to 100% B over 2.9 minutes; Flow rate: 0.8 mL/minute.

[8]Conditions for analytical HPLC. Column: Waters Atlantis dC18, 4.6 x 50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

[9]1-(Tetrahydro-2H-pyran-2-yl)-4-(4,4,5,5-tetramethyl-1,3,2-dioxaborolan-2-yl)-1H-pyrazole was employed in the Suzuki reaction.

[10]Prior to the potassium hydroxide-mediated cleavage of the (4-methylphenyl)sulfonyl group, the tetrahydro-2H-pyran-2-yl moiety was removed via treatment with hydrogen chloride in 1,4-dioxane.

[11]In the case, [1,1'-bis(diphenylphosphino)ferrocene]dichloropalladium(II) and cesium carbonate were used in place of tetrakis(triphenylphosphine)palladium(0) and triethylamine

[12]4-Iodopyridin-2(1H)-one was employed.

[13]Methyl 4-chloro-1H-pyrrolo[2,3-b]pyridine-5-carboxylate was employed as starting material.

[14]In this case, the Suzuki reaction was carried out with dichlorobis(triphenylphosphine)palladium(II) and potassium carbonate, in place of [1,1'-bis(diphenylphosphino)ferrocene]dichloropalladium(II) and potassium phosphate. The sodium borohydride reduction of Example 10 was unnecessary for synthesis of this Example.

[15]Compound C40 was converted to Example 83 via reaction with isocyanomethyl 4-methylphenyl sulfone, using the method described by C. Chen et al., *J. Med. Chem.* 2004, 47, 4787-4798.

[16]Compound C37 was N-protected with a trityl group, then reacted with morpholine and cesium fluoride at elevated temperature to afford 3-iodo-4-(morpholin-4-yl)-1-trityl-1H-pyrrolo[2,3-b]pyridine-5-carbaldehyde; Suzuki reaction with (3-cyanophenyl)boronic acid in the presence of dichlorobis(triphenylphosphine)palladium(II) and potassium carbonate, followed by sodium borohydride reduction, gave 3-[5-(hydroxymethyl)-4-(morpholin-4-yl)-1-trityl-1H-pyrrolo[2,3-b]pyridin-3-yl]benzonitrile. This was alkylated using sodium hydride and methyl iodide, then deprotected with trifluoroacetic acid, to afford Example 84.

[17]The compound of Example 4 was subjected to sulfuric acid at 55° C. to provide Example 85.

[18]In this case, the Suzuki reaction was carried out with dichlorobis(triphenylphosphine)palladium(II) and potassium carbonate.

[19]4-Chloro-1H-pyrrolo[2,3-b]pyridine-5-carbonitrile was protected as its 2-(trimethylsilyl)ethoxy]methyl derivative. Subsequent Negishi coupling with cyclopropylzinc bromide in the presence of tetrakis(triphenylphosphine)palladium(0) provided 4-cyclopropyl-1-{[2-(trimethylsilyl)ethoxy]methyl}-1H-pyrrolo[2,3-b]pyridine-5-carbonitrile, which was brominated with N-bromosuccinimide to afford the requisite 3-bromo-4-cyclopropyl-1-{[2-(trimethylsilyl)ethoxy]methyl}-1H-pyrrolo[2,3-b]pyridine-5-carbonitrile.

[20]The second step in the protecting group removal was carried out with ammonium hydroxide in methanol, rather than potassium carbonate.

[21]In this case, the Suzuki reaction was carried out at 120° C.

Biological Assays

LRRK2 Assay

LRRK2 kinase activity was measured using Lantha Screen technology from Invitrogen. GST-tagged truncated LRRK2 from Invitrogen (Cat # PV4874) was incubated with a fluorescein-labeled peptide substrate based upon ezrin/radixin/moesin (ERM), also known as LRRKtide (Invitrogen cat # PR8976A), in the presence of a dose response of compound. Upon completion, the assay was stopped and detected with a terbium labeled anti-phospho-ERM antibody (Invitrogen, cat # PR8975A). The assay was carried out under the following protocol: 3 μL of a working solution of substrate (233 nM LRRKtide, 117 μM ATP) prepared in assay buffer (50 mM HEEPES, pH 7.5, 3 mM $MgCl_2$, with 2 mM DTT and 0.01% Brij35 added fresh) was added to a low volume Greiner 384-well plate. The compound dose response was prepared by diluting compound to a top concentration of 3.16 mM in 100% DMSO and serial diluted by half-log in DMSO 11 times. Aliquots (3.5 μL) of the 100% DMSO dose response were mixed with 46.5 μL water then 1 μL of this mixture was added to the 3 μL substrate mix in the 384-well plate. The kinase reaction was started with 3 μL of a working solution of LRRK2 enzyme at a concentration of 4 μg/mL. The final reaction concentrations were 100 nM LRRKtide, 50 μM ATP, 1.7 μg/mL LRRK2 enzyme and a compound dose response with a top dose of 32 μM. The reaction was allowed to progress at room temperature for two hours and then stopped with the addition of 7 μL of detection buffer (20 mM Tris pH 7.6, 0.01% NP-40, 0.02% $NaN_3$, 6 mM EDTA with 2 nM terbium labeled anti-phospho-ERM). After an incubation of 1 hour at room temperature, the plate was read on an Envision with an excitation wavelength of 340 nm and a reading emission at both 520 nm and 495 nm. The ratio of the 520 nm and 495 nm emission was used to analyze the data.

Inhibition of mutant G2019S LRRK2 (Invitrogen cat # PV4881) was measured in the exact same method. All final concentrations of substrate ATP and enzyme were the same. However, since the mutant enzyme is more active the reaction time was reduced to 90 minutes to ensure that inhibition was measured at steady state before any substrate depletion could occur.

Table 2, below, provides the LRRK2 $IC_{50}$ data for the compounds of the invention.

TABLE 2

Biology data and IUPAC names for Examples 1-112.

| Example Number | LRRK2 LANTHA $EC_{50}$ at 1 mM ATP; Geometric mean of 2-3 determinations unless otherwise indicated | Mutant LRRK2 LANTHA $EC_{50}$ at 1 mM ATP; Geometric mean of 2-3 determinations unless otherwise indicated | IUPAC Name |
|---|---|---|---|
| 1 | 4.28[a] | 15.8[a] | 3-[4-(morpholin-4-yl)-1H-pyrrolo[2,3-b]pyridin-3-yl]benzonitrile |
| 2 | 5.17 | 7.54 | 2-fluoro-3-[4-(morpholin-4-yl)-1H-pyrrolo[2,3-b]pyridin-3-yl]benzonitrile |
| 3 | 14.0 | 25.0 | 3-[4-(morpholin-4-yl)-1H-pyrrolo[2,3-b]pyridin-3-yl]imidazo[1,2-b]pyridazine |
| 4 | 2.85[a] | 3.13[a] | 1-methyl-4-[4-(morpholin-4-yl)-1H-pyrrolo[2,3-b]pyridin-3-yl]-1H-pyrrole-2-carbonitrile |
| 5 | 5.26 | 16.8 | 1-methyl-4-[4-(morpholin-4-yl)-1H-pyrrolo[2,3-b]pyridin-3-yl]-1H-imidazole-2-carbonitrile |
| 6 | 14.2 | 78.8 | 1-methyl-4-[4-(morpholin-4-yl)-7H-pyrrolo[2,3-c]pyridazin-5-yl]-1H-pyrrole-2-carbonitrile |
| 7 | 1.30 | 1.27 | 4-[2-chloro-4-(morpholin-4-yl)-1H-pyrrolo[2,3-b]pyridin-3-yl]-1-methyl-1H-pyrrole-2-carbonitrile |
| 8 | 22.1 | 59.0 | 3-[2-methyl-4-(morpholin-4-yl)-1H-pyrrolo[2,3-b]pyridin-3-yl]benzonitrile, trifluoroacetate salt |
| 9 | 208[a] | 1000[a] | 3-[6-methyl-4-(morpholin-4-yl)-1H-pyrrolo[2,3-b]pyridin-3-yl]benzonitrile |
| 10 | 79.8 | 349 | 3-[5-[hydroxymethyl)-4-(morpholin-4-yl)-1H-pyrrolo[2,3-b]pyridin-3-yl]benzonitrile |
| 11 | 24.2 | 130 | 3-(3-cyanophenyl)-4-(morpholin-4-yl)-1H-pyrrolo[2,3-b]pyridine-5-carbonitrile |
| 12 | 59.6 | 126 | 4-(3,6-dihydro-2H-pyran-4-yl)-3-(1-methyl-1H-pyrazol-4-yl)-1H-pyrrolo[2,3-b]pyridine |
| 13 | 26.5[a] | 47.5[a] | 3-(1-methyl-1H-pyrazol-4-yl)-4-(morpholin-4-yl)-1H-pyrrolo[2,3-b]pyridine |
| 14 | 25.9 | 64.1 | 3-(3-cyano-2-fluorophenyl)-4-(dimethylamino)-1H-pyrrolo[2,3-b]pyridine-5-carbonitrile |
| 15 | 92.3[a] | 113 | 3-(5-fluoro-2-methoxyphenyl)-4-(morpholin-4-yl)-1H-pyrrolo[2,3-b]pyridine, formate salt |
| 16 | 44.3[a] | 54.8[a] | 3-(3-fluoro-5-methoxyphenyl)-4-(morpholin-4-yl)-1H-pyrrolo[2,3-b]pyridine, formate salt |
| 17 | 137[a] | 226[a] | 2-methyl-3-(1-methyl-1H-pyrazol-4-yl)-4-(morpholin-4-yl)-1H-pyrrolo[2,3-b]pyridine |
| 18 | 95.4 | 461 | 2-fluoro-3-[6-methyl-4-(morpholin-4-yl)-1H-pyrrolo[2,3-b]pyridin-3-yl]benzonitrile, formate salt |
| 19 | 47.5 | 131 | 6-[4-(morpholin-4-yl)-1H-pyrrolo[2,3-b]pyridin-3-yl]pyridine-2-carbonitrile |
| 20 | 53.7 | 33.8 | 3-(3-chlorophenyl)-4-(morpholin-4-yl)-1H-pyrrolo[2,3-b]pyridine, formate salt |
| 21 | 51.5 | 27.2 | 3-(3-chloro-5-fluorophenyl)-4-(morpholin-4-yl)-1H-pyrrolo[2,3-b]pyridine, formate salt |
| 22 | 130[a] | 115[a] | 3-(2,5-difluorophenyl)-4-(morpholin-4-yl)-1H-pyrrolo[2,3-b]pyridine, formate salt |
| 23 | 143[a] | 111[a] | 3-(2-chlorophenyl)-4-(morpholin-4-yl)-1H-pyrrolo[2,3-b]pyridine, formate salt |
| 24 | 16.8 | 18.9 | 3-(2,3-difluorophenyl)-4-(morpholin-4-yl)-1H-pyrrolo[2,3-b]pyridine, formate salt |
| 25 | 34.5 | 26.9 | 3-(3-fluorophenyl)-4-(morpholin-4-yl)-1H-pyrrolo[2,3-b]pyridine, formate salt |

TABLE 2-continued

Biology data and IUPAC names for Examples 1-112.

| Example Number | LRRK2 LANTHA $EC_{50}$ at 1 mM ATP; Geometric mean of 2-3 determinations unless otherwise indicated | Mutant LRRK2 LANTHA $EC_{50}$ at 1 mM ATP; Geometric mean of 2-3 determinations unless otherwise indicated | IUPAC Name |
|---|---|---|---|
| 26 | 29.0[a] | 21.7[a] | 3-(2-fluorophenyl)-4-(morpholin-4-yl)-1H-pyrrolo[2,3-b]pyridine, formate salt |
| 27 | 57.6 | 46.9 | 3-(5-chloro-2-fluorophenyl)-4-(morpholin-4-yl)-1H-pyrrolo[2,3-b]pyridine, formate salt |
| 28 | 96.3 | 64.8 | {3-[4-(morpholin-4-yl)-1H-pyrrolo[2,3-b]pyridin-3-yl]phenyl}methanol, formate salt |
| 29 | 72.5 | 54.4 | {4-fluoro-3-[4-(morpholin-4-yl)-1H-pyrrolo[2,3-b]pyridin-3-yl]phenyl}methanol, formate salt |
| 30 | 179[a] | 353[a] | 3-[3-(5-methyl-1,3,4-oxadiazol-2-yl)phenyl]-4-(morpholin-4-yl)-1H-pyrrolo[2,3-b]pyridine, formate salt |
| 31 | 124[a] | 95.5[a] | 3-(3-methoxyphenyl)-4-(morpholin-4-yl)-1H-pyrrolo[2,3-b]pyridine, formate salt |
| 32 | 40.7 | 69.2 | 3-(3-chloro-2-fluorophenyl)-4-(morpholin-4-yl)-1H-pyrrolo[2,3-b]pyridine, formate salt |
| 33 | 69.7[a] | 88.4[a] | 4-(morpholin-4-yl)-3-(2,3,5-trifluorophenyl)-1H-pyrrolo[2,3-b]pyridine, formate salt |
| 34 | 43.3[a] | 50.9[a] | 3-(3,5-difluorophenyl)-4-(morpholin-4-yl)-1H-pyrrolo[2,3-b]pyridine, formate salt |
| 35 | 110[a] | 279[a] | 3-(2-chloropyridin-3-yl)-4-(morpholin-4-yl)-1H-pyrrolo[2,3-b]pyridine, formate salt |
| 36 | 49.7 | 27.5 | 4-(morpholin-4-yl)-3-phenyl-1H-pyrrolo[2,3-b]pyridine, formate salt |
| 37 | 147[a] | 116[a] | 3-(2,4-difluorophenyl)-4-(morpholin-4-yl)-1H-pyrrolo[2,3-b]pyridine, formate salt |
| 38 | 22.9 | 11.6 | 3-(3-fluoro-5-methylphenyl)-4-(morpholin-4-yl)-1H-pyrrolo[2,3-b]pyridine, formate salt |
| 39 | 140[a] | 461[a] | 3-fluoro-5-[4-(morpholin-4-yl)-1H-pyrrolo[2,3-b]pyridin-3-yl]benzonitrile, formate salt |
| 40 | 105 | 129 | 3-(2,3-difluoro-6-methoxyphenyl)-4-(morpholin-4-yl)-1H-pyrrolo[2,3-b]pyridine, formate salt |
| 41 | 226 | 998 | 2-fluoro-5-[4-(morpholin-4-yl)-1H-pyrrolo[2,3-b]pyridin-3-yl]benzonitrile, formate salt |
| 42 | 240 | 295 | 3-(5-methoxypyridin-3-yl)-4-(morpholin-4-yl)-1H-pyrrolo[2,3-b]pyridine, formate salt |
| 43 | 31.9 | 104 | 6-[2-methyl-4-(morpholin-4-yl)-1H-pyrrolo[2,3-b]pyridin-3-yl]pyridine-2-carbonitrile |
| 44 | 143 | 348 | 3-(1-methyl-1H-pyrazol-4-yl)-4-(morpholin-4-yl)-1H-pyrrolo[2,3-b]pyridine-5-carbonitrile |
| 45 | 20.4 | 88.4 | 3-(3-cyano-2-fluorophenyl)-4-(morpholin-4-yl)-1H-pyrrolo[2,3-b]pyridine-5-carbonitrile |
| 46 | 29.6 | 36.7 | 3-(3-fluoro-5-methylphenyl)-4-(morpholin-4-yl)-1H-pyrrolo[2,3-b]pyridine-5-carbonitrile |
| 47 | 144 | 505 | 4-fluoro-3-[4-(morpholin-4-yl)-1H-pyrrolo[2,3-b]pyridin-3-yl]benzonitrile |
| 48 | 217 | 424 | 3-fluoro-4-[4-(morpholin-4-yl)-1H-pyrrolo[2,3-b]pyridin-3-yl]benzonitrile |
| 49 | 50.8 | 99.0 | 3-(hydroxymethyl)-5-[4-(morpholin-4-yl)-1H-pyrrolo[2,3-b]pyridin-3-yl]benzonitrile |
| 50 | 191 | 155 | 3-(4-fluorophenyl)-4-(morpholin-4-yl)-1H-pyrrolo[2,3-b]pyridine, formate salt |
| 51 | 191 | 295 | 2-methyl-3-(5-methylpyridin-3-yl)-4-(morpholin-4-yl)-1H-pyrrolo[2,3-b]pyridine |
| 52 | 158 | 153 | 3-(3-chlorophenyl)-2-methyl-4-(morpholin-4-yl)-1H-pyrrolo[2,3-b]pyridine |
| 53 | 201 | 154 | 2-methyl-4-(morpholin-4-yl)-3-phenyl-1H-pyrrolo[2,3-b]pyridine |
| 54 | 91.6 | 61.4 | 3-(2-fluorophenyl)-2-methyl-4-(morpholin-4-yl)-1H-pyrrolo[2,3-b]pyridine |

TABLE 2-continued

Biology data and IUPAC names for Examples 1-112.

| Example Number | LRRK2 LANTHA $EC_{50}$ at 1 mM ATP; Geometric mean of 2-3 determinations unless otherwise indicated | Mutant LRRK2 LANTHA $EC_{50}$ at 1 mM ATP; Geometric mean of 2-3 determinations unless otherwise indicated | IUPAC Name |
|---|---|---|---|
| 55 | 101 | 80.4 | 3-(3-fluorophenyl)-2-methyl-4-(morpholin-4-yl)-1H-pyrrolo[2,3-b]pyridine |
| 56 | 174 | 639 | 3-fluoro-5-[2-methyl-4-(morpholin-4-yl)-1H-pyrrolo[2,3-b]pyridin-3-yl]benzonitrile |
| 57 | 91.9 | 93.2 | 1-[3-(1-methyl-1H-pyrazol-4-yl)-1H-pyrrolo[2,3-b]pyridin-4-yl]piperidin-3-ol, formate salt |
| 58 | 169 | 235 | 4-[(2S)-2-methylmorpholin-4-yl]-3-(1-methyl-1H-pyrazol-4-yl)-1H-pyrrolo[2,3-b] pyridine, formate salt |
| 59 | 197 | 196 | 4-(3,3-difluoropiperidin-1-yl)-3-(1-methyl-1H-pyrazol-4-yl)-1H-pyrrolo[2,3-b]pyridine, formate salt |
| 60 | 140 | 138 | {1-[3-(1-methyl-1H-pyrazol-4-yl)-1H-pyrrolo[2,3-b]pyridin-4-yl]piperidin-3-yl} methanol |
| 61 | 221 | 435 | 3-(1-methyl-1H-pyrazol-4-yl)-4-(8-oxa-3-azabicyclo[3.2.1]oct-3-yl)-1H-pyrrolo[2,3-b]pyridine, formate salt |
| 62 | 185 | 147 | N,N-dimethyl-3-(1-methyl-1H-pyrazol-4-yl)-1H-pyrrolo[2,3-b]pyridin-4-amine |
| 63 | 71.9 | 84.0 | 3-(1-methyl-1H-pyrazol-4-yl)-4-(thiomorpholin-4-yl)-1H-pyrrolo[2,3-b]pyridine |
| 64 | 195 | 206 | 4-(3,3-difluoropyrrolidin-1-yl)-3-(1-methyl-1H-pyrazol-4-yl)-1H-pyrrolo[2,3-b]pyridine, formate salt |
| 65 | 7.17 | 36.9 | 3-[4-(3,6-dihydro-2H-pyran-4-yl)-1H-pyrrolo[2,3-b]pyridin-3-yl]benzonitrile, formate salt |
| 66 | 24.3[b] | 71.3[b] | 3-[4-(3-hydroxypiperidin-1-yl)-1H-pyrrolo[2,3-b]pyridin-3-yl]benzonitrile |
| 67 | 22.0 | 104 | 3-{4-[2-(methoxymethyl)morpholin-4-yl]-1H-pyrrolo[2,3-b]pyridin-3-yl}benzonitrile, formate salt |
| 68 | 30.5[b] | 46.1[b] | 4-(morpholin-4-yl)-3-(1H-pyrazol-4-yl)-1H-pyrrolo[2,3-b]pyridine |
| 69 | 150 | 616 | 3-[4-(1,4-oxazepan-4-yl)-1H-pyrrolo[2,3-b]pyridin-3-yl]benzonitrile |
| 70 | 85.3 | 269 | 3-[4-(4-hydroxypiperidin-1-yl)-1H-pyrrolo[2,3-b]pyridin-3-yl]benzonitrile |
| 71 | 95.8 | 222 | 3-[4-(3-methoxypiperidin-1-yl)-1H-pyrrolo[2,3-b]pyridin-3-yl]benzonitrile |
| 72 | 68.3 | 356 | 3-[4-(6-oxa-3-azabicyclo[3.1.1]hept-3-yl)-1H-pyrrolo[2,3-b]pyridin-3-yl]benzonitrile |
| 73 | 44.4 | 212 | 3-{4-[(3R,4R)-3,4-difluoropyrrolidin-1-yl]-1H-pyrrolo[2,3-b]pyridin-3-yl}benzonitrile, formate salt |
| 74 | 39.0 | 168 | 3-[4-(4-fluoropiperidin-1-yl)-1H-pyrrolo[2,3-b]pyridin-3-yl]benzonitrile, formate salt |
| 75 | 38.7 | 209 | 3-{4-[(3R)-3-fluoropyrrolidin-1-yl]-1H-pyrrolo[2,3-b]pyridin-3-yl}benzonitrile, formate salt |
| 76 | 30.6 | 95.2 | 3-{4-[(2R)-2-methylmorpholin-4-yl]-1H-pyrrolo[2,3-b]pyridin-3-yl}benzonitrile, formate salt |
| 77 | 14.1 | 76.0 | 3-[4-(pyrrolidin-1-yl)-1H-pyrrolo[2,3-b]pyridin-3-yl]benzonitrile, formate salt |
| 78 | 24.0 | 142 | 3-{4-[(3S)-3-fluoropyrrolidin-1-yl]-1H-pyrrolo[2,3-b]pyridin-3-yl}benzonitrile, formate salt |
| 79 | 99.2 | 429 | 3-[4-(3,3-difluoropiperidin-1-yl)-1H-pyrrolo[2,3-b]pyridin-3-yl]benzonitrile, formate salt |
| 80 | 10.5 | 50.9 | 3-{4-[(2S)-2-methylmorpholin-4-yl]-1H-pyrrolo[2,3-b]pyridin-3-yl}benzonitrile, formate salt |

TABLE 2-continued

Biology data and IUPAC names for Examples 1-112.

| Example Number | LRRK2 LANTHA $EC_{50}$ at 1 mM ATP; Geometric mean of 2-3 determinations unless otherwise indicated | Mutant LRRK2 LANTHA $EC_{50}$ at 1 mM ATP; Geometric mean of 2-3 determinations unless otherwise indicated | IUPAC Name |
|---|---|---|---|
| 81 | 11.1 | 12.5 | 4-[4-(morpholin-4-yl)-1H-pyrrolo[2,3-b]pyridin-3-yl]pyridin-2(1H)-one |
| 82 | 12.3 | 74.7 | methyl 3-(3-cyanophenyl)-4-(morpholin-4-yl)-1H-pyrrolo[2,3-b]pyridine-5-carboxylate |
| 83 | 106 | 391 | 3-[5-(cyanomethyl)-4-(morpholin-4-yl)-1H-pyrrolo[2,3-b]pyridin-3-yl]benzonitrile |
| 84 | 63.4 | 241 | 3-[5-(methoxymethyl)-4-(morpholin-4-yl)-1H-pyrrolo[2,3-b]pyridin-3-yl]benzonitrile |
| 85 | 21.7 | 26.6 | 1-methyl-4-[4-(morpholin-4-yl)-1H-pyrrolo[2,3-b]pyridin-3-yl]-1H-pyrrole-2-carboxamide |
| 86 | 2.75 | 5.24 | 4-[4-(morpholin-4-yl)-1H-pyrrolo[2,3-b]pyridin-3-yl]-1H-pyrrole-2-carbonitrile, formate salt |
| 87 | 5.46 | 14.4 | 1-methyl-4-[2-methyl-4-(morpholin-4-yl)-1H-pyrrolo[2,3-b]pyridin-3-yl]-1H-pyrrole-2-carbonitrile |
| 88 | 9.93 | 77.1 | 3-[4-(pyridin-4-yl)-1H-pyrrolo[2,3-b]pyridin-3-yl]benzonitrile, formate salt |
| 89 | 13.7 | 18.7 | 3-(1-methyl-1H-pyrazol-4-yl)-4-phenyl-1H-pyrrolo[2,3-b]pyridine, formate salt |
| 90 | 42.2[a] | 212[a] | 3-[4-(morpholin-4-yl)-7H-pyrrolo[2,3-c]pyridazin-5-yl]benzonitrile |
| 91 | 43.4 | 246 | 3-[3-(3-cyanophenyl)-1H-pyrrolo[2,3-b]pyridin-4-yl]-N-cyclopropylbenzamide |
| 92 | 43.7 | 316 | 2-fluoro-3-[4-(morpholin-4-yl)-7H-pyrrolo[2,3-c]pyridazin-5-yl]benzonitrile |
| 93 | 45.6 | 257 | 3-[4-(pyridin-3-yl)-1H-pyrrolo[2,3-b]pyridin-3-yl]benzonitrile, formate salt |
| 94 | 45.6 | 59.4 | 4-(3,4-difluorophenyl)-3-(1-methyl-1H-pyrazol-4-yl)-1H-pyrrolo[2,3-b]pyridine, formate salt |
| 95 | 49.5 | 51.4 | 4-(2,5-difluorophenyl)-3-(1-methyl-1H-pyrazol-4-yl)-1H-pyrrolo[2,3-b]pyridine, formate salt |
| 96 | 58.9 | 67.1 | 4-(2,3-difluorophenyl)-3-(1-methyl-1H-pyrazol-4-yl)-1H-pyrrolo[2,3-b]pyridine, formate salt |
| 97 | 63.1 | 46.7 | 4-(3-chlorophenyl)-3-(1-methyl-1H-pyrazol-4-yl)-1H-pyrrolo[2,3-b]pyridine, formate salt |
| 98 | 85.9 | 78.9 | 4-(2-fluoro-3-methoxyphenyl)-3-(1-methyl-1H-pyrazol-4-yl)-1H-pyrrolo[2,3-b]pyridine, formate salt |
| 99 | 92.5 | 401 | 3-[3-(3-cyanophenyl)-1H-pyrrolo[2,3-b]pyridin-4-yl]-N-methylbenzenesulfonamide |
| 100 | 99.2 | 38.0 | 4-cyclopropyl-3-(2,3-difluoro-6-methoxyphenyl)-1H-pyrrolo[2,3-b]pyridine-5-carbonitrile |
| 101 | 101 | 99.7 | 3-[4-(1-methyl-1H-pyrazol-4-yl)-1H-pyrrolo[2,3-b]pyridin-3-yl]benzonitrile, formate salt |
| 102 | 102 | 221 | 3-(1-methyl-1H-pyrazol-4-yl)-4-(pyridin-4-yl)-1H-pyrrolo[2,3-b]pyridine |
| 103 | 125 | 109 | 4-(3,5-difluorophenyl)-3-(1-methyl-1H-pyrazol-4-yl)-1H-pyrrolo[2,3-b]pyridine, formate salt |
| 104 | 138 | 70.4 | 4-(3-fluoro-4-methoxyphenyl)-3-(1-methyl-1H-pyrazol-4-yl)-1H-pyrrolo[2,3-b]pyridine, formate salt |
| 105 | 143 | 117 | 4-(2-fluoro-4-methoxyphenyl)-3-(1-methyl-1H-pyrazol-4-yl)-1H-pyrrolo[2,3-b]pyridine, formate salt |
| 106 | 144 | 230 | 4-(furan-3-yl)-3-(1-methyl-1H-pyrazol-4-yl)-1H-pyrrolo[2,3-b]pyridine, formate salt |

TABLE 2-continued

Biology data and IUPAC names for Examples 1-112.

| Example Number | LRRK2 LANTHA $EC_{50}$ at 1 mM ATP; Geometric mean of 2-3 determinations unless otherwise indicated | Mutant LRRK2 LANTHA $EC_{50}$ at 1 mM ATP; Geometric mean of 2-3 determinations unless otherwise indicated | IUPAC Name |
|---|---|---|---|
| 107 | 169 | 263 | 5-[3-(1-methyl-1H-pyrazol-4-yl)-1H-pyrrolo[2,3-b]pyridin-4-yl]-1,3-benzothiazole |
| 108 | 185 | 313 | {3-[3-(1-methyl-1H-pyrazol-4-yl)-1H-pyrrolo[2,3-b]pyridin-4-yl]phenyl}acetonitrile, formate salt |
| 109 | 188 | 105 | 3-[3-(1-methyl-1H-pyrazol-4-yl)-1H-pyrrolo[2,3-b]pyridin-4-yl]benzonitrile, formate salt |
| 110 | 201[b] | 457[b] | 5-(1-methyl-1H-pyrazol-4-yl)-4-(morpholin-4-yl)-7H-pyrrolo[2,3-c]pyridazine, formate salt |
| 111 | 234 | 354 | 4-[3-(methoxymethyl)phenyl]-3-(1-methyl-1H-pyrazol-4-yl)-1H-pyrrolo[2,3-b]pyridine, formate salt |
| 112 | 234 | 1390 | 3-{4-[3-(5-methyl-1,3,4-oxadiazol-2-yl)phenyl]-1H-pyrrolo[2,3-b]pyridin-3-yl}benzonitrile, formate salt |

[a]$EC_{50}$ value represents the geometric mean of ≥4 determinations.
[b]$EC_{50}$ value derived from a single determination.

We claim:

1. A compound selected from the group consisting of:

3-[4-(morpholin-4-yl)-1H-pyrrolo[2,3-b]pyridin-3-yl]benzonitrile;

2-fluoro-3-[4-(morpholin-4-yl)-1H-pyrrolo[2,3-b]pyridin-3-yl]benzonitrile;

3-[4-(morpholin-4-yl)-1H-pyrrolo[2,3-b]pyridin-3-yl]imidazo[1,2-b]pyridazine;

1-methyl-4-[4-(morpholin-4-yl)-1H-pyrrolo[2,3-b]pyridin-3-yl]-1H-pyrrole-2-carbonitrile;

1-methyl-4-[4-(morpholin-4-yl)-1H-pyrrolo[2,3-b]pyridin-3-yl]-1H-imidazole-2-carbonitrile;

1-methyl-4-[4-(morpholin-4-yl)-7H-pyrrolo[2,3-c]pyridazin-5-yl]-1H-pyrrole-2-carbonitrile;

4-[2-chloro-4-(morpholin-4-yl)-1H-pyrrolo[2,3-b]pyridin-3-yl]-1-methyl-1H-pyrrole-2-carbonitrile;

3-[2-methyl-4-(morpholin-4-yl)-1H-pyrrolo[2,3-b]pyridin-3-yl]benzonitrile;

3-[6-methyl-4-(morpholin-4-yl)-1H-pyrrolo[2,3-b]pyridin-3-yl]benzonitrile;

3-[5-(hydroxymethyl)-4-(morpholin-4-yl)-1H-pyrrolo[2,3-b]pyridin-3-yl]benzonitrile;

3-(3-cyanophenyl)-4-(morpholin-4-yl)-1H-pyrrolo[2,3-b]pyridine-5-carbonitrile;

4-(3,6-dihydro-2H-pyran-4-yl)-3-(1-methyl-1H-pyrazol-4-yl)-1H-pyrrolo[2,3-b]pyridine;

3-(1-methyl-1H-pyrazol-4-yl)-4-(morpholin-4-yl)-1H-pyrrolo[2,3-b]pyridine;

3-(3-cyano-2-fluorophenyl)-4-(dimethylamino)-1H-pyrrolo[2,3-b]pyridine-5-carbonitrile;

3-(5-fluoro-2-methoxyphenyl)-4-(morpholin-4-yl)-1H-pyrrolo[2,3-b]pyridine;

3-(3-fluoro-5-methoxyphenyl)-4-(morpholin-4-yl)-1H-pyrrolo[2,3-b]pyridine;

2-methyl-3-(1-methyl-1H-pyrazol-4-yl)-4-(morpholin-4-yl)-1H-pyrrolo[2,3-b]pyridine;

2-fluoro-3-[6-methyl-4-(morpholin-4-yl)-1H-pyrrolo[2,3-b]pyridin-3-yl]benzonitrile;

6-[4-(morpholin-4-yl)-1H-pyrrolo[2,3-b]pyridin-3-yl]pyridine-2-carbonitrile;

3-(3-chlorophenyl)-4-(morpholin-4-yl)-1H-pyrrolo[2,3-b]pyridine;

3-(3-chloro-5-fluorophenyl)-4-(morpholin-4-yl)-1H-pyrrolo[2,3-b]pyridine;

3-(2,5-difluorophenyl)-4-(morpholin-4-yl)-1H-pyrrolo[2,3-b]pyridine;

3-(2-chlorophenyl)-4-(morpholin-4-yl)-1H-pyrrolo[2,3-b]pyridine;

3-(2,3-difluorophenyl)-4-(morpholin-4-yl)-1H-pyrrolo[2,3-b]pyridine;

3-(3-fluorophenyl)-4-(morpholin-4-yl)-1H-pyrrolo[2,3-b]pyridine;

3-(2-fluorophenyl)-4-(morpholin-4-yl)-1H-pyrrolo[2,3-b]pyridine;

3-(5-chloro-2-fluorophenyl)-4-(morpholin-4-yl)-1H-pyrrolo[2,3-b]pyridine;

{3-[4-(morpholin-4-yl)-1H-pyrrolo[2,3-b]pyridin-3-yl]phenyl}methanol;

{4-fluoro-3-[4-(morpholin-4-yl)-1H-pyrrolo[2,3-b]pyridin-3-yl]phenyl}methanol;

3-[3-(5-methyl-1,3,4-oxadiazol-2-yl)phenyl]-4-(morpholin-4-yl)-1H-pyrrolo[2,3-b]pyridine;

3-(3-methoxyphenyl)-4-(morpholin-4-yl)-1H-pyrrolo[2,3-b]pyridine;

3-(3-chloro-2-fluorophenyl)-4-(morpholin-4-yl)-1H-pyrrolo[2,3-b]pyridine;

4-(morpholin-4-yl)-3-(2,3,5-trifluorophenyl)-1H-pyrrolo[2,3-b]pyridine;

3-(3,5-difluorophenyl)-4-(morpholin-4-yl)-1H-pyrrolo[2,3-b]pyridine;

3-(2-chloropyridin-3-yl)-4-(morpholin-4-yl)-1H-pyrrolo[2,3-b]pyridine;

4-(morpholin-4-yl)-3-phenyl-1H-pyrrolo[2,3-b]pyridine;

3-(2,4-difluorophenyl)-4-(morpholin-4-yl)-1H-pyrrolo[2,3-b]pyridine;

3-(3-fluoro-5-methylphenyl)-4-(morpholin-4-yl)-1H-pyrrolo[2,3-b]pyridine;

3-fluoro-5-[4-(morpholin-4-yl)-1H-pyrrolo[2,3-b]pyridin-3-yl]benzonitrile;

3-(2,3-difluoro-6-methoxyphenyl)-4-(morpholin-4-yl)-1H-pyrrolo[2,3-b]pyridine;

2-fluoro-5-[4-(morpholin-4-yl)-1H-pyrrolo[2,3-b]pyridin-3-yl]benzonitrile;

3-(5-methoxypyridin-3-yl)-4-(morpholin-4-yl)-1H-pyrrolo[2,3-b]pyridine;

6-[2-methyl-4-(morpholin-4-yl)-1H-pyrrolo[2,3-b]pyridin-3-yl]pyridine-2-carbonitrile;

3-(1-methyl-1H-pyrazol-4-yl)-4-(morpholin-4-yl)-1H-pyrrolo[2,3-b]pyridine-5-carbonitrile;

3-(3-cyano-2-fluorophenyl)-4-(morpholin-4-yl)-1H-pyrrolo[2,3-b]pyridine-5-carbonitrile;

3-(3-fluoro-5-methylphenyl)-4-(morpholin-4-yl)-1H-pyrrolo[2,3-b]pyridine-5-carbonitrile;

4-fluoro-3-[4-(morpholin-4-yl)-1H-pyrrolo[2,3-b]pyridin-3-yl]benzonitrile;

3-fluoro-4-[4-(morpholin-4-yl)-1H-pyrrolo[2,3-b]pyridin-3-yl]benzonitrile;

3-(hydroxymethyl)-5-[4-(morpholin-4-yl)-1H-pyrrolo[2,3-b]pyridin-3-yl]benzonitrile;

3-(4-fluorophenyl)-4-(morpholin-4-yl)-1H-pyrrolo[2,3-b]pyridine;

2-methyl-3-(5-methylpyridin-3-yl)-4-(morpholin-4-yl)-1H-pyrrolo[2,3-b]pyridine;

3-(3-chlorophenyl)-2-methyl-4-(morpholin-4-yl)-1H-pyrrolo[2,3-b]pyridine;

2-methyl-4-(morpholin-4-yl)-3-phenyl-1H-pyrrolo[2,3-b]pyridine;

3-(2-fluorophenyl)-2-methyl-4-(morpholin-4-yl)-1H-pyrrolo[2,3-b]pyridine;

3-(3-fluorophenyl)-2-methyl-4-(morpholin-4-yl)-1H-pyrrolo[2,3-b]pyridine;

3-fluoro-5-[2-methyl-4-(morpholin-4-yl)-1H-pyrrolo[2,3-b]pyridin-3-yl]benzonitrile;

1-[3-(1-methyl-1H-pyrazol-4-yl)-1H-pyrrolo[2,3-b]pyridin-4-yl]piperidin-3-ol;

4-[(2S)-2-methylmorpholin-4-yl]-3-(1-methyl-1H-pyrazol-4-yl)-1H-pyrrolo[2,3-b]pyridine;

4-(3,3-difluoropiperidin-1-yl)-3-(1-methyl-1H-pyrazol-4-yl)-1H-pyrrolo[2,3-b]pyridine;

{1-[3-(1-methyl-1H-pyrazol-4-yl)-1H-pyrrolo[2,3-b]pyridin-4-yl]piperidin-3-yl}methanol;

3-(1-methyl-1H-pyrazol-4-yl)-4-(8-oxa-3-azabicyclo[3.2.1]oct-3-yl)-1H-pyrrolo[2,3-b]pyridine;

N,N-dimethyl-3-(1-methyl-1H-pyrazol-4-yl)-1H-pyrrolo[2,3-b]pyridin-4-amine;

3-(1-methyl-1H-pyrazol-4-yl)-4-(thiomorpholin-4-yl)-1H-pyrrolo[2,3-b]pyridine;

4-(3,3-difluoropyrrolidin-1-yl)-3-(1-methyl-1H-pyrazol-4-yl)-1H-pyrrolo[2,3-b]pyridine;

3-[4-(3,6-dihydro-2H-pyran-4-yl)-1H-pyrrolo[2,3-b]pyridin-3-yl]benzonitrile;

3-[4-(3-hydroxypiperidin-1-yl)-1H-pyrrolo[2,3-b]pyridin-3-yl]benzonitrile;

3-{4-[2-(methoxymethyl)morpholin-4-yl]-1H-pyrrolo[2,3-b]pyridin-3-yl}benzonitrile;

4-(morpholin-4-yl)-3-(1H-pyrazol-4-yl)-1H-pyrrolo[2,3-b]pyridine;

3-[4-(1,4-oxazepan-4-yl)-1H-pyrrolo[2,3-b]pyridin-3-yl]benzonitrile;

3-[4-(4-hydroxypiperidin-1-yl)-1H-pyrrolo[2,3-b]pyridin-3-yl]benzonitrile;

3-[4-(3-methoxypiperidin-1-yl)-1H-pyrrolo[2,3-b]pyridin-3-yl]benzonitrile;

3-[4-(6-oxa-3-azabicyclo[3.1.1]hept-3-yl)-1H-pyrrolo[2,3-b]pyridin-3-yl]benzonitrile;

3-{4-[(3R,4R)-3,4-difluoropyrrolidin-1-yl]-1H-pyrrolo[2,3-b]pyridin-3-yl}benzonitrile;

3-[4-(4-fluoropiperidin-1-yl)-1H-pyrrolo[2,3-b]pyridin-3-yl]benzonitrile;

3-{4-[(3R)-3-fluoropyrrolidin-1-yl]-1H-pyrrolo[2,3-b]pyridin-3-yl}benzonitrile;

3-{4-[(2R)-2-methylmorpholin-4-yl]-1H-pyrrolo[2,3-b]pyridin-3-yl}benzonitrile;

3-[4-(pyrrolidin-1-yl)-1H-pyrrolo[2,3-b]pyridin-3-yl]benzonitrile;

3-{4-[(3S)-3-fluoropyrrolidin-1-yl]-1H-pyrrolo[2,3-b]pyridin-3-yl}benzonitrile;

3-[4-(3,3-difluoropiperidin-1-yl)-1H-pyrrolo[2,3-b]pyridin-3-yl]benzonitrile;

3-{4-[(2S)-2-methylmorpholin-4-yl]-1H-pyrrolo[2,3-b]pyridin-3-yl}benzonitrile;

4-[4-(morpholin-4-yl)-1H-pyrrolo[2,3-b]pyridin-3-yl]pyridin-2(1H)-one;

methyl 3-(3-cyanophenyl)-4-(morpholin-4-yl)-1H-pyrrolo[2,3-b]pyridine-5-carboxylate;

3-[5-(cyanomethyl)-4-(morpholin-4-yl)-1H-pyrrolo[2,3-b]pyridin-3-yl]benzonitrile;

3-[5-(methoxymethyl)-4-(morpholin-4-yl)-1H-pyrrolo[2,3-b]pyridin-3-yl]benzonitrile;

1-methyl-4-[4-(morpholin-4-yl)-1H-pyrrolo[2,3-b]pyridin-3-yl]-1H-pyrrole-2-carboxamide;

4-[4-(morpholin-4-yl)-1H-pyrrolo[2,3-b]pyridin-3-yl]-1H-pyrrole-2-carbonitrile;

1-methyl-4-[2-methyl-4-(morpholin-4-yl)-1H-pyrrolo[2,3-b]pyridin-3-yl]-1H-pyrrole-2-carbonitrile;

3-[4-(pyridin-4-yl)-1H-pyrrolo[2,3-b]pyridin-3-yl]benzonitrile;

3-(1-methyl-1H-pyrazol-4-yl)-4-phenyl-1H-pyrrolo[2,3-b]pyridine;

3-[4-(morpholin-4-yl)-7H-pyrrolo[2,3-c]pyridazin-5-yl]benzonitrile;

3-[3-(3-cyanophenyl)-1H-pyrrolo[2,3-b]pyridin-4-yl]-N-cyclopropylbenzamide;

2-fluoro-3-[4-(morpholin-4-yl)-7H-pyrrolo[2,3-c]pyridazin-5-yl]benzonitrile;

3-[4-(pyridin-3-yl)-1H-pyrrolo[2,3-b]pyridin-3-yl]benzonitrile;

4-(3,4-difluorophenyl)-3-(1-methyl-1H-pyrazol-4-yl)-1H-pyrrolo[2,3-b]pyridine;

4-(2,5-difluorophenyl)-3-(1-methyl-1H-pyrazol-4-yl)-1H-pyrrolo[2,3-b]pyridine;

4-(2,3-difluorophenyl)-3-(1-methyl-1H-pyrazol-4-yl)-1H-pyrrolo[2,3-b]pyridine;

4-(3-chlorophenyl)-3-(1-methyl-1H-pyrazol-4-yl)-1H-pyrrolo[2,3-b]pyridine;

4-(2-fluoro-3-methoxyphenyl)-3-(1-methyl-1H-pyrazol-4-yl)-1H-pyrrolo[2,3-b]pyridine;

3-[3-(3-cyanophenyl)-1H-pyrrolo[2,3-b]pyridin-4-yl]-N-methylbenzenesulfonamide;

4-cyclopropyl-3-(2,3-difluoro-6-methoxyphenyl)-1H-pyrrolo[2,3-b]pyridine-5-carbonitrile;

3-[4-(1-methyl-1H-pyrazol-4-yl)-1H-pyrrolo[2,3-b]pyridin-3-yl]benzonitrile;

3-(1-methyl-1H-pyrazol-4-yl)-4-(pyridin-4-yl)-1H-pyrrolo[2,3-b]pyridine;

4-(3,5-difluorophenyl)-3-(1-methyl-1H-pyrazol-4-yl)-1H-pyrrolo[2,3-b]pyridine;

4-(3-fluoro-4-methoxyphenyl)-3-(1-methyl-1H-pyrazol-4-yl)-1H-pyrrolo[2,3-b]pyridine;
4-(2-fluoro-4-methoxyphenyl)-3-(1-methyl-1H-pyrazol-4-yl)-1H-pyrrolo[2,3-b]pyridine;
4-(furan-3-yl)-3-(1-methyl-1H-pyrazol-4-yl)-1H-pyrrolo[2,3-b]pyridine;
5-[3-(1-methyl-1H-pyrazol-4-yl)-1H-pyrrolo[2,3-b]pyridin-4-yl]-1,3-benzothiazole;
{3-[3-(1-methyl-1H-pyrazol-4-yl)-1H-pyrrolo[2,3-b]pyridin-4-yl]phenyl}acetonitrile;
3-[3-(1-methyl-1H-pyrazol-4-yl)-1H-pyrrolo[2,3-b]pyridin-4-yl]benzonitrile;
5-(1-methyl-1H-pyrazol-4-yl)-4-(morpholin-4-yl)-7H-pyrrolo[2,3-c]pyridazine;
4-[3-(m ethoxymethyl)phenyl]-3-(1-methyl-1H-pyrazol-4-yl)-1H-pyrrolo[2,3-b]pyridine; and
3-{4-[3-(5-methyl-1,3,4-oxadiazol-2-yl)phenyl]-1H-pyrrolo[2,3-b]pyridin-3-yl}benzonitrile;
or a pharmaceutically acceptable salt thereof.

2. A compound selected from the group consisting of:
3-[4-(morpholin-4-yl)-1H-pyrrolo[2,3-b]pyridin-3-yl]benzonitrile;
2-fluoro-3-[4-(morpholin-4-yl)-1H-pyrrolo[2,3-b]pyridin-3-yl]benzonitrile;
3-[4-(morpholin-4-yl)-1H-pyrrolo[2,3-b]pyridin-3-yl]imidazo[1,2-b]pyridazine;
1-methyl-4-[4-(morpholin-4-yl)-1H-pyrrolo[2,3-b]pyridin-3-yl]-1H-pyrrole-2-carbonitrile;
1-methyl-4-[4-(morpholin-4-yl)-1H-pyrrolo[2,3-b]pyridin-3-yl]-1H-imidazole-2-carbonitrile;
1-methyl-4-[4-(morpholin-4-yl)-7H-pyrrolo[2,3-c]pyridazin-5-yl]-1H-pyrrole-2-carbonitrile;
4-[2-chloro-4-(morpholin-4-yl)-1H-pyrrolo[2,3-b]pyridin-3-yl]-1-methyl-1H-pyrrole-2-carbonitrile;
3-(3-cyanophenyl)-4-(morpholin-4-yl)-1H-pyrrolo[2,3-b]pyridine-5-carbonitrile;
3-(1-methyl-1H-pyrazol-4-yl)-4-(morpholin-4-yl)-1H-pyrrolo[2,3-b]pyridine;
3-(3-cyano-2-fluorophenyl)-4-(dimethylamino)-1H-pyrrolo[2,3-b]pyridine-5-carbonitrile;
3-(2,3-difluorophenyl)-4-(morpholin-4-yl)-1H-pyrrolo[2,3-b]pyridine;
3-(2-fluorophenyl)-4-(morpholin-4-yl)-1H-pyrrolo[2,3-b]pyridine;
3-(3-fluoro-5-methylphenyl)-4-(morpholin-4-yl)-1H-pyrrolo[2,3-b]pyridine;
3-(3-cyano-2-fluorophenyl)-4-(morpholin-4-yl)-1H-pyrrolo[2,3-b]pyridine-5-carbonitrile;
3-(3-fluoro-5-methylphenyl)-4-(morpholin-4-yl)-1H-pyrrolo[2,3-b]pyridine-5-carbonitrile;
3-[4-(3,6-dihydro-2H-pyran-4-yl)-1H-pyrrolo[2,3-b]pyridin-3-yl]benzonitrile;
3-[4-(3-hydroxypiperidin-1-yl)-1H-pyrrolo[2, 3-b]pyridin-3-yl]benzonitrile;
3-[4-(pyrrolidin-1-yl)-1H-pyrrolo[2, 3-b]pyridin-3-yl]benzonitrile;
3-{4-[(3S)-3-fluoropyrrolidin-1-yl]-1H-pyrrolo[2,3-b]pyridin-3-yl}benzonitrile;
3-{4-[(2S)-2-methylmorpholin-4-yl]-1H-pyrrolo[2,3-b]pyridin-3-yl}benzonitrile;
4-[4-(morpholin-4-yl)-1H-pyrrolo[2,3-b]pyridin-3-yl]pyridin-2(1H)-one;
methyl 3-(3-cyanophenyl)-4-(morpholin-4-yl)-1H-pyrrolo[2,3-b]pyridine-5-carboxylate;
1-methyl-4-[4-(morpholin-4-yl)-1H-pyrrolo[2,3-b]pyridin-3-yl]-1H-pyrrole-2-carboxamide;
4-[4-(morpholin-4-yl)-1H-pyrrolo[2,3-b]pyridin-3-yl]-1H-pyrrole-2-carbonitrile;
1-methyl-4-[2-methyl-4-(morpholin-4-yl)-1H-pyrrolo[2,3-b]pyridin-3-yl]-1H-pyrrole-2-carbonitrile;
3-[4-(pyridin-4-yl)-1H-pyrrolo[2,3-b]pyridin-3-yl]benzonitrile; and
3-(1-methyl-1H-pyrazol-4-yl)-4-phenyl-1H-pyrrolo[2,3-b]pyridine;
or a pharmaceutically acceptable salt thereof.

3. A compound selected from the group consisting of
3-[4-(morpholin-4-yl)-1H-pyrrolo[2,3-b]pyridin-3-yl]benzonitrile;
1-methyl-4-[4-(morpholin-4-yl)-1H-pyrrolo[2,3-b]pyridin-3-yl]-1H-pyrrole-2-carbonitrile; and 3-(1-methyl-1H-pyrazol-4-yl)-4-(morpholin-4-yl)-1H-pyrrolo[2,3-b]pyridine;
or a pharmaceutically acceptable salt thereof.

4. The compound of claim 3 which is 3-[4-(morpholin-4-yl)-1H-pyrrolo[2,3-b]pyridin-3-yl]benzonitrile, or a pharmaceutically acceptable salt thereof.

5. The compound of claim 3 which is 1-methyl-4-[4-(morpholin-4-yl)-1H-pyrrolo[2,3-b]pyridin-3-yl]-1H-pyrrole-2-carbonitrile, or a pharmaceutically acceptable salt thereof.

6. The compound of claim 3 which is 3-(1-methyl-1H-pyrazol-4-yl)-4-(morpholin-4-yl)-1H-pyrrolo[2,3-b]pyridine, or a pharmaceutically acceptable salt thereof.

7. A pharmaceutical composition comprising a therapeutically effective amount of a compound according to claim 1, or a pharmaceutically acceptable salt thereof together with a pharmaceutically acceptable carrier.

* * * * *